US011045544B2

(12) United States Patent
Cummings et al.

(10) Patent No.: US 11,045,544 B2
(45) Date of Patent: Jun. 29, 2021

(54) METHODS OF GENERATING BIOACTIVE PEPTIDE-BEARING ANTIBODIES AND COMPOSITIONS COMPRISING THE SAME

(71) Applicant: Omeros Corporation, Seattle, WA (US)

(72) Inventors: W. Jason Cummings, Bellevue, WA (US); Patrick Gray, Seattle, WA (US); Larry Tjoelker, Kirkland, WA (US); Munehisa Yabuki, Seattle, WA (US)

(73) Assignee: Omeros Corporation, Seattle, WA (US)

( * ) Notice: Subject to any disclaimer, the term of this patent is extended or adjusted under 35 U.S.C. 154(b) by 5 days.

(21) Appl. No.: 15/459,645

(22) Filed: Mar. 15, 2017

(65) Prior Publication Data

US 2017/0247431 A1 Aug. 31, 2017

Related U.S. Application Data

(63) Continuation of application No. 14/207,143, filed on Mar. 12, 2014, now abandoned.

(60) Provisional application No. 61/962,289, filed on Mar. 15, 2013.

(51) Int. Cl.

| | |
|---|---|
| ***A61K 39/395*** | (2006.01) |
| ***C07K 16/18*** | (2006.01) |
| ***C07K 16/40*** | (2006.01) |
| ***C07K 16/00*** | (2006.01) |
| ***C07K 14/81*** | (2006.01) |
| *A61K 38/00* | (2006.01) |

(52) U.S. Cl.

CPC ........ *A61K 39/3955* (2013.01); *C07K 14/811* (2013.01); *C07K 16/00* (2013.01); *C12Y 304/21* (2013.01); *A61K 38/00* (2013.01); *C07K 2317/24* (2013.01); *C07K 2317/34* (2013.01); *C07K 2317/76* (2013.01); *C07K 2319/00* (2013.01); *C07K 2319/30* (2013.01); *C07K 2319/70* (2013.01)

(58) Field of Classification Search

None

See application file for complete search history.

(56) References Cited

U.S. PATENT DOCUMENTS

| | | | |
|---|---|---|---|
| 4,751,180 | A | 6/1988 | Cousens et al. |
| 4,935,233 | A | 6/1990 | Bell et al. |
| 4,946,778 | A | 8/1990 | Ladner et al. |
| 5,091,513 | A | 2/1992 | Huston et al. |
| 5,132,405 | A | 7/1992 | Huston et al. |
| 5,211,657 | A | 5/1993 | Yamada et al. |
| 6,765,087 | B1 | 7/2004 | Casterman et al. |
| 6,838,254 | B1 | 1/2005 | Hamers et al. |
| 7,083,786 | B2 | 8/2006 | Jensenius et al. |
| 7,112,414 | B2 | 9/2006 | Jensenius et al. |
| 7,919,094 | B2 | 4/2011 | Schwaeble et al. |
| 8,030,464 | B2 | 10/2011 | Altman |
| 2002/0019369 | A1 | 2/2002 | Li et al. |
| 2003/0104497 | A1 | 6/2003 | Kim et al. |
| 2006/0002937 | A1 | 1/2006 | Schwaeble et al. |
| 2007/0009528 | A1 | 1/2007 | Larsen et al. |
| 2009/0226421 | A1 | 9/2009 | Parren et al. |
| 2010/0093033 | A1 | 4/2010 | Maizels et al. |
| 2012/0135012 | A1 | 5/2012 | Kohler et al. |
| 2012/0258095 | A1 | 10/2012 | Demopulos et al. |
| 2012/0282263 | A1 | 11/2012 | Dudler et al. |
| 2013/0266559 | A1 | 10/2013 | Demopulos et al. |
| 2013/0266560 | A1 | 10/2013 | Demopulos et al. |
| 2013/0273053 | A1 | 10/2013 | Schwaeble et al. |
| 2013/0344073 | A1 | 12/2013 | Schwaeble et al. |
| 2014/0056873 | A1 | 2/2014 | Schwaeble et al. |
| 2015/0017162 | A1* | 1/2015 | Cummings ............ C07K 16/00 424/134.1 |

FOREIGN PATENT DOCUMENTS

| | | | |
|---|---|---|---|
| WO | WO 1993/11161 | A1 | 6/1993 |
| WO | WO 94/13804 | A1 | 6/1994 |
| WO | WO 04/009664 | A2 | 1/2004 |
| WO | WO 06/079372 | | 8/2006 |
| WO | WO 2007/048022 | A2 | 4/2007 |
| WO | WO 09/29315 | A2 | 3/2009 |
| WO | WO 2010/037402 | | 4/2010 |
| WO | WO 2012/007777 | A1 | 1/2012 |

OTHER PUBLICATIONS

Paul, Fundamental Immunology, 3rd Edition, 1993, pp. 292-295 (Year: 1993).*

Bendig M. M. (Methods: A Companion to Methods in Enzymology, 1995; 8:83-93) (Year: 1995).*

Rudikoff et al. (Proceedings of the National Academy of Sciences USA, vol. 79, p. 1979-1983, 1982) (Year: 1982).*

U.S. Appl. No. 13/083,441, filed Apr. 8, 2011, Schwaeble et al.

U.S. Appl. No. 12/905,972, filed Apr. 21, 2011, Schwaeble et al.

Barbas, S.M., et al., "Human Autoantibody Recognition of DNA," *Proc.Natl.Acad.Sci.U.S.A.* 92(7):2529-2533 (1995).

McLane, K.E., et al., "Transplantation of a 17-amino Acid alpha-helical DNA-binding Domain Into an Antibody Molecule Confers Sequence-Dependent DNA Recognition," *Proc.Natl.Acad.Sci.U.S.A.* 92(11):5214-5218 (1995).

(Continued)

*Primary Examiner* — Michael Allen

(74) *Attorney, Agent, or Firm* — Tineka J. Quinton, Esq.

(57) ABSTRACT

In one aspect, the invention provides a method of making a bioactive peptide-bearing antibody, or fragment thereof, comprising (a) engrafting the amino acid sequence of at least one bioactive peptide of interest into (i) at least one of CDR-H1, CDR-H2 or CDR-H3 of a heavy chain variable region comprising one or more chicken framework regions and/or (ii) at least one of CDR-L1, CDR-L2 or CDR-L3 of the light chain variable region comprising one or more chicken framework regions, and (b) determining whether the antibody has substantially the same biological activity as the bioactive peptide.

2 Claims, 14 Drawing Sheets

Specification includes a Sequence Listing.

(56) References Cited

OTHER PUBLICATIONS

Buerstedde, J.M., et al., "Light Chain Gene Conversion Continues at High Rate in ALV-induced Cell Line," *EMBO J.* 9(3):921-927 (1990).
Barbas, S.M., et al., "Recognition of DNA by Synthetic Antibodies," *J Am Chem Soc* 116(5):2161-2162 (1994).
Cummings, W.J., et al., "Genetic Variation Stimulated by Epigenetic Modification," *PLoS.One* 3(12):e4075 (2008).
Yabuki, M., et al., "Antibody Discovery Ex Vivo Accelerated by the LacO/Lacl Regulatory Network," *PLoS.One*. 7(4):e36032 (2012).
Hu, S., et al., "Minibody: A Novel Engineered Anti-Carcinoembryonic Antigen Antibody Fragment (Single-chain Fv-CH3) Which Exhibits Rapid, High-level Targeting of Xenografts," *Cancer Res.* 56(13):3055-3061 (1996).
Huston, J.S., et al., "Protein Engineering of Antibody Binding Sites: Recovery of Specific Activity in an Anti-Digoxin Single-chain Fv Analogue Produced in *Escherichia coli,*" *Proc.Natl.Acad.Sci.U.S.A.* 85(16):5879-5883 (1988).
Ill, C.R., et al., "Design and Construction of a Hybrid Immunoglobulin Domain with Properties of Both Heavy and Light Chain Variable Regions," *Protein Eng* 10(8):949-957 (1997).
Inbar D., et al., "Localization of Antibody-combining Sites Within the Variable Portions of Heavy and Light Chains," *Proc.Natl.Acad.U.S.A.* 69(9):2659-2662 (1972).
LoBuglio, A.F., et al., "Mouse/Human Chimeric Monoclonal Antibody in Man: Kinetics and Immune Response," *Proc.Natl.Acad.Sci.U.S.A.* 86(11):4220-4224 (1989).
Queen C., et al., "A Humanized Antibody that Binds to the Interleukin 2 Receptor," *Proc.Natl.Acad.Sci.U.S.A.* 86(24):10029-10033 (1988).
Ridgway, J.B., et al., "'Knobs-into-holes' Engineering of Antibody CH3 Domains for Heavy Chain Heterodimerization," *Protein Eng* 9(7):617-621 (1996).
Traunecker, A., et al., "Bispecific Single Chain Molecules (Janusins) Target Cytotoxic Lymphocytes on HIV Infected Cells," *EMBO J.* 10(12):3655-3659 (1991).
Riechmann, L., et al., "Reshaping Human Antibodies for Therapy," *Nature* 332(6162):323-327 (1988).
Ward, E.S., et al., "Binding Activities of a Repertoire of Single Immunoglobuline Variable Domains Secreted from *Escherichia coli,*" *Nature* 341(6242):544-546 (1989).
Reiter, Y., et al., "Engineering Antibody Fv Fragements for Cancer Detection and Therapy: Disulfide-stabilized Fv Fragments," *Nat. Biotechnol.* 14(10):1239-1245 (1996).
Hochman, J., et al., "Folding and Interaction of Subunits at the Antibody Combining Site," *Biochemistry* 15(12):2706-2710 (1976).
Ehrlich, P.H., et al., "Isolation of an Active Heavy-chain Variable Domain from a Homogeneous Rabit Antibody by Cathepsin B Digestion of the Aminoethylated Heavy Chain," *Biochemistry* 19(17):4091-4096 (1980).
Hollinger P., and Winter, G., "Engineering Bispecific Antibodies," *Curr.Opin.Biotechnol.* 4(4):446-449 (1993).
Traunecker, A., et al., "Janusin: New Molecular Design for Bispecific Reagents," *Int J. Cancer Suppl* 7:51-52 (1992).
Bray, B.L., :Large-scale Manufacture of Peptide Therapeutics By Chemical Synthesis, *Nat.Rev.Drug.Discov.* 2(7):587-593 (2003).
Spangler, J.B., et al., "Triepitopie Antibody Fusions Inhibit Cetuximad-resistant BFRAF and KRAS Mutant Tumors via EGFR Signal Repression," *J.Mol.Biol.* 422(4):532-544 (2012).
Kanakaraj, P., et al., "Simultaneous Targeting of TNF and Ang2 with a Novel Bispecific Antibody Enhances Efficacy in an in Vivo Model of Arthritis," *MAbs.* 4(5):600-613 (2012).
Edwards, C.M., et al., "Peptides as Drugs," *QJM* 92(1):1-4 (1999).
Liszewski, M.K., and Atkinson, J.P., "The Complement System," *Fundamental Immunology: Third Edition* 26:917-939, Raven Press, Ltd., New York (1993).
Kalli, et al., "Therapeutic Uses of Recombinant Complement Protein Inhibitors," *Springer Semin.Immunopathol.* 15(4):417-431 (1994).
Sim, R.B., and Laich, A., "Innate Immunity," *Biochem Society Transactions* 28(5):545-550 (2000).
Bird, R.E., et al., "Single-chain Antigen-binding Proteins," *Science* 242(4877):423-426 (1988).
Schwaeble, W., et al., "The Mannan-Binding Lectin-Associated Serine Proteases (MASPs) and MAp19: Four Components of the Lectin Pathway Activation Complex Encoed by Two Genes," Immunonbiol. 205:455-466 (2002).
Morgan, B.P., "Clinical Complementology: Recent Progress and Future Trends," *Eur.J.Clin.Invest.* 24(4):219-229 (1994).
Schwaeble, W., et al., "Targeting of Mannan-Binding Lectin-Associated Serine Protease-2 Confers Protection From Myocardial and Gastrointestinal Ischemia/Reperfusion Injury," *PNAS* 108(18):7523-7528 (2011).
Yongqing, T., et al., "Mannose-binding Lectin Serine Proteases and Associated Proteins of the Lectin Pathway of Complement: Two Genes, Five Proteins and Many Functions?" *Biochim.Biophys.Acta* 1824(1):253-262 (2012).
Heja, D., et al., "Monospecific Inhibitors Show that Both Mannan-bind Lectin-associated Serine Protease-1 (MASP-1) and -2 are Essential for Lectin Pathway Activation and Reveal Structural Plasticity of MASP-2," *J.Biol.Chem.* 287(24):20290-20300 (2012).
Graham, F.L., et al., "Characteristics of a Human Cell Line Transformed by DNA from Humans Adenovirus Type 5," *J.Gen.Virol.* 36(1):59-74 (1977).
Urlaub, G., and Chasin, L.A., "Isolation of Chinese Hamster Cell Mutants Deficient in Dihydrofolate Reductase Activity," *Proc.Natl.Acad.Sci.U.S.A.* 77(7):4216-4220 (1980).
Mather, J.P., "Establishment and Characterization of Two Distinct Mouse Testicular Epithelial Cell Lines," *Biol.Reprod.* 23(1):243-252 (1980).
Mather, J.P., et al., "Culture of Testicular cells in Hormone-supplemented Serum-free Medium," *Ann.N.Y.Acad.Sci.* 393:44-68 (1982).
Logan, J., and Shenk, T., "Adenovirus Tripartite Leader Sequence Enhances Translation of mRNAs Late After Infection," *Proc.Natl.Acad.Sci.U.S.A.* 81(12):3655-3659 (1984).
Kocsis, A., et al., "Selective Inhibition of the Lectin Pathway of Complement with Phage Display Selected Peptides Against Mannose-binding Lectin-associated Serine Protease," *J.Immunol.* 185(7):4169-4178 (2010).
Heja, D., et al., "Revised Mechanism of Complement Lectin-pathway Activation Revealing the Role of Serine Protease MASP-1 as the Exclusive Activator of MASP-2," *Proc.Natl.Acad.Sci.U.S.A.* 109(26):10498-10503 (2012).
Hollinger, P., et al., "'Diabodies': Small Bivalent and Bispecific Antibody Fragmetns," *Proc.Natl.Acad.Sci.U.S.A.* 90(14):6444-6448 (1993).
Seo, H., et al., "Rapid Generation of Specific Antibodies by Enhanced Homologous Recombination," *Nat.Biotechnol.* 23(6):731-735 (2005).
Maizels, N., "Immunoglobulin Gene Diversification," *Annu.Rev. Genet.* 39:23-46 (2005).
Cummings, W.J., et al., "Chromatin Structure Regulates Gene Conversion," *PLoS.Biol.* 5(10):2145-2155 (2007).
Cumbers, S.J., et al., "Generation and Iterative Affinity Maturation of Antibodies in Vitro Using Hypermutating B-cell Lines," *Nat. Biotechnol.* 20(11):1129-1134 (2002).
Wu, L., et al., "Fundamental Characteristics of the Immunoglobulin VH Repertoire of Chickens in Comparison with Those of Humans, Mice, and Camelids," *J.Immunol.* 188(1):322-333 (2012).
Murphy, J.R., et al., "Genetic Construction, Expression, and Melanoma-selective Cytotoxicity of a Diptheria Toxin-related alpha-Melanocyte-stiumlating Hormone Fusion Protein," *Proc.Natl.Acad.Sci.U.S.A.* 83(21):8258-8262 (1986).
Maratea, D., et al., "Deletion and Fusion Analysis of the Phage phi X174 Lysis Gene E," *Gene* 40(1):39-46 (1985).
Bitter, G.A., et al., "Expression and Secretion Vectors for Yeast" *Methods Enzymol.* 153:516-544 (1987).
Martin, F., et al., "The Affinity-Selection of a Minibody Polypeptide Inhibitor of Human Interleukin-6," *EMBO J.* 13(22):5303-5309 (1994).

* cited by examiner

| | | | | | | |
|---|---|---|---|---|---|---|
| DTLacO#2 | (aa94-125:SEQIDNO91) | ...YYCTK | | | CAYSSGCDYEGGYIDA | WGHGTEVIVSS |
| DTLacO#1 | (aa94-125:SEQIDNO23) | ...YYCAK | | | AAGGSGYCGSGAYIDA | WGHGTEVIVSS |
| | | | | | Native CDR-H3 | |
| SGMI-1L | (aa94-146:SEQIDNO50) | ...YYCAK | | LEVTCEPGTTFKDKCNTCRCGSDGKSAFCTRKLCYQ | A | WGHGTEVIVSS |
| SGMI-1M | (aa94-143:SEQIDNO52) | ...YYCAK | | TCEPGTTFKDKCNTCRCGSDGKSAFCTRKLCYQ | A | WGHGTEVIVSS |
| SGMI-1S | (aa94-130:SEQIDNO54) | ...YYCAK | | TCRCGSDGKSAFCTRKLCYQ | A | WGHGTEVIVSS |
| SGMI-1-L1 | (aa94-159:SEQIDNO56) | ...YYCAK | | LEVTCEPGTTFKDKCNTCRCGSDGKSAFCTRKLCYQ | GTGGGSGSSSYIDA | WGHGTEVIVSS |
| SGMI-1-L2 | (aa94-169:SEQIDNO58) | ...YYCAK | GTGGGSGSSS | LEVTCEPGTTFKDKCNTCRCGSDGKSAFCTRKLCYQ | GTGGGSGSSSYIDA | WGHGTEVIVSS |
| SGMI-1-L3 | (aa94-165:SEQIDNO60) | ...YYCAK | AAGGSG | LEVTCEPGTTFKDKCNTCRCGSDGKSAFCTRKLCYQ | GTGGGSGSSSYIDA | WGHGTEVIVSS |
| SGMI-1-L4 | (aa94-169:SEQIDNO62) | ...YYCAK | AAGGSGGSGA | LEVTCEPGTTFKDKCNTCRCGSDGKSAFCTRKLCYQ | GTGGGSGSSSYIDA | WGHGTEVIVSS |
| SGMI-1-L5 | (aa94-153:SEQIDNO64) | ...YYCAK | | LEVTCEPGTTFKDKCNTCRCGSDGKSAFCTRKLCYQ | GSGAYIDA | WGHGTEVIVSS |
| SGMI-1-L6 | (aa94-163:SEQIDNO66) | ...YYCAK | GTGGGSGSSS | LEVTCEPGTTFKDKCNTCRCGSDGKSAFCTRKLCYQ | GSGAYIDA | WGHGTEVIVSS |
| SGMI-1-L7 | (aa94-159:SEQIDNO68) | ...YYCAK | AAGGSG | LEVTCEPGTTFKDKCNTCRCGSDGKSAFCTRKLCYQ | GSGAYIDA | WGHGTEVIVSS |
| SGMI-1-L8 | (aa94-163:SEQIDNO70) | ...YYCAK | AAGGSGGSGA | LEVTCEPGTTFKDKCNTCRCGSDGKSAFCTRKLCYQ | GSGAYIDA | WGHGTEVIVSS |
| SGMI-1-L9 | (aa94-159:SEQIDNO72) | ...YYCAK | | LEVTCEPGTTFKDKCNTCRCGSDGKSAFCTRKLCYQ | AAGGSGGSGAYIDA | WGHGTEVIVSS |
| SGMI-1-L10 | (aa94-169:SEQIDNO74) | ...YYCAK | GTGGGSGSSS | LEVTCEPGTTFKDKCNTCRCGSDGKSAFCTRKLCYQ | AAGGSGGSGAYIDA | WGHGTEVIVSS |
| SGMI-1-L11 | (aa94-165:SEQIDNO76) | ...YYCAK | AAGGSG | LEVTCEPGTTFKDKCNTCRCGSDGKSAFCTRKLCYQ | AAGGSGGSGAYIDA | WGHGTEVIVSS |
| SGMI-1-L12 | (aa94-169:SEQIDNO78) | ...YYCAK | AAGGSGGSGA | LEVTCEPGTTFKDKCNTCRCGSDGKSAFCTRKLCYQ | AAGGSGGSGAYIDA | WGHGTEVIVSS |
| | | | N-term Linker | Bioactive peptide (SGMI-1) | C-term Linker | |

Symbol "---" indicates optional linker

METHODS OF GENERATING BIOACTIVE PEPTIDE-BEARING ANTIBODIES AND COMPOSITIONS COMPRISING THE SAME

CROSS-REFERENCE TO RELATED APPLICATIONS

This application is a continuation of pending U.S. application Ser. No. 14/207,143, filed Mar. 12, 2014, which claims benefit of U.S. Application Ser. No. 61/962,289, filed Mar. 15, 2013, now lapsed, which are hereby incorporated by reference in their entireties.

FIELD OF THE INVENTION

The present invention relates to methods for generating bioactive peptide-bearing antibodies and fragments thereof, such as antibodies comprising bioactive peptides for inhibiting complement activation.

STATEMENT REGARDING SEQUENCE LISTING

The sequence listing associated with this application is provided in text format in lieu of a paper copy and is hereby incorporated by reference into the specification. The name of the text file containing the sequence listing is MP_1_0164_US3_Sequence_Listing_Filed_20170315_ST25. The text file is 203 KB, was created on Mar. 14, 2017; and is being submitted via EFS-Web with the filing of the specification.

BACKGROUND

The complement system provides an early acting mechanism to initiate, amplify and orchestrate the immune response to microbial infection and other acute insults (M. K. Liszewski and J. P. Atkinson, 1993, in *Fundamental Immunology*, Third Edition, edited by W. E. Paul, Raven Press, Ltd., New York) in humans and other vertebrates. While complement activation provides a valuable first-line defense against potential pathogens, the activities of complement that promote a protective immune response can also represent a potential threat to the host (K. R. Kalli, et al., *Springer Semin. Immunopathol.* 15:417-431, 1994; B. P. Morgan, *Eur. J. Clinical Investig.* 24:219-228, 1994). For example, the C3 and C5 proteolytic products recruit and activate neutrophils. While indispensable for host defense, activated neutrophils are indiscriminate in their release of destructive enzymes and may cause organ damage. In addition, complement activation may cause the deposition of lytic complement components on nearby host cells as well as on microbial targets, resulting in host cell lysis.

The complement system has also been implicated in the pathogenesis of numerous acute and chronic disease states, including: myocardial infarction, stroke, acute respiratory distress syndrome, reperfusion injury, septic shock, capillary leakage following thermal burns, post cardiopulmonary bypass inflammation, transplant rejection, rheumatoid arthritis, multiple sclerosis, myasthenia gravis, age-related macular degeneration, paroxysmal nocturnal hemoglobinuria, and Alzheimer's disease. In almost all of these conditions, complement is not the cause but is one of several factors involved in pathogenesis. Nevertheless, complement activation may be a major pathological mechanism and represents an effective point for clinical control in many of these disease states.

The growing recognition of the importance of complement-mediated tissue injury in a variety of disease states underscores the need for effective complement inhibitory drugs. To date, Eculizumab (Soliris®), an antibody against C5, is the only complement-targeting drug that has been approved for human use. Yet, C5 is one of several effector molecules located "downstream" in the complement system, and blockade of C5 does not inhibit activation of the complement system. Therefore, an inhibitor of the initiation steps of complement activation would have many significant advantages over a "downstream" complement inhibitor.

Three distinct pathways of complement activation have been defined. The classical pathway is activated upon binding of particular antibody isotypes to a pathogen or host antigen. The lectin pathway is activated upon binding of pattern recognition lectins, such as mannan-binding lectin (MBL), CL-11, or ficolins L, M, or H to complex microbial or host macromolecules such as polysaccharides. Finally, the alternative pathway serves to amplify the signals generated by the classical and lectin pathways. A family of serine proteases is integral to the initial activation steps of all three pathways. C1r and C1s form the enzymatic components of the C1 complex that is assembled by complement-activating antibodies. In addition, there are three MBL-associated serine proteases (MASPs) that initiate and/or propagate the protease cascades of the lectin and alternative pathways (Yongqing et al., *Biochim. Biophys. Acta* 1824:253, 2012).

MASP-1, MASP-2 and MASP-3 share identical domain organizations with those of C1r and C1s, the enzymatic components of the C1 complex (Sim, R. B., et al., *Biochem. Soc. Trans.* 28:545, 2000). These domains include an N-terminal C1r/C1s/sea urchin VEGF/bone morphogenic protein (CUB) domain, an epidermal growth factor-like domain, a second CUB domain, a tandem of complement control protein domains, and a serine protease domain. As in the C1 proteases, activation of the MASP proteases occurs through cleavage of an Arg-Ile bond adjacent to the serine protease domain, which splits the enzyme into disulfide-linked A and B chains, the latter consisting of the serine protease domain.

The generation of specific peptide inhibitors of MASP-1 and MASP-2, termed SGMI-1 and SGMI-2, respectively, is described in Heja et al., *J Biol Chem* 287:20290 (2012) and Heja et al., *PNAS* 109:10498 (2012), each of which is hereby incorporated herein by reference. SGMI-1 and SGMI-2 are each 36 amino acid peptides which were selected from a phage library of variants of the *Schistocerca gregaria* protease inhibitor 2 in which six of the eight positions of the protease binding loop were fully randomized. Mechanistically, both SGMI-1 and SGMI-2 block the lectin pathway of complement activation without affecting the classical or alternative pathways (Heja et al., 2012. *Proc. Natl. Acad. Sci.* 109:10498). However, peptides such as SGMI-1 and SGMI-2 have limited potential for use in therapeutic applications because of the short half-life of peptides in serum.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the invention provides a method of making a bioactive peptide-bearing antibody, or fragment thereof, comprising (a) engrafting the amino acid sequence of at least one bioactive peptide of interest into (i) at least one of CDR-H1, CDR-H2 or CDR-H3 of a heavy chain variable region comprising one or more chicken framework regions and/or (ii) at least one of CDR-L1, CDR-L2 or CDR-L3 of a light chain variable region comprising one or more chicken framework regions, and (b) determining whether the antibody has substantially the same biological activity as the bioactive peptide.

In another aspect, the present invention provides an isolated antibody, or antigen-binding fragment thereof, comprising one or more bioactive peptide amino acid sequence(s), wherein at least one bioactive peptide amino acid sequence is engrafted into at least one of: (i) a light chain variable region comprising one or more chicken framework regions and/or (ii) a heavy chain variable region comprising one or more chicken framework regions. In some embodiments, a bioactive peptide amino acid sequence is engrafted into at least one of CDR-H1, CDR-H2 or CDR-H3 of a heavy chain variable region comprising one or more chicken framework regions. In some embodiments, the bioactive peptide amino acid sequence is engrafted into at least one of CDR-L1, CDR-L2 or CDR-L3 of a light chain variable region comprising one or more chicken framework regions.

In another aspect, the invention provides a method of making a bioactive peptide-bearing antibody, comprising (a) fusing the amino acid sequence of at least one bioactive peptide of interest onto: (i) an amino terminal region of at least one of: a light chain variable region comprising one or more chicken framework regions and/or a heavy chain variable region comprising one or more chicken framework regions, and/or (ii) a carboxy terminal region of at least one of: a light chain constant region and/or a heavy chain constant region; and (b) determining whether the antibody has substantially the same biological activity as the bioactive peptide.

In another aspect, the invention provides an isolated antibody, or antigen-binding fragment thereof, comprising a bioactive peptide amino acid sequence, wherein the bioactive peptide amino acid sequence is fused to at least one of (i) the amino terminal region of at least one of: a light chain variable region comprising one or more chicken framework regions and/or a heavy chain variable region comprising one or more chicken framework regions; or (ii) the carboxy terminal region of at least one of: a light chain constant region and/or a heavy chain constant region, wherein the antibody has substantially the same biological activity as the bioactive peptide.

In another aspect, the invention provides an isolated polypeptide comprising: (i) a region comprising an SGMI core sequence, the SGMI core sequence comprising an amino acid sequence according to: $X_1CTX_2X_3X_4CX_5Q$ (SEQ ID NO:5), wherein: $X_1$ is F or V, $X_2$ is R or K, $X_3$ is K or L, $X_4$ is L or W, and $X_5$ is Y or N; and (ii) a region comprising human IgG1 Fc, wherein the polypeptide inhibits the activity of at least one of MASP-1 or MASP-2.

In another aspect, the invention provides pharmaceutical compositions comprising the bioactive peptide-bearing antibodies, fragments thereof, and polypeptides, as disclosed herein.

In another aspect, the invention provides a method of inhibiting lectin pathway complement activation in a mammalian subject comprising administering a composition comprising a bioactive peptide-bearing antibody, or fragment thereof, or polypeptide, as disclosed herein, in an amount sufficient to inhibit lectin pathway complement activation in said mammalian subject.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 4 shows an alignment of the amino acid sequences of exemplary variable heavy chain polypeptides comprising the bioactive peptide SGMI-1, and variants thereof, engrafted within CDR-3, including optional linkers at the C-terminus and/or N-terminus of the bioactive peptide;

DESCRIPTION OF THE SEQUENCE LISTING

Figure 1:
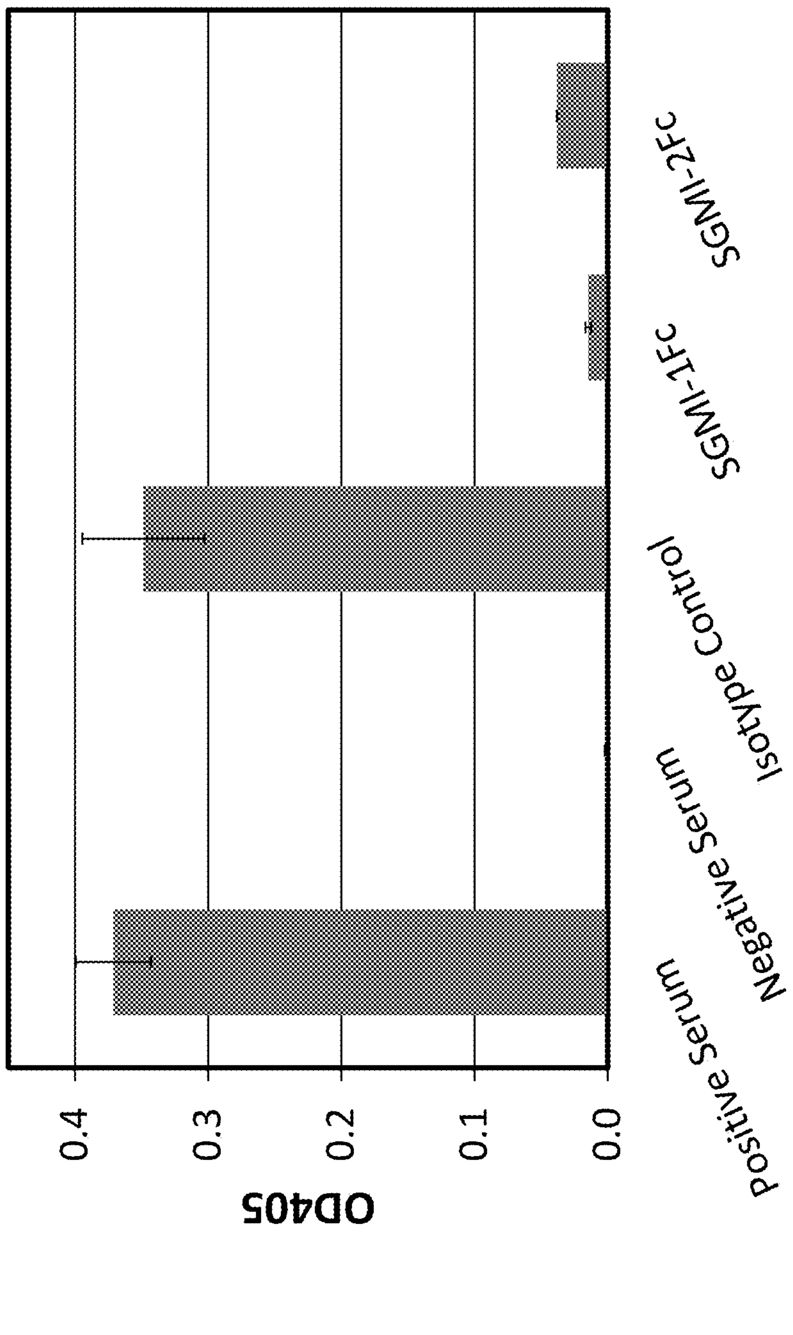
FIG. 1 is a bar graph showing the percent C5b-C9 formation in the presence of positive serum, negative serum, isotype control, SGMI-1Fc or SGMI-2Fc, demonstrating that both SGMI-1Fc and SGMI-2Fc inhibit the activation of the lectin pathway.

SEQ ID NO:1 human MASP-1 cDNA;

SEQ ID NO:2 human MASP-1 protein (with leader sequence);

SEQ ID NO:3 human MASP-2 cDNA;

SEQ ID NO:4 human MASP-2 protein (with leader sequence);

SEQ ID NO:5: SGMI peptide core sequence;

SEQ ID NO:6 SGMI-1L peptide (full length);

SEQ ID NO:7 SGMI-1M peptide (medium truncated version);

SEQ ID NO:8 SGMI-1S peptide (short truncated version);

SEQ ID NO:9 SGMI-2L peptide (full length);

SEQ ID NO:10 SGMI-2M peptide (medium truncated version);

SEQ ID NO:11 SGMI-2S peptide (short truncated version);

SEQ ID NO:12 human IgG1-Fc polypeptide;

SEQ ID NO:13 peptide linker #1 (12aa);

SEQ ID NO:14: peptide linker #2 (10aa);

SEQ ID NO:15: nucleic acid encoding polypeptide fusion comprising the human IL-2-signal sequence, SGMI-1L, linker #1, and human IgG1-Fc;

SEQ ID NO:16: mature polypeptide fusion comprising SGMI-1L, linker #1 and human IgG1-Fc (SGMI-1Fc);

SEQ ID NO:17: nucleic acid encoding polypeptide fusion comprising the human IL-2-signal sequence, SGMI-2L, linker #1 and human IgG1-Fc;

SEQ ID NO:18: mature polypeptide fusion comprising SGMI-2L, linker #1 and human IgG1-Fc (SGMI-2Fc);

SEQ ID NO:19: SGMI-1 forward primer;

SEQ ID NO:20: SGMI-1 reverse primer;

SEQ ID NO:21: SGMI-2 forward primer;

SEQ ID NO:22: SGMI-2 reverse primer; SEQ ID NO:23: parent DTLacO (clone #1) chicken heavy chain variable region (DTLacO_VH);

SEQ ID NO:24: conserved FR-1 region from chicken heavy chain variable region;

SEQ ID NO:25: conserved FR-2 region from chicken heavy chain variable region;

SEQ ID NO:26: conserved FR-3 region from chicken heavy chain variable region;

SEQ ID NO:27: conserved FR-3 flanking region adjacent to CDR-H3 from chicken heavy chain variable region;

SEQ ID NO:28: conserved FR-4 region from chicken heavy chain variable region;

SEQ ID NO:29: conserved FR-4 flanking region adjacent to CDR-H3 from chicken heavy chain variable region;

SEQ ID NO:30: Parent DTLacO (clone #1) chicken light chain variable region (DTLacO_VL);

SEQ ID NO:31: conserved FR-1 region from chicken light chain variable region;

SEQ ID NO:32: conserved FR-1 flanking region adjacent to CDR-L1 from chicken light chain variable region;

SEQ ID NO:33: conserved FR-2 region from chicken light chain variable region;

SEQ ID NO:34: conserved FR-2 flanking region adjacent to CDR-L1 from chicken light chain variable region;

SEQ ID NO:35: conserved FR-3 region from chicken light chain variable region;

SEQ ID NO:36: conserved FR-4 region from chicken light chain variable;

SEQ ID NO:37-46: peptide linkers

SEQ ID NO:47: human IgG1 constant region (CH1-hinge-CH2-CH3);

SEQ ID NO:48: human lambda light chain constant region;

SEQ ID NO:49: polynucleotide encoding the polypeptide comprising the human VH signal sequence, the SGMI-1L-bearing chicken VH sequence and the human IgG1 constant region (pcDNA3-SGMI-1L-IgG1);

SEQ ID NO:50: mature polypeptide comprising the SGMI-1L-bearing chicken VH region and the human IgG1 constant region (Ab-SGMI-1L-IgG1);

SEQ ID NO:51: polynucleotide encoding the polypeptide comprising the human VH signal sequence, the SGMI-1M-bearing chicken VH sequence and the human IgG1 constant region (pcDNA3-SGMI-1M-IgG1);

SEQ ID NO:52: mature polypeptide comprising the SGMI-1M-bearing chicken VH region and the human IgG1 constant region (Ab-SGMI-1M-IgG1);

SEQ ID NO:53: polynucleotide encoding the polypeptide comprising the human VH signal sequence, the SGMI-1S-bearing chicken VH sequence and the human IgG1 constant region (pcDNA3-SGMI-1 S-IgG1);

SEQ ID NO:54: mature polypeptide comprising the SGMI-1S-bearing chicken VH region and the human IgG1 constant region (Ab-SGMI-1S-IgG1);

SEQ ID NO:55: polynucleotide encoding the polypeptide comprising the human VH signal sequence, the SGMI-1-L1-bearing chicken VH sequence and the human IgG1 constant region (pcDNA3-SGMI-1-L1-IgG1);

SEQ ID NO:56: mature polypeptide comprising the SGMI-1-L1-bearing chicken VH region and the human IgG1 constant region (Ab-SGMI-1-L1-IgG1);

SEQ ID NO:57: polynucleotide encoding the polypeptide comprising the human VH signal sequence, the SGMI-1-L2-bearing chicken VH sequence and the human IgG1 constant region (pcDNA3-SGMI-1-L2-IgG1);

SEQ ID NO:58: mature polypeptide comprising the SGMI-1-L2-bearing chicken VH region and the human IgG1 constant region (Ab-SGMI-1-L2-IgG1);

SEQ ID NO:59: polynucleotide encoding the polypeptide comprising the human VH signal sequence, the SGMI-1-L3-bearing chicken VH sequence and the human IgG1 constant region (pcDNA3-SGMI-1-L3-IgG1);

SEQ ID NO:60: mature polypeptide comprising the SGMI-1-L3-bearing chicken VH region and the human IgG1 constant region (Ab-SGMI-1-L3-IgG1);

SEQ ID NO:61: polynucleotide encoding the polypeptide comprising the human VH signal sequence, the SGMI-1-L4-bearing chicken VH sequence and the human IgG1 constant region (pcDNA3-SGMI-1-L4-IgG1);

SEQ ID NO:62: mature polypeptide comprising the SGMI-1-L4-bearing chicken VH region and the human IgG1 constant region (Ab-SGMI-1-L4-IgG1);

SEQ ID NO:63: polynucleotide encoding the polypeptide comprising the human VH signal sequence, the SGMI-1-L5-bearing chicken VH sequence and the human IgG1 constant region (pcDNA3-SGMI-1-L5-IgG1);

SEQ ID NO:64: mature polypeptide comprising the SGMI-1-L5-bearing chicken VH region and the human IgG1 constant region (Ab-SGMI-1-L5-IgG1);

SEQ ID NO:65: polynucleotide encoding the polypeptide comprising the human VH signal sequence, the SGMI-1-L6-bearing chicken VH sequence and the human IgG1 constant region (pcDNA3-SGMI-1-L6-IgG1);

SEQ ID NO:66: mature polypeptide comprising the SGMI-1-L6-bearing chicken VH region and the human IgG1 constant region (Ab-SGMI-1-L6-IgG1);

SEQ ID NO:67: polynucleotide encoding the polypeptide comprising the human VH signal sequence, the SGMI-1-L7-bearing chicken VH sequence and the human IgG1 constant region (pcDNA3-SGMI-1-L7-IgG1);

SEQ ID NO:68: mature polypeptide comprising the SGMI-1-L7-bearing chicken VH region and the human IgG1 constant region (Ab-SGMI-1-L7-IgG1);

SEQ ID NO:69: polynucleotide encoding the polypeptide comprising the human VH signal sequence, the SGMI-1-L8-bearing chicken VH sequence and the human IgG1 constant region (pcDNA3-SGMI-1-L8-IgG1);

SEQ ID NO:70: mature polypeptide comprising the SGMI-1-L8-bearing chicken VH region and the human IgG1 constant region (Ab-SGMI-1-L8-IgG1);

SEQ ID NO:71: polynucleotide encoding the polypeptide comprising the human VH signal sequence, the SGMI-1-L9-bearing chicken VH sequence and the human IgG1 constant region (pcDNA3-SGMI-1-L9-IgG1);

SEQ ID NO:72: mature polypeptide comprising the SGMI-1-L9-bearing chicken VH region and the human IgG1 constant region (Ab-SGMI-1-L9-IgG1);

SEQ ID NO:73: polynucleotide encoding the polypeptide comprising the human VH signal sequence, the SGMI-1-L10-bearing chicken VH sequence and the human IgG1 constant region (pcDNA3-SGMI-1-L10-IgG1);

SEQ ID NO:74: mature polypeptide comprising the SGMI-1-L10-bearing chicken VH region and the human IgG1 constant region (Ab-SGMI-1-L10-IgG1);

SEQ ID NO:75: polynucleotide encoding the polypeptide comprising the human VH signal sequence, the SGMI-1-L11-bearing chicken VH sequence and the human IgG1 constant region (pcDNA3-SGMI-1-L11-IgG1);

SEQ ID NO:76: mature polypeptide comprising the SGMI-1-L11-bearing chicken VH region and the human IgG1 constant region (Ab-SGMI-1-L11-IgG1);

SEQ ID NO:77: polynucleotide encoding the polypeptide comprising the human VH signal sequence, the SGMI-1-L12-bearing chicken VH sequence and the human IgG1 constant region (pcDNA3-SGMI-1-L12-IgG1);

SEQ ID NO:78: mature polypeptide comprising the SGMI-1-L12-bearing chicken VH region and the human IgG1 constant region (Ab-SGMI-1-L12-IgG1);

SEQ ID NO:79: polynucleotide encoding the polypeptide comprising the human VL signal sequence, the SGMI-2L-bearing chicken VL sequence and the human Igλ, constant region (pcDNA3-SGMI-2L-Igλ);

SEQ ID NO:80: mature polypeptide comprising the SGMI-2L-bearing chicken VL region and the human Igλ constant region (Ab-SGMI-2L-Igλ);

SEQ ID NO:81: polynucleotide encoding the polypeptide comprising the human VL signal sequence, the SGMI-2M-bearing chicken VL sequence and the human Igλ constant region (pcDNA3-SGMI-2M-Igλ);

SEQ ID NO:82: mature polypeptide comprising the SGMI-2M-bearing chicken VL region and the human Igλ constant region (Ab-SGMI-2M-Igλ);

SEQ ID NO:83: polynucleotide encoding the polypeptide comprising the human VL signal sequence, the SGMI-2S-bearing chicken VL sequence and the human Igλ constant region (pcDNA3-SGMI-2S-Ig λ);

SEQ ID NO:84: mature polypeptide comprising the SGMI-2S-bearing chicken VL region and the human Igλ constant region (Ab-SGMI-2S-Igλ);

SEQ ID NO:85: polynucleotide encoding the polypeptide comprising the SGMI-1L-bearing chicken VL region and the human Igλ constant region (pcDNA3-SGMI-1L-Igλ);

SEQ ID NO:86: mature polypeptide comprising the SGMI-1L-bearing chicken VL region and the human Igλ constant region (Ab-SGMI-1L-Igλ);

SEQ ID NO:87: polynucleotide encoding a polypeptide comprising the SGMI-1M-bearing chicken VL region and the human Igλ constant region (pcDNA3-SGMI-1M-Igλ);

SEQ ID NO:88: mature polypeptide comprising the SGMI-1M-bearing chicken VL region and the human Igλ constant region (Ab-SGMI-1M-Igλ);

SEQ ID NO:89: polynucleotide encoding a polypeptide comprising the SGMI-1S-bearing chicken VL region and the human Igλ constant region (pcDNA3-SGMI-1S-Igλ);

SEQ ID NO:90: mature polypeptide comprising the SGMI-1S-bearing chicken VL region and the human Igλ constant region (Ab-SGMI-1S-Igλ);

SEQ ID NO:91: DTLacO chicken (clone #2) heavy chain variable region (DTLacO VH);

SEQ ID NO:92: DTLacO chicken (clone#2) light chain variable region (DTLacO VL);

SEQ ID NO:93: polynucleotide encoding the polypeptide comprising the human VH signal sequence, the SGMI-1-fused chicken VH sequence, and the human IgG1 constant region (pcDNA3-IgG1-S10);

SEQ ID NO:94: mature polypeptide comprising the SGMI-1-fused chicken VH region and the human IgG1 constant region (Ab-IgG1-S10);

SEQ ID NO:95: polynucleotide encoding the polypeptide comprising the human VH signal sequence, the SGMI-2-fused chicken VH sequence, and the human IgG1 constant region (pcDNA3-IgG1-S20);

SEQ ID NO:96: mature polypeptide comprising the SGMI-2-fused chicken VH region and the human IgG1 constant region (Ab-IgG1-S20);

SEQ ID NO:97: polynucleotide encoding the polypeptide comprising the human VH signal sequence, the chicken VH sequence, and the SGMI-1-fused human IgG1 constant region (pcDNA3-IgG1-S01);

SEQ ID NO:98: mature polypeptide comprising the chicken VH region and the SGMI-1-fused human IgG1 constant region (Ab-IgG1-S01);

SEQ ID NO:99: polynucleotide encoding the polypeptide comprising the human VH signal sequence, the chicken VH sequence, and the SGMI-2-fused human IgG1 constant region (pcDNA3-IgG1-S02);

SEQ ID NO:100: mature polypeptide comprising the chicken VH region and the SGMI-2-fused human IgG1 constant region (Ab-IgG1-S02);

SEQ ID NO:101: polynucleotide encoding the polypeptide comprising the human VL signal sequence, the SGMI-1-fused VL sequence and the human Igλ constant region (pcDNA3-Igλ-S10);

SEQ ID NO:102: mature polypeptide comprising the SGMI-1-fused chicken VL region and the human Igλ constant region (Ab-Igλ-S10);

SEQ ID NO:103: polynucleotide encoding the polypeptide comprising the human VL signal sequence, the SGMI-2-fused VL sequence and the human Igλ constant region (pcDNA3-Igλ-S20);

SEQ ID NO:104: mature polypeptide comprising the SGMI-2-fused chicken VL region and the human Igλ constant region (Ab-Igλ-S20);

SEQ ID NO:105: polynucleotide encoding the polypeptide comprising the human VL signal sequence, the chicken VL sequence, and the SGMI-1-fused human Igλ constant region (pcDNA3-Igλ-S01);

SEQ ID NO: 106: mature polypeptide comprising the chicken VL region, and the SGMI-1-fused human Igλ constant region (Ab-Igλ-S01;

SEQ ID NO:107: polynucleotide encoding the polypeptide comprising the human VL signal sequence, the chicken VL sequence, and the SGMI-2-fused human Igλ constant region (pcDNA3-Igλ-S02); and SEQ ID NO 108: mature polypeptide comprising the chicken VL region, and the SGMI-2-fused human Igλ constant region (Ab-Igλ-S02);

DETAILED DESCRIPTION

I. Definitions

Unless specifically defined herein, all terms used herein have the same meaning as would be understood by those of ordinary skill in the art of the present invention. The following definitions are provided in order to provide clarity with respect to the terms as they are used in the specification and claims to describe the present invention.

As used herein, an "antibody" is an immunoglobulin molecule capable of specific binding to a target, such as a carbohydrate, polynucleotide, lipid, polypeptide, etc., through at least one epitope recognition site, located in the variable region (also referred to herein as the variable domain) of the immunoglobulin molecule. In some embodiments, the antibody as disclosed herein comprises a variable region comprising chicken framework regions and further comprising a bioactive peptide amino acid sequence engrafted into a CDR region. In some embodiments, the antibody as disclosed herein comprises a variable region comprising chicken framework regions and further comprises a bioactive peptide fused to the amino and/or carboxy terminal region of the light and/or heavy chain. As used herein, the term antibody encompasses not only intact polyclonal or monoclonal antibodies, but also fragments thereof (such as a single variable region antibody (dAb), or other known antibody fragments such as Fab, Fab', $F(ab')_2$, Fv and the like, single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. "Diabodies", multivalent or multispecific fragments constructed by gene fusion (WO94/13804; P. Holliger et al, *Proc. Natl. Acad. Sci.*USA 90 6444-6448, 1993) are also a particular form of antibody contemplated herein. Minibodies comprising a scFv joined to a CH3 domain are also included herein (S. Hu et al, *Cancer Res.*, 56, 3055-3061, 1996). See e.g., Ward, E. S. et al., *Nature* 341, 544-546 (1989); Bird et al, *Science*, 242, 423-426, 1988; Huston et al, *PNAS* USA, 85, 5879-5883, 1988); PCT/US92/09965; WO94/13804; P. Holliger et al, *Proc. Natl. Acad. Sci.* USA 90 6444-6448, 1993; Y. Reiter et al, *Nature Biotech*, 14, 1239-1245, 1996; S. Hu et al, *Cancer Res.*, 56, 3055-3061, 1996. Nanobodies® and maxibodies are also contemplated (see, e.g., U.S. Pat. Nos. 6,765,087, 6,838,254, WO06/079372, WO/2010037402).

As used herein, the term "engrafted into a CDR region" refers to introducing a bioactive peptide sequence into at least one CDR region of a variable region of a heavy or light chain comprising chicken framework regions (FR1, FR2, FR3 and FR4) parental generic heavy or light chain, wherein the flanking framework regions remain intact, and wherein either the entire native CDR sequence is replaced with the bioactive peptide, or at least one amino acid, at least two, at least three, at least four, at least five, or more, up to all the amino acid residues of the native CDR sequence are retained as linker sequences flanking the bioactive peptide in the heavy or light chain variable region comprising the engrafted bioactive peptide.

As used herein, the term 'fused onto a light or heavy chain" refers to fusing a bioactive peptide sequence at the amino terminal region or at the carboxy terminal region of a heavy chain or light chain of an antibody comprising chicken framework regions.

The term "antigen-binding fragment" as used herein refers to a polypeptide fragment that contains at least one CDR of an immunoglobulin heavy and/or light chains that binds to the antigen of interest, including a polypeptide fragment that contains at least one bioactive peptide engrafted into a CDR, or a bioactive peptide fused to a light chain or heavy chain, wherein the polypeptide fragment binds to a target of the bioactive peptide, such as MASP-1 or MASP-2. In this regard, an antigen-binding fragment of the herein described antibodies may comprise 1, 2, 3, 4, 5, or all 6 CDRs of a VH and VL sequence set forth herein, wherein the antibodies bind a target of a bioactive peptide of interest, such as MASP-1 or MASP-2. An antigen-binding fragment of the herein described MASP-1 or MASP-2-specific antibodies is capable of binding to MASP-1 or MASP-2. In certain embodiments, binding of an antigen-binding fragment prevents or inhibits binding of a target of a bioactive peptide of interest (e.g., a GPCR ligand to its receptor), interrupting the biological response resulting from ligand binding to the receptor. In certain embodiments, the antigen-binding fragment binds specifically to and/or inhibits or modulates the biological activity of a target of a bioactive peptide of interest. In certain embodiments, the antigen-binding fragment binds specifically to and/or inhibits or modulates the biological activity of human MASP-1 and/or human MASP-2.

The term "antigen" refers to a molecule or a portion of a molecule capable of being bound by a selective binding agent, such as an antibody, including a target molecule or a portion of a molecule capable of being bound by a bioactive peptide of interest, and/or additionally capable of being used in an animal to produce antibodies capable of binding to an epitope of that antigen. An antigen may have one or more epitopes.

As used herein, an "epitope" refers to the site on a protein (e.g., a target of a bioactive peptide, such as MASP-1 or MASP-2 protein) that is bound by an antibody. "Overlapping epitopes" include at least one (e.g., two, three, four, five, or six) common amino acid residue(s), including linear and non-linear epitopes. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an antibody is said to specifically bind a protein target when it preferentially recognizes its target protein in a complex mixture of proteins and/or macromolecules. An antibody is said to specifically bind a target protein (also referred to as a target antigen) when the equilibrium dissociation constant is less than or equal to $10^{-6}$M, or less than or equal to $10^{-7}$M, or less than or equal to $10^{-8}$ M. In some embodiments, the equilibrium dissociation constant may be less than or equal to $10^{-9}$ M or less than or equal to $10^{-10}$ M.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the $F(ab')_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. See e.g., Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

In certain embodiments, single chain Fv or scFV antibodies are contemplated. For example, Kappa bodies (III et al., *Prot. Eng.* 10: 949-57 (1997); minibodies (Martin et al., *EMBO J.* 13:5305-9 (1994); diabodies (Holliger et al., *PNAS* 90:6444-8 (1993); or Janusins (Traunecker et al., *EMBO J.* 10:3655-59 (1991) and Traunecker et al. *Int. J. Cancer Suppl.* 7: 51-52 (1992), may be prepared using standard molecular biology techniques following the teachings of the present application with regard to selecting antibodies having the desired specificity. In still other embodiments, bispecific or chimeric antibodies may be made that encompass the engrafted bioactive peptides and/or bioactive peptide fusions of the present disclosure. For example, a chimeric antibody may comprise CDRs and framework regions from different antibodies, while bispecific antibodies may be generated that bind specifically to the target of a first bioactive peptide through one binding domain and to a target of a second bioactive peptide through a second binding domain. In another embodiment, bi-specific and/or tri-specific antibodies may be generated that bind to the target of the parent antibody through one binding domain and to a target of the first and/or second bioactive peptide through a second and/or third binding domain introduced by the presence of the bioactive peptide. These antibodies may be produced through recombinant molecular biological techniques or may be physically conjugated together.

A single chain Fv (scFv) polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci.* USA 85(16):5879-5883. A number of methods have been described to discern chemical structures for converting the naturally aggregated—but chemically separated—light and heavy polypeptide chains from an antibody variable (V) region into an scFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al. A dAb fragment of an antibody consists of a VH domain (Ward, E. S. et al., *Nature* 341, 544-546 (1989)).

In certain embodiments, an antibody as herein disclosed (e.g., a MASP-1 or MASP-2-specific antibody) is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above. Diabodies and scFv can be constructed without an Fc region, using only variable regions, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al, *Protein Eng.*, 9, 616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This proprietary antibody technology creates a stable, smaller antibody format with an anticipated longer therapeutic window than current small antibody formats. IgG4 antibodies do not activate the complement system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The UniBody® is about half the size of a regular IgG4 antibody. This small size can be a great benefit when treating some forms of cancer, allowing for better distribution of the molecule over larger solid tumors and potentially increasing efficacy.

In certain embodiments, the antibodies of the present disclosure may take the form of a Nanobody®. Nanobodies® are encoded by single genes and are efficiently produced in almost all prokaryotic and eukaryotic hosts e.g. *E. coli* (see e.g. U.S. Pat. No. 6,765,087), molds (for example *Aspergillus* or *Trichoderma*) and yeast (for example *Saccharomyces, Kluyvermyces, Hansenula* or *Pichia* (see e.g. U.S. Pat. No. 6,838,254). The production process is scalable and multi-kilogram quantities of Nanobodies® have been produced. Nanobodies® may be formulated as a ready-to-use solution having a long shelf life. The Nanoclone method (see ego WO 06/079372) is a proprietary method for generating Nanobodies® against a desired target, based on automated high-throughput selection of B-cells.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 70-90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

As used herein, the term "chicken framework region or a variant thereof" refers to the FR regions of a chicken antibody, and conserved variants thereof, for example as disclosed herein and further described in Wu et al., J. Immunol 188:322-333 (2012), hereby incorporated herein by reference.

The structures and locations of immunoglobulin variable regions may be determined by reference to Kabat, E. A. et al, Sequences of Proteins of Immunological Interest. 4th Edition. US Department of Health and Human Services. 1987, and updates thereof, now available on the Internet (immuno.bme.nwu.edu).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', $F(ab')_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody."

"Humanized" antibodies refer to a chimeric molecule, generally prepared using recombinant techniques, having an antigen-binding site derived from an immunoglobulin from a non-human species (e.g., a chicken) and the remaining immunoglobulin structure of the molecule based upon the structure and/or sequence of a human immunoglobulin. The antigen-binding site may comprise either complete variable regions fused onto constant domains or only the CDRs grafted (including CDRs comprising engrafted bioactive peptide sequences) onto appropriate framework regions in the variable regions. Epitope binding sites may be wild type or modified by one or more amino acid substitutions. This eliminates the constant region as an immunogen in human individuals, but the possibility of an immune response to the foreign variable region remains (LoBuglio, A. F. et al., (1989) *Proc Natl Acad Sci* USA 86:4220-4224; Queen et al., *PNAS* (1988) 86:10029-10033; Riechmann et al., *Nature* (1988) 332:323-327).

In certain embodiments, the antibodies of the present disclosure may be chimeric antibodies. In this regard, in one embodiment, a chimeric antibody is comprised of an antigen-binding fragment of an antibody comprising a bioactive peptide sequence engrafted into a CDR of a variable region operably linked or otherwise fused to a heterologous Fc portion of a different antibody, or fused to the N- or C-terminus of the heavy or light chain. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the antigen-binding fragment of a chimeric antibody may comprise only one or more of the CDRs of the antibodies described herein (e.g., 1, 2, 3, 4, 5, or 6 CDRs of the antibodies described herein), or may comprise an entire variable region (VL, VH or both).

In certain embodiments, an antibody comprising an engrafted bioactive peptide sequence comprises one or more of the CDRs of the antibodies described herein. In this regard, it has been shown in some cases that the transfer of only the VH-CDR3 of an antibody can be done while still retaining desired specific binding (Barbas et al., *PNAS* (1995) 92: 2529-2533). See also, McLane et al., *PNAS* (1995) 92:5214-5218, Barbas et al., *J. Am. Chem. Soc.* (1994) 116:2161-2162.

As used herein, the term "MASP-2-dependent complement activation" comprises MASP-2-dependent activation of the lectin pathway, which occurs under physiological conditions (i.e., in the presence of $Ca^{++}$) leading to the formation of the C3 convertase C4b2a and upon accumulation of the C3 cleavage product C3b subsequently to the C5 convertase C4b2a(C3b)n.

As used herein, the term "MASP-1-dependent complement activation" comprises MASP-1 dependent activation of the lectin pathway, which occurs under physiological conditions (i.e., in the presence of $Ca^{++}$) leading to the formation of the C3 convertase C4b2a and upon accumulation of the C3 cleavage product C3b subsequently to the C5 convertase C4b2a(C3b)n.

As used herein, the term "lectin pathway" refers to complement activation that occurs via the specific binding of serum and non-serum carbohydrate-binding proteins including mannan-binding lectin (MBL), CL-11 and the ficolins (H-ficolin, M-ficolin, or L-ficolin).

As used herein, the term "MASP-2 inhibitory antibody" refers to any MASP-2 antibody, or MASP-2 binding fragment thereof, that binds to or directly interacts with MASP-2 and effectively inhibits MASP-2-dependent complement activation. MASP-2 inhibitory antibodies useful in the method of the invention may reduce MASP-2-dependent complement activation by greater than 20%, such as greater than 30%, or greater than 40%, or greater than 50%, or greater than 60%, or greater than 70%, or greater than 80%, or greater than 90%, or greater than 95%.

As used herein, the term "MASP-1 inhibitory antibody" refers to any MASP-1 antibody, or MASP-1 binding fragment thereof, that binds to or directly interacts with MASP-1 and effectively inhibits MASP-1-dependent complement activation. MASP-1 inhibitory antibodies useful in the method of the invention may reduce MASP-1-dependent complement activation by greater than 20%, such as greater than 30%, or greater than 40%, or greater than 50%, or greater than 60%, or greater than 70%, or greater than 80%, or greater than 90%, or greater than 95%.

As used herein, the term "MASP-2 blocking antibody" refers to MASP-2 inhibitory antibodies that reduce MASP-2-dependent complement activation by greater than 90%, such as greater than 95%, or greater than 98% (i.e., resulting in MASP-2 complement activation of only 10%, such as only 9%, or only 8%, or only 7%, or only 6%, such as only 5% or less, or only 4%, or only 3% or only 2% or only 1%).

As used herein, the term "MASP-1 blocking antibody" refers to MASP-1 inhibitory antibodies that reduce MASP-1-dependent complement activation by greater than 90%, such as greater than 95%, or greater than 98% (i.e., resulting in MASP-1 complement activation of only 10%, such as only 9%, or only 8%, or only 7%, or only 6%, such as only 5% or less, or only 4%, or only 3% or only 2% or only 1%).

As used herein, the term "variant" antibody sequence refers to a molecule which differs in amino acid sequence from a "parent" or reference antibody amino acid sequence by virtue of addition, deletion, and/or substitution of one or more amino acid residue(s) in the parent antibody sequence. In one embodiment, a variant antibody sequence refers to a molecule which contains one or more framework regions that are identical to the parent framework domains, except for a combined total of 1, 2, 3, 4, 5, 6, 7, 8 9 or 10 amino acid substitutions within the framework regions of the heavy chain variable region, and/or up to a combined total of 1, 2, 3, 4, 5, 6, 7, 8, 9, or 10 amino acid substitutions with said framework regions of the light chain variable region. In some embodiments, the amino acid substitutions are conservative sequence modifications. In some embodiments, the variant framework region(s) of the variable light chain and/or the variable heavy chain comprise or consist of an amino acid sequence having at least 85% identity, such as least 86%, or at least 87%, or at least 88% or at least 89%, or at least 90%, or at least 91%, or at least 92%, or at least 93%, or at least 94% or at least 95%, or at least 96%, or at least 97%, or at least 98% or at least 99% or 100% identity with at least one or more of the chicken framework regions VL-FR1, VL-FR2, VL-FR3 and VL-FR4 amino acid sequences set forth in SEQ ID NO:s 31, 33, 35 and 36, respectively; or with at least one or more of the chicken framework regions. VH-FR-1, VH-FR2, VH-FR3 and VH-FR4 amino acid sequences set forth in SEQ ID NO:s 24, 25, 26, and 28, respectively.

As used herein, the term "parent chicken antibody" refers to an antibody which is encoded by an amino acid sequence used for the preparation of the variant comprising a bioactive peptide engrafted into or onto at least one of the variable region of the heavy or light chain. The parent antibody has a chicken framework region and, if present, typically has human antibody constant region(s).

As used herein, the amino acid residues are abbreviated as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

As used herein, the term "isolated antibody" refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, an "isolated nucleic acid molecule" is a nucleic acid molecule (e.g., a polynucleotide) that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

As used herein, a "nucleic acid molecule construct" is a nucleic acid molecule, either single- or double-stranded, that has been modified through human intervention to contain segments of nucleic acid combined and juxtaposed in an arrangement not existing in nature.

As used herein, an "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein, the terms "approximately" or "about" in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

As used herein the singular forms "a", "an" and "the" include plural aspects unless the context clearly dictates otherwise. Thus, for example, reference to "a cell" includes a single cell, as well as two or more cells; reference to "an agent" includes one agent, as well as two or more agents; reference to "an antibody" includes a plurality of such antibodies and reference to "a framework region" includes reference to one or more framework regions and equivalents thereof known to those skilled in the art, and so forth.

As used herein, "a subject" includes all mammals, including without limitation, humans, non-human primates, dogs, cats, horses, sheep, goats, cows, rabbits, pigs and rodents.

As used herein, the term "bioactive peptide" refers to a peptide having a biological activity.

The term "peptide" as used herein refers to a plurality of amino acids joined together in a linear chain via peptide bonds, including a dipeptide, tripeptide, oligopeptide and polypeptide. The term oligopeptide is typically used to describe peptides having from at least 2 to about 50 or more (e.g., from 2 amino acids to 60 amino acids in length, such as from about 5 to about 50 amino acids, such as from about 5 to about 40, or from about 5 to about 30 amino acids in length). Peptides larger than 60 amino acids are referred to herein as polypeptides or proteins.

As used herein, the term "bioactive" or "bioactivity" as used herein includes, but is not limited to, any type of interaction with another biomolecule, such as a protein, glycoprotein, carbohydrate, for example an oligosaccharide or polysaccharide, nucleotide, polynucleotide, fatty acid, hormone, enzyme, cofactor or the like, whether the interactions involve covalent or noncovalent binding. Bioactivity further includes interactions of any type with other cellular components or constituents including salts, ions, metals, nutrients, foreign or exogenous agents present in a cell such as viruses, phage and the like, for example binding, sequestration or transport-related interactions. Bioactivity of a peptide can be detected, for example, by observing phenotypic effects in a host cell in which it is expressed, or by performing an in vitro assay for a particular bioactivity, such as affinity binding to a target molecule, alteration of an enzymatic activity, or the like. Examples of bioactive peptides include antimicrobial peptides and peptide drugs. Antimicrobial peptides are peptides that adversely affect a microbe such as a bacterium, virus, protozoan, or the like. Antimicrobial peptides include, for example, inhibitory peptides that slow the growth of a microbe, microbiocidal peptides that are effective to kill a microbe (e.g., bacteriocidal and virocidal peptide drugs, sterilants, and disinfectants), and peptides effective to interfere with microbial reproduction, host toxicity, or the like. Peptide drugs for therapeutic use in humans or other animals include, for example, antimicrobial peptides that are not prohibitively toxic to the patient, and peptides designed to elicit, speed up, slow down, or prevent various metabolic processes in the host such as insulin, oxytocin, calcitonin, gastrin, somatostatin, anticancer peptides, and the like.

As used herein, the term "wherein the isolated antibody has substantially the same biological activity as the unmodified bioactive peptide" refers to wherein the isolated antibody comprising the bioactive peptide sequence has at least 70%, or at least 80%, or at least 85%, or at least 90% or at least 95%, or at least 98%, or at least 99% of the biological activity as compared to the original, unmodified form of the corresponding bioactive peptide.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y.; Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or other relevant Current Protocol publications and other like references. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

It is contemplated that any embodiment discussed in this specification can be implemented with respect to any method, kit, reagent, or composition of the invention, and vice versa. Furthermore, compositions of the invention can be used to achieve methods of the invention.

II. Overview

Bioactive peptides are peptides (i.e., from 2 to 60 amino acid residues in length, such as from about 5 to about 50 amino acids, such as from about 5 to about 40 amino acids in length, such as from about 5 to about 30 amino acids in length, or such as a peptide having a length of no more than 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 amino acid residues) that elicit a biological activity. For example, the bioactive peptides SGMI-1 (set forth as SEQ ID NO:6) and SGMI-2 (set forth as SEQ ID NO:9) are each 36 amino acid residues in length and are highly specific inhibitors of MASP-1 and MASP-2, respectively. However, as peptide they have limited potential for use in biological studies and therapeutic applications. For example, peptide instability within the biological system of interest often occurs, as evidenced by the unwanted degradation of potential peptide drugs by proteases and/or peptidases in the host cells.

In order to engineer bioactive peptides, such as SGMI-1 and SGMI-2, for use as therapeutic agents, the inventors have generated bioactive peptide-bearing antibodies and fragments thereof by engrafting amino acid sequences encoding bioactive peptides into or fused onto three distinct scaffolds: (1) fused onto the amino terminus of human IgG1 Fc region to create an Fc-fusion protein, as described in Example 2; (2) engrafted into various complementarity-determining regions (CDR) of a chimeric chicken (variable regions)—human (IgG1 and Igλ constant regions) antibody, as described in Example 3; and (3) fused onto the amino or carboxy termini of the heavy and/or light chains of an antibody, as described in Example 4. Using the methods described herein, the inventors have produced bioactive peptide-bearing antibodies and fragments thereof which surprisingly have substantially the same biological activity of the bioactive peptide when measured in vitro, with the advantages of increased stability for use as a therapeutic agent in a living subject.

III. Bioactive Peptide-Bearing Antibodies

In accordance with the foregoing, in one aspect, the invention provides a method of making a bioactive peptide-bearing antibody, the method comprising (a) engrafting the amino acid sequence of at least one bioactive peptide of interest into (i) at least one of CDR-H1, CDR-H2 or CDR-H3 of a heavy chain variable region comprising chicken framework regions and/or (ii) at least one of CDR-L1, CDR-L2 or CDR-L3 of the light chain variable region comprising chicken framework regions, and (b) determining whether the antibody has substantially the same biological activity as the bioactive peptide.

The method in accordance with this aspect of the invention may be used to generate a bioactive peptide-bearing antibody, wherein the antibody comprises the amino acid sequence of any bioactive peptide of interest. Bioactive peptides have been isolated from a variety of systems, exhibit a wide range of actions, and have been utilized as therapeutic agents in the field of medicine and as diagnostic tools in both basic and applied research. The mode of action of bioactive peptides has been found to be due to the interaction of the bioactive peptide with a specific protein target. The bioactive peptide acts by binding to and either activating or inactivating its protein target with extremely high specificities. Binding constants of bioactive peptides for their protein targets typically have been determined to be in the nanomolar (nM) range with binding constants as potent as picomolar range having been reported.

The methods of this aspect of the invention may be used to generate an antibody comprising an amino acid sequence with any bioactive peptide. Exemplary bioactive peptides for use in the methods of the invention include (i) bioactive peptides that inhibit medically-important proteases, (ii) neuropeptides (iii) bioactive peptides that inhibit or activate neuropeptide activity, (iii) peptide hormones, (iv) bioactive peptides that inhibit or activate peptide hormone activity, (v) peptides that are ligands for Class A GPCRs, (vi) bioactive peptides that inhibit or activate Class A GPCRs, (vii) Class B GPCR ligands, and (viii) bioactive peptides that inhibit or activate Class B GPCRs.

For example, medically-important proteases that are inhibited by bioactive peptides include, but are not limited to: Gamma-secretase, PAR-1, PAR-2, PAR-3, Cathepsin, Incretin, Dipeptidyl peptidase IV, Angiotensin-converting enzyme, Calpain, Caspase-3, Carboxypeptidase, Thrombin, and proteases in the clotting cascade and complement pathways. Examples of complement pathway serine protease inhibitors (e.g., MASP-1, MASP-2 inhibitors), include the bioactive peptide inhibitors SGMI-1 and SGMI-2.

Examples of neuropeptides include, but are not limited to: N-Acetylaspartylglutamic acid, agouti-related peptide, alpha-endorphin, Big dynorphin, Bombesin, Bombesin-like peptides, Carbetocin, Cocaine-and-amphetamine regulated transcript (CART), Cholecystokinin, Corazonin, Corticotropin-like intermediate peptide, Cortistatin, Demoxytocin, Dynorphin A, Dynorphin B, Eledoisin, Encephalin, Galanin, Galanin-like peptide, Galmic, Galnon, Gamma-endorphin, Ghrelin, Hemopressin, Kisspeptin, Neurokinin B, Neuromedin B, Neuromedin N, Neuromedin S, Neuromedin U, Neuromedin S, Neuromedin Y, Neuropeptide Y, Neurotensin, Nociceptin, Opiorphin, Orexin, Orexin-A, Oxytocin, Physalaemin, Preprotachykinin, Proctolin, Proenkephalin, Proopiomelanocortin, Protein episteme, Relaxin-3, RVD-Pα, Somatostatin, Substance P, TAC1, Tacchykinin peptides, TRH, Vasopressin, Vasotocin, VIP, and VGF.

Examples of peptide hormones include, but are not limited to: Activin and inhibin, Adiponectin, Adipose-derived hormones, Adrenocorticotropic hormone, Afamelanotide, Agouti gene, Agouti signaling peptide, Allatostatin, Amylin, Amylin family, Angiotensin, Atrial natriuretic peptide, Big gastrin, Bovine somatotropin, Bradykinin, Brain-derived neurotrophic factor, Calcitonin, cholecystokinin, Ciliary neurotrophic factor, CJC-1293, CJC-1295, Corticotropin-releasing hormone, Cosyntropin, Crustacean neurohormone family, Endothelian, Enteroglucagon, FGF15, GFG15/19, Follicle-stimulating hormone, Gastrin, Gastroinhibitory peptide, Ghrelin, Glucagon, Glucagon-like peptide-1, Gonadotropin, Gonadotropin-preparations, Gonadotropin-releasing hormone, Granulocyte-colony-stimulating factor, Growth hormone, Growth-hormone-releasing hormone, Hepcidin, Human chorionic gonadotropin, Human placental lactogen, Incretin, Insulin, Insulin analog, Insulin aspart, Insulin degludec, Insulin glargine, Insulin lispro, Insulin-like growth factor, Insulin-like growth factor-1, Insulin-like growth factor-2, Leptin, Liraglutide, Little gastrin I, Luteinizing hormone, Melanocortin, Melanocyte-stimulating hormone, Alpha-Melanocyte-stimulating hormone, Melanotan II, Minigastrin, N-terminal prohormone of brain natriuretic peptide, Nerve growth factor, Neurotrophin-3, Neurotrophin-4, NPH insulin, Obestatin, Orexin, Osteocalcin, Pancreatic hormone, Parathyroid hormone, Peptide hormone, Peptide YY, Plasma renin activity, Pramlintide, Preprohormone, Prolactin, Relaxin, Relaxin family peptide hormone, Renin, Salcatonin, Secretin, Secretin family peptide hormone, Sincalide, Teleost leptins, Temporin, Tesamorelin, Thyroid-stimulating hormone, Thyrotropin-releasing hormone, Urocortin, Urocortin II, Urocortin III, Vasoactive intestinal peptide, and Vitellogenin.

Examples of Class B GPCR ligands include, but are not limited to: VIP (28aa), PACAP (38aa), and CRF1 (41aa).

Tables 1 and 2 list representative bioactive peptides suitable for use in the methods of the invention.

TABLE 1

Representative Bioactive Peptides Utilized in Medicine

| Name | Isolated from | Size (amino acid residues) | Therapeutic Use |
|---|---|---|---|
| Angiotensin II | Human Plasma | 8 | Vasoconstrictor |
| Bradykinin | Human Plasma | 9 | Vasodilator |
| Caerulein | From Skin | 10 | Choleretic Agent |
| Calcitonin | Human Parathyroid Gland | 32 | Calcium Regulator |
| Cholecystokinin | Porcine Intestine | 33 | Choleretic Agent |
| Corticotropin | Porcine Pituitary Gland | 39 | Hormone |
| Eledoisin | Octopod Venom | 11 | Hypotensive Agent |
| Gastrin | Porcine Stomach | 17 | Gastric Activator |
| Glucagon | Porcine Pancreas | 29 | Antidiabetic Agent |
| Gramicidin D | Bacillus brevis | 11 | Antibacterial Agent |
| Insulin | Canine Pancreas | | Antidiabetic Agent |
| Insulin A | | 21 | |
| Insulin B | | 30 | |
| Kallidin | Human Plasma | 10 | Vasodilator |
| Luteinizing Hormone Releasing Factor | Bovine Hypothalamus | 10 | Hormone Stimulator |
| Melittin | Bee Venom | 26 | Antirheumatic Agent |
| Oxytocin | Bovine Pituitary Gland | 9 | Oxytocic Agent |
| Secretin | Canine Intestine | 27 | Hormone |
| Sermorelin | Human Pancreas | 29 | Hormone Stimulator |
| Somatostatin | Bovine Hypothalamus | 14 | Hormone Inhibitor |
| Vasopressin | Bovine Pituitary Gland | 9 | Antidiuretic Agent |

TABLE 2

Representative Bioactive Peptides Utilized in Applied Research

| Name | Isolated from | Size (amino acid residues) | Biological activity |
|---|---|---|---|
| Atrial Natriuretic Peptide | Rat Atria | 28 | Natriuretic Agent |
| Peptide Bombesin | Frog Skin | 14 | Gastric Activator |
| Conantokin G | Snail Venom | 17 | Neurotransmitter |
| Conotoxin G1 | Snail Venom | 13 | Neuromuscular Inhibitor |
| Defensin HNP-1 | Human Neutrophils | 30 | Antimicrobial Agent |
| Delta Sleep-Inducing Peptide | Rabbit Brain | 9 | Neurological Affector |
| Dermaseptin | Frog Skin | 34 | Antimicrobial Agent |

TABLE 2-continued

Representative Bioactive Peptides Utilized in Applied Research

| Name | Isolated from | Size (amino acid residues) | Biological activity |
|---|---|---|---|
| Dynorphin | Porcine Brain | 17 | Neurotransmitter |
| EETI II | *Ecballium elaterium* seeds | 29 | Protease Inhibitor |
| Endorphin | Human Brain | 30 | Neurotransmitter |
| Enkephalin | Human Brain | 5 | Neurotransmitter |
| Histatin 5 | Human Saliva | 24 | Antibacterial Agent |
| Mastoparan | Vespid Wasps | 14 | Mast Cell Degranulator |
| Magainin 1 | Frog Skin | 23 | Antimicrobial Agent |
| Melanocyte | Porcine Pituitary | 13 | Hormone Stimulator |
| Motilin | Canine Intestine | 22 | Gastric Activator |
| Neurotensin | Bovine Brain | 13 | Neurotransmitter |
| Physalaemin | Frog Skin | 11 | Hypotensive Agent |
| Substance P | Horse Intestine | 11 | Vasodilator |
| Vasoactive Intestinal Peptide | Porcine Intestine | 28 | Hormone |

In accordance with the methods of this aspect of the invention, an amino acid sequence of a bioactive peptide of interest is engrafted into at least one CDR region of a variable region of a heavy chain comprising one or more chicken framework regions (VH-FR1, VH-FR2, VH-FR3, VH-FR4), or is engrafted into at least one CDR region of a variable region of a light chain comprising one or more chicken framework regions (VL-FR1, VL-FR2, VL-FR3, VL-FR4), such as a heavy chain or light chain variable region from a parental chicken generic antibody, as described in Example 3 and illustrated in FIGS. 3-6. The bioactive peptide is engrafted into a CDR such that the flanking framework regions adjacent the CDR in the variable heavy or light chain remain intact. In some embodiments, the entire native CDR sequence of the generic parental antibody is removed and replaced with the bioactive peptide sequence.

Figure 5:
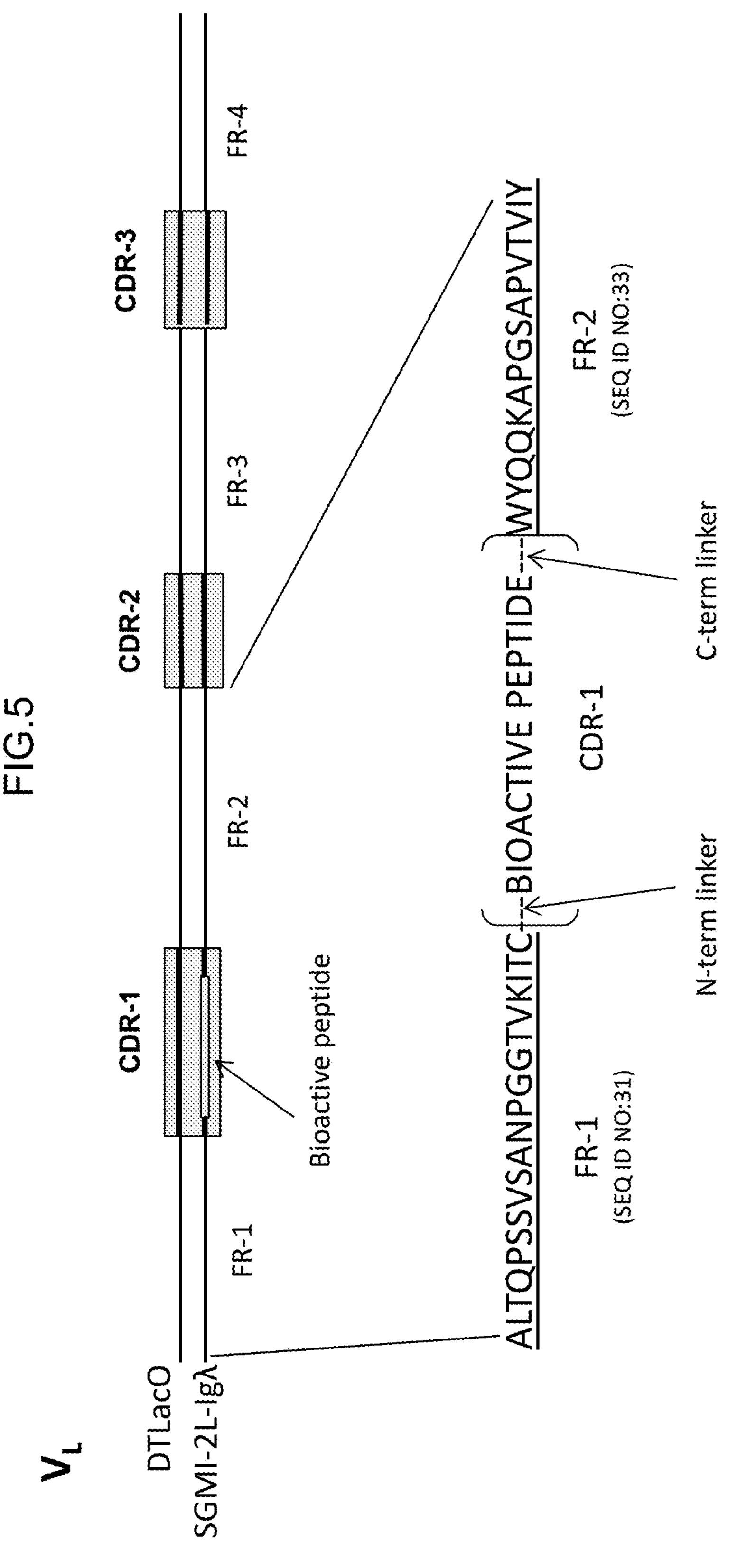
FIG. 5 illustrates an exemplary parental (DTLacO) variable light chain polypeptide sequence compared to a variable light chain polypeptide sequence comprising a bioactive peptide engrafted within CDR-1.
Figure 6:
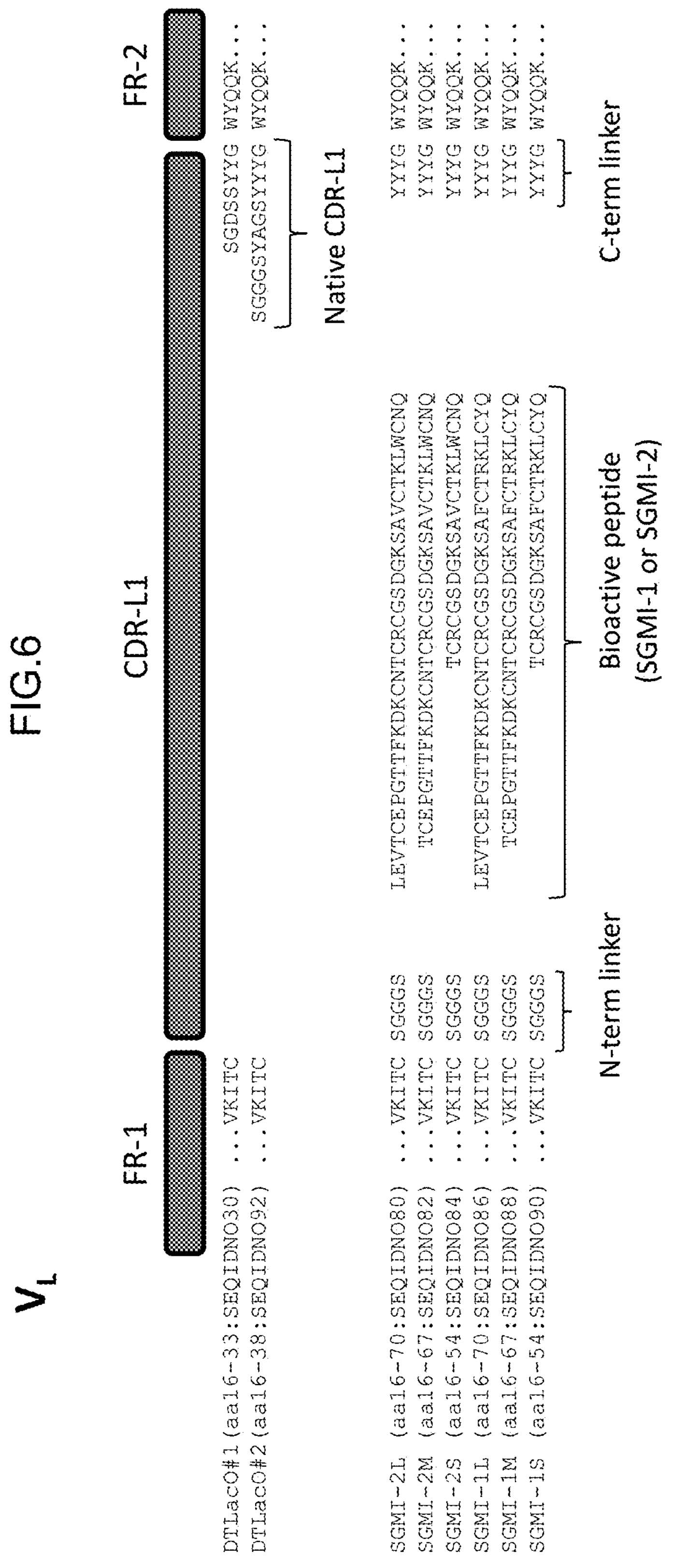
FIG. 6 shows an alignment of the amino acid sequences of exemplary variable light chain polypeptides comprising the bioactive peptide SGMI-1 or SGMI-2, and variants thereof, engrafted within CDR-1, including optional linkers at the C-terminus and/or N-terminus of the bioactive peptide.

As shown in FIGS. 3-6, in some embodiments, at least one peptide linker sequence (typically from 1 amino acid residue to 20 amino acid residues in length) is included between the CDR-engrafted bioactive peptide amino acid sequence and one or both of the chicken framework region(s) adjacent the bioactive peptide-bearing antibody. The peptide linker may be any flexible linker sequence, such a sequence shown in TABLE 4. In some embodiments, as illustrated in FIGS. 4 and 6, native CDR amino acid residues from the parental antibody are used to form a linker on one or both flanking regions of the bioactive peptide adjacent the framework regions. In some embodiments, at least one amino acid, or at least two, at least three, at least four, at least five, or more, up to all the amino acid residues of the native CDR sequence are retained as linker sequences flanking the bioactive peptide in the heavy or light chain variable region comprising the engrafted bioactive peptide.

In some embodiments, the bioactive peptide sequence is engrafted into a heavy chain variable region of an antibody, wherein the heavy chain variable region comprises a region having general formula (I):

N-X-B-Y-C (I) wherein:

N is an amino terminal region of the heavy chain variable region,

X is a flexible amino acid linker region and consists of 0, 1, 2, 3, 4, 5, 6, 7, 8, 9, 10, 11, 12, 13, 14, 15, 16, 17, 18, 19 or 20 amino acids;

B is a bioactive peptide amino acid sequence and consists of an amino acid sequence of no more than 60, or consists of no more than 50 amino acid residues to a minimum of at least 3 amino acid residues;

Y is a flexible amino acid linker region and consists of 0, 1, 2, 3, 4, 5, 6, 7, 8, 9, 10, 11, 12, 13, 14, 15, 16, 17, 18, 19 or 20 amino acids; and C is a carboxy terminal region of the heavy chain variable region, and wherein at least one of the following applies:

N comprises FR-1, set forth as SEQ ID NO:24, or a variant thereof, and C comprises FR-2, set forth as SEQ ID NO:25, or a variant thereof; or N comprises FR-2, set forth as SEQ ID NO:25, or a variant thereof, and C comprises FR-3, set forth as SEQ ID NO:26, or a variant thereof; or N comprises FR-3, set forth as SEQ ID NO:26, or a variant thereof, or flanking SEQ ID NO:27, and C comprises FR-4, set forth as SEQ ID NO:28, or a variant thereof, or flanking SEQ ID NO:29.

In one embodiment, a bioactive peptide sequence is engrafted into a heavy chain variable region of an antibody, wherein N comprises FR-3, set forth as SEQ ID NO:26, or a variant thereof, or flanking SEQ ID NO:27, and C comprises FR-4, set forth as SEQ ID NO:28, or a variant thereof, or flanking SEQ ID NO:29.

In one embodiment, the heavy chain comprising one or more chicken framework regions (VH-FR1, VH-FR2, VH-FR3, VH-FR4) and at least one bioactive peptide engrafted into a CDR further comprises the human IgG1 constant region, set forth as SEQ ID O: 47, or a variant thereof.

In some embodiments, the bioactive peptide sequence is engrafted into a light chain variable region of an antibody, wherein the light chain variable region comprises a region having general formula (II):

N-X-B-Y-C (II) wherein:

N is an amino terminal region of the light chain variable region,

X is a flexible amino acid linker region and consists of 0, 1, 2, 3, 4, 5, 6, 7, 8, 9, 10, 11, 12, 13, 14, 15, 16, 17, 18, 19 or 20 amino acids;

B is a bioactive peptide amino acid sequence and consists of an amino acid sequence of no more than 60, or consists of no more than 50 amino acid residues to a minimum of at least 3 amino acid residues;

Y is a flexible amino acid linker region and consists of 0, 1, 2, 3, 4, 5, 6, 7, 8, 9, 10, 11, 12, 13, 14, 15, 16, 17, 18, 19 or 20 amino acids; and C is a carboxy terminal region of the light chain variable region, and wherein at least one of the following applies:

N comprises FR-1, set forth as SEQ ID NO:31, or a variant thereof, or flanking SEQ ID NO:32, and C comprises FR-2, set forth as SEQ ID NO:33, or a variant thereof, or flanking SEQ ID NO:34; or N comprises FR-2, set forth as SEQ ID NO:33, or a variant thereof, and C comprises FR-3, set forth as SEQ ID NO:35, or a variant thereof; or N comprises FR-3, set forth as SEQ ID NO:35, or a variant thereof, and C comprises FR-4, set forth as SEQ ID NO:36, or a variant thereof.

In one embodiment, a bioactive peptide is engrafted into a light chain variable region of an antibody, wherein N comprises FR-1, set forth as SEQ ID NO:31, or a variant thereof, or flanking SEQ ID NO:32, and C comprises FR-2, set forth as SEQ ID NO:33, or a variant thereof, or flanking SEQ ID NO:34.

In one embodiment, the light chain comprising one or more chicken framework regions (VL-FR1, VL-FR2, VL-FR3, VL-FR4) and at least one bioactive peptide engrafted into a CDR further comprises the human lambda light chain, set forth as SEQ ID NO:48, or a variant thereof.

In one embodiment, the methods according to this aspect of the invention comprise engrafting a bioactive peptide comprising an SGMI core amino acid sequence into at least one of the heavy chain variable region and/or light chain variable region comprising chicken framework regions, wherein the SGMI core amino acid sequence comprises:

(SEQ ID NO: 5)

$X_1CTX_2X_3X_4CX_5Q$ wherein:

$X_1$ is F or V, $X_2$ is R or K, $X_3$ is K or L, $X_4$ is L or W, and $X_5$ is Y or N; and wherein the bioactive peptide inhibits the activity of at least one of MASP-1 or MASP-2.

In one embodiment, the method comprises engrafting a bioactive peptide selected from the group consisting of SEQ ID NO:6 to SEQ ID NO:11.

In one embodiment, the method comprises engrafting a bioactive peptide that inhibits the activity of MASP-1, wherein the bioactive peptide is at least one of SEQ ID NO: 6 to 8.

In one embodiment, the method comprises engrafting a bioactive peptide that inhibits the activity of MASP-2, wherein the bioactive peptide is at least one of SEQ ID NO: 9 to 11.

In another aspect, the present invention provides an isolated antibody, or antigen-binding fragment thereof, comprising one or more bioactive peptide amino acid sequence(s), wherein at least one of the bioactive peptide amino acid sequence is engrafted into at least one of: (i) a light chain variable region comprising chicken framework regions and/or (ii) a heavy chain variable region comprising chicken framework regions. In some embodiments, the bioactive peptide amino acid sequence is engrafted into at least one of CDR-H1, CDR-H2 or CDR-H3 of the heavy chain variable region. In some embodiments, the bioactive peptide amino acid sequence is engrafted into at least one of CDR-L1, CDR-L2 or CDR-L3 of the light chain variable region. Various embodiments of the isolated antibodies or antigen-binding fragments thereof comprising the one or more bioactive peptide amino acid sequences engrafted into one or more CDR regions of a heavy and/or light chain are generated according to the methods as described herein.

In one embodiment, the isolated antibody or antigen binding fragment thereof comprises a bioactive peptide amino acid sequence comprising an SGMI core sequence set forth as SEQ ID NO:5. In one embodiment, the isolated antibody or fragment thereof comprises a bioactive peptide sequence engrafted into a CDR, wherein the bioactive peptide sequence comprises or consists of at least one of SEQ ID NO:6 to SEQ ID NO:11. In one embodiment, the isolated antibody or antigen binding fragment thereof comprises at least one of SEQ ID NO:50, 52, 54, 56, 58, 60, 62, 64, 66, 68, 70, 72, 74, 76, 78, 80, 82, 84, 86, 88, or SEQ ID NO:90, or a variant thereof having at least 85%, or at least 88%, or at least 90%, or at least 92%, or at least 95%, or at least 98% identity to SEQ ID NO:50, 52, 54, 56, 58, 60, 62, 64, 66, 68, 70, 72, 74, 76, 78, 80, 82, 84, 86, 88, or SEQ ID NO:90. In another embodiment, a nucleic acid molecule is provided that encodes the isolated antibody or antigen fragment thereof, the nucleic acid molecule comprising at least one of SEQ ID NO:49, 51, 53, 55, 57, 59, 61, 63, 65, 67, 69, 71, 73, 75, 77, 79, 81, 83, 85, 87 or SEQ ID NO:89, or a variant thereof having at least 85%, or at least 88%, or at least 90%, or at least 92%, or at least 95%, or at least 98% identity to SEQ ID NO:49, 51, 53, 55, 57, 59, 61, 63, 65, 67, 69, 71, 73, 75, 77, 79, 81, 83, 85, 87 or SEQ ID NO:89.

In another aspect, the invention provides a method of making a bioactive peptide-bearing antibody, comprising (a) fusing the amino acid sequence of at least one bioactive peptide of interest onto: (i) an amino terminal region of at least one of: a light chain variable region comprising chicken framework regions and/or a heavy chain variable region comprising chicken framework regions, and/or (ii) a carboxy terminal region of at least one of: a light chain constant region and/or a heavy chain constant region; and (b) determining whether the antibody has substantially the same biological activity as the bioactive peptide.

The methods of this aspect of the invention may be carried out with any bioactive peptide of interest, such as the exemplary bioactive peptides described herein. FIG. 9 is a schematic diagram illustrating the various embodiments of bioactive-peptide bearing antibodies that may be generated using the methods of this aspect of the invention, as further described in Example 4.

In some embodiments, the method according to this aspect of the invention comprises fusing the amino acid sequence of a bioactive peptide of interest to the amino terminal region of at least one of a light chain variable region comprising chicken framework regions and/or a heavy chain variable region comprising chicken framework regions.

In some embodiments, the method according to this aspect of the invention comprises fusing the amino acid sequence of a bioactive peptide of interest to the carboxy terminal region of at least one of: a light chain constant region and/or a heavy chain constant region.

As shown in FIG. 9, in some embodiments, at least one peptide linker sequence (typically from 1 amino acid residue to 20 amino acid residues) is included between the bioactive peptide sequence and the amino terminus of the light or heavy chain region, or between the bioactive peptide sequence and the carboxy terminus of the light or heavy constant region.

In some embodiments, a bioactive peptide of interest is fused to the amino terminus of a heavy chain variable region comprising the VH-FR1, VH-FR-2, VH-FR-3 and VH-FR-4 amino acid sequences set forth as SEQ ID NO:24, 25, 26 and 28, respectively, or variants thereof. In some embodiments, the heavy chain further comprises a human IgG1 constant region, for example, as set forth as SEQ ID NO:47, or a variant thereof.

In some embodiments, a bioactive peptide of interest is fused to the carboxy terminus of a heavy chain constant region, wherein the heavy chain further comprises a variable region comprising the VH-FR1, VH-FR-2, VH-FR-3 and VH-FR-4 amino acid sequences set forth as SEQ ID NO:24, 25, 26 and 28, respectively, or variants thereof.

In some embodiments, a bioactive peptide of interest is fused to the amino terminus of a light chain variable region comprising the VL-FR1, VL-FR2, VL-FR3, VL-FR4 amino acid sequences set forth as SEQ ID NO:31, 33, 35 and 36, respectively, or variants thereof. In some embodiments, the light chain further comprises a human lambda light chain constant region, for example, as set forth as SEQ ID NO:48.

In one embodiment, the methods according to this aspect of the invention comprise fusing a bioactive peptide comprising an SGMI core amino acid sequence onto at least one of a heavy and/or light chain comprising chicken framework regions, wherein the SGMI core amino acid sequence comprises:

(SEQ ID NO: 5)

$$X_1CTX_2X_3X_4CX_5Q$$

wherein:

$X_1$ is F or V, $X_2$ is R or K, $X_3$ is K or L, $X_4$ is L or W, and $X_5$ is Y or N; and wherein the bioactive peptide inhibits the activity of at least one of MASP-1 or MASP-2.

In one embodiment, the method comprises fusing a bioactive peptide selected from the group consisting of SEQ ID NO:6 to SEQ ID NO:11.

In one embodiment, the method comprises fusing a bioactive peptide that inhibits the activity of MASP-1, wherein the bioactive peptide is at least one of SEQ ID NO: 6 to 8.

In one embodiment, the method comprises fusing a bioactive peptide that inhibits the activity of MASP-2, wherein the bioactive peptide is at least one of SEQ ID NO:9 to 11.

In another aspect, the invention provides an isolated antibody, or antigen-binding fragment thereof, comprising one or more bioactive peptide amino acid sequence(s), wherein at least one bioactive peptide amino acid sequence is fused to at least one of (i) the amino terminal region of at least one of: a light chain variable region comprising chicken framework regions and/or a heavy chain variable region comprising chicken framework regions; or (ii) the carboxy terminal region of at least one of: a light chain constant region and/or a heavy chain constant region, wherein the antibody has substantially the same biological activity as the bioactive peptide. Various embodiments of the isolated antibodies or fragments thereof comprising the one or more bioactive peptide amino acids fused to the amino terminal region of a light or heavy chain variable region, or fused to the carboxy terminal region of a light chain constant region or a heavy chain constant region are generated according to the methods as described herein.

In one embodiment, the isolated antibody or antigen binding fragment thereof comprises a bioactive peptide amino acid sequence comprising an SGMI core sequence set forth as SEQ ID NO:5. In one embodiment, the isolated antibody or fragment thereof comprises a bioactive peptide fused onto the amino terminal region of a light or heavy chain variable region, or fused to the carboxy terminal region of a light chain constant region or a heavy chain constant region, wherein the bioactive peptide sequence comprises or consists of at least one of SEQ ID NO:6 to SEQ ID NO:11. In one embodiment, the isolated antibody or antigen binding fragment thereof comprises at least one of SEQ ID NO:94, 96, 98, 100, 102, 104, 106, or SEQ ID NO:108, or a variant thereof having at least 85%, or at least 88%, or at least 90%, or at least 92%, or at least 95%, or at least 98% identity to SEQ ID NO:94, 96, 98, 100, 102, 104, 106, or SEQ ID NO:108. In another embodiment, a nucleic acid molecule is provided that encodes the isolated antibody or antigen fragment thereof, the nucleic acid molecule comprising at least one of SEQ ID NO:93, 95, 97, 99, 101, 103, 105 or SEQ ID NO:107, or a variant thereof having at least 85%, or at least 88%, or at least 90%, or at least 92%, or at least 95%, or at least 98% identity to SEQ ID NO:93, 95, 97, 99, 101, 103, 105 or SEQ ID NO:107.

In another aspect, the invention provides an isolated polypeptide comprising: (i) a region comprising an SGMI core sequence, the SGMI core sequence comprising an amino acid sequence according to: $X_1CTX_2X_3X_4CX_5Q$ (SEQ ID NO:5), wherein: $X_1$ is F or V, $X_2$ is R or K, $X_3$ is K or L, $X_4$ is L or W, and $X_5$ is Y or N; and (ii) a region comprising human IgG1 Fc, wherein the polypeptide inhibits the activity of at least one of MASP-1 or MASP-2.

In one embodiment, the region comprising the human IgG1 Fc region is located at the amino terminus of the region comprising the SGMI core sequence. In another embodiment, the region comprising the human IgG1 Fc region is located at the carboxy terminus of the region comprising the SGMI core sequence.

In one embodiment, the region comprising the IgG1 Fc comprises or consists of SEQ ID NO:12, or a variant thereof.

In one embodiment, the region comprising the SGMI core sequence comprises or consists of at least one of SEQ ID NO:6 to SEQ ID NO:11. In one embodiment, the region comprising human IgG1 Fc is fused directly to at least one of SEQ ID NO:6 to SEQ ID NO:11. In one embodiment, the polypeptide further comprises a linker region of from 1 amino acid residue to 20 amino acid residues, wherein the linker region is included between the region comprising the SGMI core sequence and the region comprising human IgG1 Fc. In one embodiment, the linker sequence comprises at least one of SEQ ID NO:13 or SEQ ID NO:14. In one embodiment, the polypeptide comprises at least one of SEQ ID NO:16 or SEQ ID NO:18, or a variant thereof having at least 85%, or at least 88%, or at least 90%, or at least 92%, or at least 95%, or at least 98% identity to SEQ ID NO:16 or SEQ ID NO:18.

In another embodiment, a nucleic acid molecule is provided that encodes the polypeptide, the nucleic acid molecule comprising at least one of SEQ ID NO:15 or SEQ ID NO:17, or a variant thereof having at least 85%, or at least 88%, or at least 90%, or at least 92%, or at least 95%, or at least 98% identity to SEQ ID NO:15 or SEQ ID NO:17.

Methods for Producing Antibodies

The antibodies and polypeptides of the invention can be produced by standard recombinant genetic engineering methods, which are well known to those of skill in the art of molecular biology and immunology.

For recombinant production of a fusion polypeptide of the invention, DNA sequences encoding the polypeptide components of a fusion polypeptide (e.g., a bioactive peptide sequence and a heavy chain or light chain polypeptide sequence of interest) may be assembled using conventional methodologies. In one example, the components may be assembled separately and ligated into an appropriate expression vector. For example, the 3' end of the DNA sequence encoding one polypeptide component is ligated, with or without a peptide linker, to the 5' end of a DNA sequence encoding the second polypeptide component so that the reading frames of the sequences are in phase.

For recombinant production of a bioactive peptide sequence engrafted into a CDR region of a heavy chain variable region or a light chain variable region, the nucleic acid components may be assembled and ligated into an appropriate expression vector, with or without a peptide linker, such that the nucleic acid sequence encoding the bioactive peptide sequence is in phase with the nucleic acid sequence encoding the adjacent framework regions of the variable light chain or variable heavy chain.

As described herein, a peptide linker sequence may be employed to separate a bioactive peptide sequence from a heterologous polypeptide sequence by some defined distance, for example a distance sufficient to ensure that the advantages of the invention are achieved, e.g., biological activity of the bioactive peptide engrafted into a CDR region, or fused onto an amino or carboxy terminal region of a heavy or light chain polypeptide. Such a peptide linker sequence may be incorporated into the bioactive peptide-bearing antibodies using standard techniques well known in the art. Suitable peptide linker sequences may be chosen based, for example, on the factors such as: (1) their ability to adopt a flexible extended conformation; and (2) their inability to adopt a secondary structure that could interfere with the activity of the bioactive peptide sequence. Illustrative peptide linker sequences, for example, may contain Gly, Asn and Ser residues. Other near neutral amino acids, such as Thr and Ala may also be used in the linker sequence. Amino acid sequences which may be usefully employed as linkers include those disclosed herein as well as those disclosed in Maratea et al., Gene 40:39-46, 1985; Murphy et al., Proc. Natl. Acad. Sci. USA 83:8258-8262, 1986; U.S. Pat. Nos. 4,935,233 and 4,751,180. The linker sequence may generally be from 1 to about 20 amino acids in length, for example.

The invention further includes nucleic acid molecules encoding the polypeptides of the invention as described herein. A vector that contains such a nucleic acid is also included. When the method is performed in a host cell, the host cell is first transformed or transfected with an exogenous nucleic acid encoding the stabilized polypeptide, then the polypeptides and antibodies are expressed and recovered. The host cells can be prokaryotic, such as bacteria, or eukaryotic, as described further herein.

In many embodiments, the nucleic acids encoding a subject monoclonal antibody are introduced directly into a host cell, and the cell incubated under conditions sufficient to induce expression of the encoded antibody.

In some embodiments, the invention provides a cell comprising a nucleic acid molecule encoding an antibody or polypeptide of the invention.

In some embodiments, the invention provides an expression cassette comprising a nucleic acid molecule encoding an antibody or polypeptide of the invention.

In some embodiments, the invention provides a method of producing an antibody or polypeptide of the invention comprising culturing a cell comprising a nucleic acid molecule encoding an antibody of the invention.

According to certain related embodiments there is provided a recombinant host cell which comprises one or more constructs as described herein; a nucleic acid encoding any antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

For example, any cell suitable for expression of expression cassettes may be used as a host cell, for example, yeast, insect, plant, etc., cells. In many embodiments, a mammalian host cell line that does not ordinarily produce antibodies is used, examples of which are as follows: monkey kidney cells (COS cells), monkey kidney CVI cells transformed by SV40 (COS-7, ATCC CRL 165 1); human embryonic kidney cells (HEK-293, Graham et al., *J. Gen Virol.* 36:59 (1977)); baby hamster kidney cells (BHK, ATCC CCL 10); Chinese hamster ovary-cells (CHO, Urlaub and Chasin, *Proc. Natl. Acad. Sci.* (USA) 77:4216, (1980); mouse sertoli cells (TM4, Mather, *Biol. Reprod.* 23:243-251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., *Annals N.Y. Acad. Sci* 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209.

Methods of introducing nucleic acids into cells are well known in the art. Suitable methods include electroporation, particle gun technology, calcium phosphate precipitation, cationic lipid nucleic acid delivery, direct microinjection, and the like. The choice of method is generally dependent on the type of cell being transformed and the circumstances under which the transformation is taking place (i.e., in vitro, ex vivo, or in vivo). A general discussion of these methods can be found in Ausubel, et al., Short Protocols in Molecular Biology, 3d ed., Wiley & Sons, 1995. In some embodiments, lipofectamine and calcium mediated gene transfer technologies are used.

After the subject nucleic acids have been introduced into a cell, the cell is typically incubated, normally at 37° C., sometimes under selection, for a suitable time to allow for the expression of the antibody. In most embodiments, the antibody is typically secreted into the supernatant of the media in which the cell is growing in.

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359 (1984)). The efficiency of expression may be enhanced by the inclusion of appropriate transcription enhancer elements, transcription terminators, etc. (see Bittner et al., *Methods in Enzymol.* 153:51-544 (1987)).

For long-term, high-yield production of recombinant antibodies, stable expression may be used. For example, cell lines, which stably express the antibody molecule, may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium. For example, a nucleic acid sequence encoding a signal peptide may be included adjacent the coding region of the antibody or fragment. Such a signal peptide may be incorporated adjacent to the 5' end of the amino acid sequences set forth herein for the subject antibodies in order to facilitate production of the subject antibodies.

In one embodiment, the antibodies according to certain embodiments of the present invention may be generated using an in vitro system based on the DT40 chicken B cell lymphoma line. The DT40 chicken B cell lymphoma line has been used for antibody evolution ex vivo (Cumbers, S. J. et al. *Nat Biotechnol* 20:1129-1134 (2002); Seo, H. et al. *Nat Biotechnol* 23:731-735 (2005).). DT40 cells command enormous potential V region sequence diversity, as they can access two distinct physiological pathways for diversification, gene conversion and somatic hypermutation, which create templated and nontemplated mutations, respectively (Maizels, N., Immunoglobulin gene diversification. *Ann. Rev. Genet.* 39:23-46 (2005)). However, the utility of DT40 cells for antibody evolution has been limited in practice because—as in other transformed B cell lines—diversification occurs at less than 1% the physiological rate. Diversification can be accelerated several-fold by disabling the homologous recombination pathway (Cumbers et al., supra), but cells thus engineered lose the ability to carry out efficient gene targeting. Diversification can also be accelerated by treatment of cells with the histone deacetylase inhibitor, trichostatin A (Seo et al., supra), but resulting mutations are exclusively templated, which limits potential diversity and may not produce antibodies of required affinity or specificity.

The DT40 cells used herein to generate antibodies are modified to accelerate the rate of immunoglobulin (Ig) gene diversification without sacrificing the capacity for further genetic modification or the potential for both gene conversion and somatic hypermutation to contribute to mutagenesis. This was accomplished by putting Ig gene diversification under control of the potent *E. coli* lactose operator/repressor regulatory network. Multimers consisting of approximately 100 polymerized repeats of the potent *E. coli* lactose operator (PolyLacO) were inserted upstream of the rearranged and expressed Igλ and IgH genes by homologous gene targeting. Regulatory factors fused to lactose repressor protein (LacI) can then be tethered to the LacO regulatory elements to regulate diversification, taking advantage of the high affinity ($K_D=10^{-14}$M) of lactose repressor for operator DNA. DT40 PolyLacO-$\lambda_R$ cells, in which PolyLacO was integrated only at Igλ, exhibited a 5-fold increase in Ig gene diversification rate relative to the parental DT40 cells prior to any engineering (Cummings, W. J. et al. *PLoS Biol* 5, e246 (2007)). Diversification was further elevated in cells engineered to carry PolyLacO targeted to both the Igλ and the IgH genes ("DTLacO").

Pharmaceutical Compositions

In another aspect, the invention provides pharmaceutical compositions comprising the bioactive peptide-bearing antibodies and fragments thereof, as disclosed herein and a pharmaceutically acceptable carrier. In some embodiments, the invention provides compositions comprising bioactive peptide-bearing antibodies and fragments thereof capable of inhibiting activation of the lectin complement pathway. The carrier is non-toxic, biocompatible and is selected so as not to detrimentally affect the biological activity of the bioactive peptide-bearing antibody (and any other therapeutic agents combined therewith). Exemplary pharmaceutically acceptable carriers for polypeptides are described in U.S. Pat. No. 5,211,657 to Yamada. The bioactive peptide-bearing antibodies and polypeptides may be formulated into preparations in solid, semi-solid, gel, liquid or gaseous forms such as tablets, capsules, powders, granules, ointments, solutions, depositories, inhalants and injections allowing for oral, parenteral or surgical administration. The invention also contemplates local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose, any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting example, microparticles, microspheres, nanospheres or nanoparticles composed of proteins, liposomes, carbohydrates, synthetic organic compounds, inorganic compounds, polymeric or copolymeric hydrogels and polymeric micelles. Suitable hydrogel and micelle delivery systems include the PEO:PHB:PEO copolymers and copolymer/cyclodextrin complexes disclosed in WO 2004/009664 A2 and the PEO and PEO/cyclodextrin complexes disclosed in U.S. Patent Application Publication No. 2002/0019369 A1. Such hydrogels may be injected locally at the site of intended action, or subcutaneously or intramuscularly to form a sustained release depot.

For intra-articular or intravenous delivery, the bioactive peptide-bearing antibodies or polypeptides may be carried in above-described liquid or gel carriers that are injectable, above-described sustained-release delivery vehicles that are injectable, or a hyaluronic acid or hyaluronic acid derivative.

For intrathecal (IT) or intracerebroventricular (ICV) delivery, appropriately sterile delivery systems (e.g., liquids; gels, suspensions, etc.) can be used to administer the present invention.

The compositions of the present invention may also include biocompatible excipients, such as dispersing or wetting agents, suspending agents, diluents, buffers, penetration enhancers, emulsifiers, binders, thickeners, flavoring agents (for oral administration).

To achieve high concentrations of the subject antibodies for local delivery, the antibodies may be formulated as a suspension of particulates or crystals in solution for subsequent injection, such as for intramuscular injection of a depot.

Therapeutic Methods:

In another aspect, the invention provides methods of inhibiting lectin pathway complement activation in a mammalian subject, such as a human subject, comprising administering a composition comprising a bioactive peptide-bearing antibody or polypeptide as disclosed herein to said human subject, wherein the bioactive peptide inhibits activation of the lectin complement pathway. As described herein, the bioactive peptides SGMI-1 and SGMI-2 block the lectin pathway of complement activation without affecting the classical or alternative pathways (Heja et al., 2012. *Proc. Natl. Acad. Sci.* 109:10498). As described in U.S. Pat. No. 7,919,094, co-pending U.S. patent application Ser. No. 13/083,441, and co-pending U.S. patent application Ser. No. 12/905,972 (each of which is assigned to Omeros Corporation, the assignee of the instant application), each of which is hereby incorporated by reference, MASP-2 dependent lectin complement activation has been implicated as contributing to the pathogenesis of numerous acute and chronic disease states, including MASP-2-dependent complement mediated vascular condition, an ischemia reperfusion injury, atherosclerosis, inflammatory gastrointestinal disorder, a pulmonary condition, an extracorporeal reperfusion procedure, a musculoskeletal condition, a renal condition, a skin condition, organ or tissue transplant, nervous system disorder or injury, a blood disorder, a urogenital condition, diabetes, chemotherapy or radiation therapy, malignancy, an endocrine disorder, a coagulation disorder, a thrombotic microangiopathy, or an ophthalmologic condition. Therefore, the lectin pathway inhibitory antibodies of the present invention may be used to treat the above-referenced diseases and conditions.

In one embodiment, the composition is formulated to specifically inhibit MASP-1 or MASP-2 activity. In one embodiment, the composition is formulated to inhibit MASP-1 activity. In one embodiment, the composition is formulated to inhibit MASP-2 activity.

In one embodiment, the composition is formulated for systemic delivery, such as, by intra-arterial, intravenous, intracranial, intramuscular, inhalational, nasal or subcutaneous administration.

As used herein, the terms "systemic delivery" and "systemic administration" are intended to include but are not limited to oral and parenteral routes including intramuscular (IM), subcutaneous, intravenous (IV), intra-arterial, inhalational, sublingual, buccal, topical, transdermal, nasal, rectal, vaginal and other routes of administration that effectively result in dispersal of the delivered antibody to a single or multiple sites of intended therapeutic action. Preferred routes of systemic delivery for the present compositions include intravenous, intramuscular, subcutaneous, and inhalational. It will be appreciated that the exact systemic administration route for selected agents utilized in particular compositions of the present invention will be determined in part to account for the agent's susceptibility to metabolic transformation pathways associated with a given route of administration.

The bioactive peptide-bearing antibodies and polypeptides can be delivered into a subject in need thereof by any suitable means. Methods of delivery include administration by oral, pulmonary, parenteral (e.g., intramuscular, intraperitoneal, intravenous (IV), or subcutaneous injection), inhalation (such as via a fine powder formulation), transdermal, nasal, vaginal, rectal, or sublingual routes of administration, and can be formulated in dosage forms appropriate for each route of administration.

The compositions of the present invention may be systemically administered on a periodic basis at intervals determined to maintain a desired level of therapeutic effect. For example, compositions may be administered, such as by subcutaneous injection, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. The dosage for each individual agent will vary as a function of the particular antibody that is included in the composition, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s).

Therapeutic efficacy of MASP-2 and MASP-1 inhibitory compositions and methods of the present invention in a given subject, and appropriate dosages, can be determined in accordance with complement assays well known to those of skill in the art. Complement generates numerous specific products. During the last decade, sensitive and specific assays have been developed and are available commercially for most of these activation products, including the small activation fragments C3a, C4a, and C5a and the large activation fragments iC3b, C4d, Bb, and sC5b-9. Most of these assays utilize antibodies that react with new antigens (neoantigens) exposed on the fragment, but not on the native proteins from which they are formed, making these assays very simple and specific. Most rely on ELISA technology, although radioimmunoassay is still sometimes used for C3a and C5a. These latter assays measure both the unprocessed fragments and their 'desArg' fragments, which are the major forms found in the circulation. Unprocessed fragments and $C5a_{desArg}$ are rapidly cleared by binding to cell surface receptors and are hence present in very low concentrations, whereas $C3a_{desArg}$ does not bind to cells and accumulates in plasma. Measurement of C3a provides a sensitive, pathway-independent indicator of complement activation. Alternative pathway activation can be assessed by measuring the Bb fragment. Detection of the fluid-phase product of membrane attack pathway activation, sC5b-9, provides evidence that complement is being activated to completion. Because both the lectin and classical pathways generate the same activation products, C4a and C4d, measurement of these two fragments does not provide any information about which of these two pathways has generated the activation products.

The inhibition of lectin-dependent complement activation is characterized by at least one of the following changes in a component of the complement system that occurs as a result of administration of an anti-MASP-2 antibody in accordance with the present invention: the inhibition of the generation or production of MASP-2-dependent complement activation system products C4b, C3a, C5a and/or C5b-9 (MAC), the reduction of C4 cleavage and C4b deposition, or the reduction of C3 cleavage and C3b deposition.

Articles of Manufacture

In another aspect, the present invention provides an article of manufacture containing a bioactive peptide-bearing antibody, or antigen binding fragment thereof, or polypeptide as described herein in a unit dosage form suitable for therapeutic administration to a human subject, such as, for example, a unit dosage in the range of 1 mg to 5000 mg, such as from 1 mg to 2000 mg, such as from 1 mg to 1000 mg, such as 5 mg, 10 mg, 50 mg, 100 mg, 200 mg, 500 mg, or 1000 mg. In some embodiments, the article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example, the container may be an intravenous solution bag or a vial having a stopper pierceable by a hypodermic injection needle). At least one active agent in the composition is the bioactive peptide-bearing antibody or antigen binding fragment thereof or polypeptide of the invention. The label or package insert indicates that the composition is used for treating the particular condition. The label or package insert will further comprise instructions for administering the antibody composition to the patient. Articles of manufacture and kits comprising combinatorial therapies described herein are also contemplated.

The following examples merely illustrate the best mode now contemplated for practicing the invention, but should not be construed to limit the invention.

Example 1

Overview of the Strategy for Generating Inhibitory MASP Polypeptides by Engrafting Bioactive Peptides into or onto Antibodies, or Fragments Thereof Rationale:

The generation of specific inhibitors of MASP-1 and MASP-2, termed SGMI-1 and SGMI-2, respectively, is described in Heja et al., *J Biol Chem* 287:20290 (2012) and Heja et al., *PNAS* 109:10498 (2012), each of which is hereby incorporated herein by reference. SGMI-1 and SGMI-2 are each 36 amino acid peptides which were selected from a phage library of variants of the *Schistocerca gregaria* protease inhibitor 2 in which six of the eight positions of the protease binding loop were fully randomized. Subsequent in vitro evolution yielded mono-specific inhibitors with single digit nM $K_I$ values (Heja et al., *J. Biol. Chem.* 287:20290, 2012). Structural studies revealed that the optimized protease binding loop forms the primary binding site that defines the specificity of the two inhibitors. The amino acid sequences of the extended secondary and internal binding regions are common to the two inhibitors and contribute to the contact interface (Heja et al., 2012. *J. Biol. Chem.* 287:20290). Mechanistically, both SGMI-1 and SGMI-2 block the lectin pathway of complement activation without affecting the classical or alternative pathways (Heja et al., 2012. *Proc. Natl. Acad. Sci.* 109:10498).

The amino acid sequences of the SGMI-1 and SGMI-2 inhibitors are set forth below:

```
SGMI-1-full-length:
                                    (SEQ ID NO: 6)
LEVTCEPGTTFKDKCNTCRCGSDGKSAFCTRKLCYQ

SGMI-1-medium:
                                    (SEQ ID NO: 7)
   TCEPGTTFKDKCNTCRCGSDGKSAFCTRKLCYQ

SGMI-1-short:
                                    (SEQ ID NO: 8)
                TCRCGSDGKSAFCTRKLCYQ
```

-continued

SGMI-2-full-length:

(SEQ ID NO: 9)
LEVTCEPGTTFKDKCNTCRCGSDGKSAVCTKLWCNQ

SGMI-2-medium:

(SEQ ID NO: 10)
TCEPGTTFKDKCNTCRCGSDGKSAVCTKLWCNQ

SGMI-2-short:

(SEQ ID NO: 11)
................TCRCGSDGKSAVCTKLWCNQ

The above SGMI sequences share a core SGMI sequence (underlined), which is set forth below as SEQ ID NO:5:

(SEQ ID NO: 5)
$X_1CTX_2X_3X_4CX_5Q$ wherein:

$X_1$ is F or V, $X_2$ is R or K, $X_3$ is K or L, $X_4$ is L or W, and $X_5$ is Y or N The bioactive peptides derived from SGMI-1 (set forth as SEQ ID NOs:6-8) and SGMI-2 (set forth as SEQ ID NO:9-11) are highly specific inhibitors of MASP-1 and MASP-2, respectively. However, as peptides they have limited potential for use in biological studies and therapeutic applications. To address these limitations, we engrafted these bioactive peptide amino acid sequences (i.e., amino acid sequences encoding the bioactive peptides) into three distinct scaffolds: (1) onto the amino terminus of human IgG1 Fc region to create an Fc-fusion protein, as described in Example 2; (2) into selected CDRs of a chimeric chicken (variable regions)—human (IgG1 and Igλ constant regions) antibody, as described in Example 3; and (3) onto the amino or carboxy termini of the heavy and/or light chains of an antibody, as described in Example 4.

As described herein, introduction of a bioactive peptide sequence into an antibody scaffold results in a product with the bioactivity of the bioactive peptide and with improved therapeutic properties, such as a longer half-life and antibody effector functions.

Example 2

This Example describes the generation of recombinant SGMI-Fc fusion proteins and demonstrates that these fusion proteins are able to inhibit the lectin pathway.

Methods:

To express the SGMI-IgG1 Fc fusion proteins, polynucleotides encoding the SGMI-1 (SEQ ID NO:6) and SGMI-2 (SEQ ID NO:9) peptides were synthesized (DNA 2.0) and inserted into the expression vector pFUSE-hIgG1-Fc2 (InvivoGen) between nucleotide sequences encoding the IL-2 signal sequence and the human IgG1 Fc region (SEQ ID NO:12). In some embodiments, an optional flexible polypeptide linker (e.g., SEQ ID NO:13 or SEQ ID NO:14) was included between the SGMI peptide and the IgG1 Fc region.

Exemplary Flexible Polypeptide Linker Sequences:

(SEQ ID NO: 13)
GTGGGSGSSSRS (SEQ ID NO: 14)
GTGGGSGSSS

It is noted that in another embodiment, the invention encompasses an alternative version of the SGMI-IgG1 Fc fusion proteins containing the IgG1 Fc region fused to the amino terminus of the SGMI peptides. It is further noted that in further embodiments, the invention encompasses alternative versions of the SGMI-IgG1 Fc fusion proteins comprising a bioactive peptide amino acid sequence comprising the core SGMI sequence (SEQ ID NO:5), and having a length of from at least 9 amino acid residues to 36 amino acid residues, including various truncated versions of SGMI-1 or SGMI-2 bioactive peptides (e.g., SGMI peptides comprising the core sequence of SEQ ID NO:5, such as any of SEQ ID NO:6 to SEQ ID NO:11).

The resulting constructs are described as follows:

A polynucleotide encoding the polypeptide fusion comprising the human IL-2 signal sequence, SGMI-1, linker and human IgG1-Fc (pFUSE-SGMI-1Fc), is set forth as SEQ ID NO:15, which encodes the mature polypeptide fusion comprising SGMI-1 (underlined), linker region (italicized) and human IgG1-Fc (together referred to as "SGMI-1Fc"), which is set forth as SEQ ID NO:16.

SEQ ID NO: 16
LEVTCEPGTTFKDKCNTCRCGSDGKSAFCTRKLCYQ*GTGGGSGSSSRS*DK

THTCPPCPAPELLGGPSVFLEPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNV

FSCSVMHEALHNHYTQKSLSLSPGK

A polynucleotide encoding the polypeptide fusion comprising the human IL-2 signal sequence, SGMI-2, linker and human IgG1-Fc (pFUSE-SGMI-2Fc), is set forth as SEQ ID NO:17, which encodes the mature polypeptide fusion comprising SGMI-2 (underlined), linker region (italicized) and human IgG1-Fc (together referred to as "SGMI-2Fc"), which is set forth as SEQ ID NO:18:

SEQ ID NO: 18
LEVTCEPGTTFKDKCNTCRCGSDGKSAVCTKLWCNQ*GTGGGSGSSSRS*DK

THTCPPCPAPELLGGPSVFLEPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNV

FSCSVMHEALHNHYTQKSLSLSPGK

Production of Recombinant Proteins:

Freestyle™293-F or Expi293F™ cells (Invitrogen) were transiently transfected according to the supplier's protocol with one of the two expression plasmids (pFUSE-SGMI-1Fc (SEQ ID NO:15) and pFUSE-SGMI-2Fc (SEQ ID NO:17). After four days of incubation at 37° C., the culture media were harvested. The Fc-fusion proteins were purified by Protein A affinity chromatography.

Assays Measuring Activation of the Lectin Pathway.

The Wieslab® Complement System Screen (Euro Diagnostic, Malmo, Sweden), MBL assay measures C5b-C9 deposition in conditions that isolated the lectin pathway. The assay was carried out according to the manufacturer's instructions with the Fc fusion proteins being tested at final concentrations of 400 nM.

FIG. 1 is a bar graph showing the inhibitory activity of the SGMI-1Fc (SEQ ID NO:16) or SGMI-2Fc (SEQ ID NO:18) fusion proteins in comparison to the positive and negative sera provided with the assay kit, as well as an isotype control antibody. As shown in FIG. 1, both SGMI-1Fc and SGMI-2Fc inhibit the activation of the lectin pathway, whereas the isotype control antibody does not.

The SGMI-1Fc and SGMI-2Fc fusion proteins were also tested for the ability to inhibit deposition of C3b from 1% serum on a mannan-coated 96-well plate, which is another measure of lectin pathway activity. SGMI-1Fc and SGMI-2Fc were pre-incubated with 1% normal human serum for one hour on ice before addition to wells coated with mannan (2 μg/well). C3b deposition was measured by ELISA as described in Schwaeble et al. PNAS 108:7523, 2011.

Figure 2:
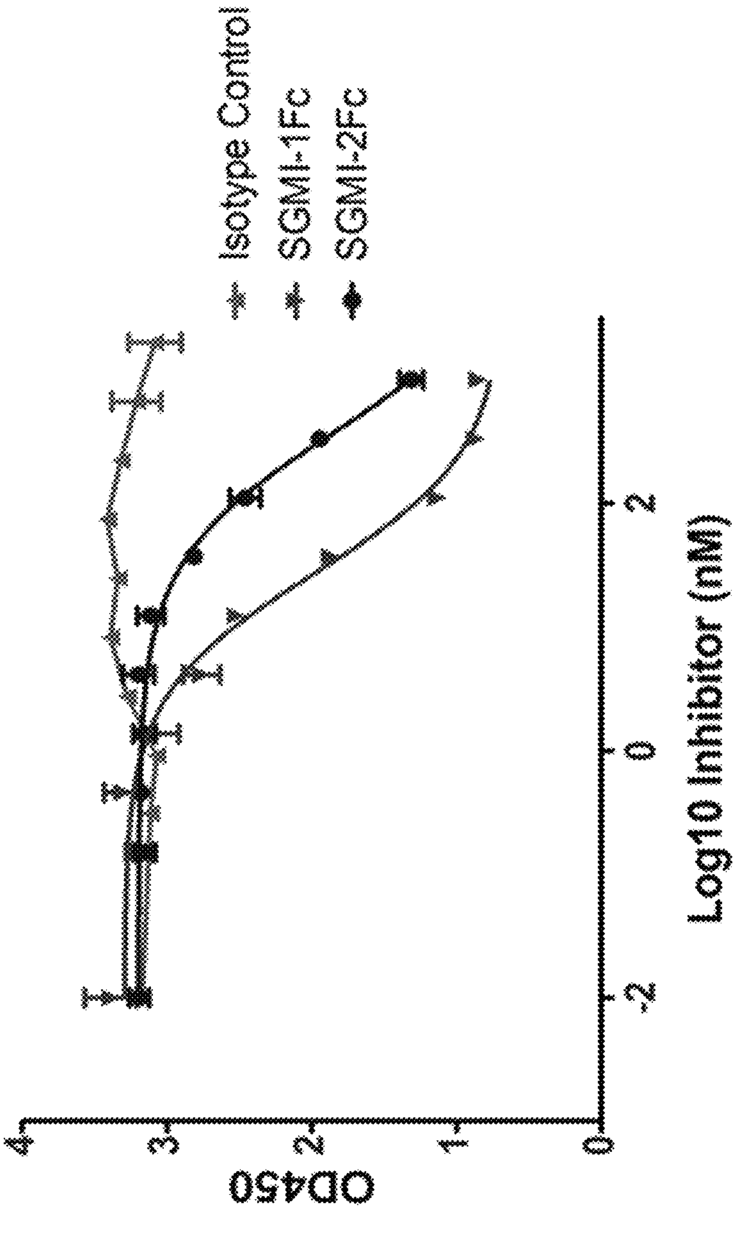
FIG. 2 graphically illustrates the level of C3b deposition for 1% normal serum plus isotype control, SGMI-1Fc or SGMI-2Fc over a concentration range of 0.15 nM to 1000 nM, demonstrating that both SGMI-1Fc and SGMI-2Fc inhibited C3b deposition from normal serum in mannan-coated ELISA wells.

FIG. 2 graphically illustrates the level of C3b deposition for 1% normal human serum plus isotype control, SGMI-1Fc or SGMI-2Fc over a concentration range of 0.15 to 1000 nM. As shown in FIG. 2, both SGMI-1Fc and SGMI-2Fc inhibited C3b deposition from normal serum in mannan-coated ELISA wells, with IC50 values of approximately 27 nM and 300 nM, respectively.

These results demonstrate that the MASP-1 and MASP-2 inhibitory functions of the SGMI peptides are retained in the SGMI-1Fc and SGMI-2Fc fusion proteins.

Example 3

This Example describes the generation of chimeric chicken (V region)/human constant region) antibodies comprising a bioactive peptide amino acid sequence (e.g., SGMI-1 or SGMI-2) engrafted into at least one CDR region of a heavy chain variable region and/or at least one CDR region of a light chain variable region (e.g., CDR-H3 and/or CDR-L1).

Background/Rationale:

A modified DT40 cell line, DTLacO, that permits reversible induction of diversification of a particular polypeptide, is described in WO2009029315 and US2010093033, each of which is hereby incorporated herein by reference. DT40 is a chicken B cell line that is known to constitutively mutate its heavy and light chain immunoglobulin (Ig) genes in culture. Like other B cells, this constitutive mutagenesis targets mutations to the V region of Ig genes, and thus, the CDRs of the expressed antibody molecules. Constitutive mutagenesis in DT40 cells takes place by gene conversion using as donor sequences an array of non-functional V gene segments (pseudo-V genes; ψV) situated upstream of each functional V region. Deletion of the ψV region was previously shown to cause a switch in the mechanism of diversification from gene conversion to somatic hypermutation, the mechanism commonly observed in human B cells. The DT40 chicken B cell lymphoma line has been shown to be a promising starting point for antibody evolution ex vivo (Cumbers, S. J. et al. *Nat Biotechnol* 20, 1129-1134 (2002); Seo, H. et al. *Nat Biotechnol* 23, 731-735 (2005)). DT40 cells proliferate robustly in culture, with an 8-10 hour doubling time (compared to 20-24 hr for human B cell lines), and they support very efficient homologous gene targeting (Buerstedde, J. M. et al. *Embo J* 9, 921-927 (1990)). DT40 cells command enormous potential V region sequence diversity given that they can access two distinct physiological pathways for diversification, gene conversion and somatic hypermutation, which create templated and nontemplated mutations, respectively (Maizels, N. *Annu Rev Genet* 39, 23-46 (2005)). Diversified heavy and light chain immunoglobulins (Igs) are expressed in the form of a cell-surface displayed IgM. Surface IgM has a bivalent form, structurally similar to an IgG molecule. Cells that display IgM with specificity for a particular antigen can be isolated by binding either immobilized soluble or membrane displayed versions of the antigen. However, utility of DT40 cells for antibody evolution has been limited in practice because—as in other transformed B cell lines—diversification occurs at less than 1% the physiological rate.

In the system used in this example, as described in WO2009029315 and US2010093033, the DT40 cells were engineered to accelerate the rate of Ig gene diversification without sacrificing the capacity for further genetic modification or the potential for both gene conversion and somatic hypermutation to contribute to mutagenesis. Two key modifications to DT40 were made to increase the rate of diversification and, consequently, the complexity of binding specificities in the library of cells (Yabuki et al., *PLoS One* 7:e36032, 2012). First, Ig gene diversification was put under the control of the potent *E. coli* lactose operator/repressor regulatory network. Multimers consisting of approximately 100 polymerized repeats of the potent *E. coli* lactose operator (PolyLacO) were inserted upstream of the rearranged and expressed Igλ and IgH genes by homologous gene targeting. Regulatory factors fused to lactose repressor protein (LacI) can then be tethered to the LacO regulatory elements to regulate diversification, taking advantage of the high affinity ($k_D=10^{-14}$M) of lactose repressor for operator DNA. DT40 PolyLacO-$\lambda_R$ cells, in which PolyLacO was integrated only at Igλ, exhibited a 5-fold increase in Ig gene diversification rate relative to the parental DT40 cells prior to any engineering (Cummings, W. J. et al. *PLoS Biol* 5, e246 (2007)). Diversification was further elevated in cells engineered to carry PolyLacO targeted to both the Igλ and the IgH genes ("DTLacO"). DTLacO cells were demonstrated to have diversification rates 2.5- to 9.2-fold elevated relative to the 2.8% characteristic of the parental DT40 PolyLacO-$\lambda_R$ LacI-HP1 line. Thus, targeting PolyLacO elements to both the heavy and light chain genes accelerated diversification 21.7-fold relative to the DT40 parental cell line. Tethering regulatory factors to the Ig loci not only alters the frequency of mutagenesis, but also can change the pathway of mutagenesis creating a larger collection of unique sequence changes (Cummings et al. 2007; Cummings et al. 2008). Second, a diverse collection of sequence starting points for the tethered factor-accelerated Ig gene diversification was generated. These diverse sequence starting points were added to DTLacO by targeting rearranged Ig heavy-chain variable regions, isolated from a two month old chick, to the heavy chain locus. The addition of these heavy chain variable regions created a repertoire of $10^7$ new starting points for antibody diversification. Building these new starting points into the DTLacO cell line permits the identification of clones that bind a particular target, and then enable rapid affinity maturation by the tethered factors. Following affinity maturation, a full-length, recombinant chimeric IgG is made by cloning the matured, rearranged heavy- and light-chain variable sequences (VH and Vλ consisting of chicken framework regions and the CDRs) into expression vectors containing human IgG1 and lambda constant regions. These recombinant mAbs are suitable for in vitro and in vivo applications, and they serve as the starting point for humanization.

Through the use of the DTLacO system, the inventors have observed large inserts of more than 25 amino acids in CDR-H3 of the chicken heavy (VH) and CDR-L1 of the chicken light (VL) chain variable regions. In contrast, the average CDR-H3 size for mice and humans is much smaller (average size of 9 amino acids and 12 amino acids, respectively). Given the potential of these chicken CDRs to accommodate large blocks of sequence, the inventors tested the capacity of the CDRs to present the bioactive peptides SGMI-1 and SGMI-2 in an active conformation. The value of this strategy is several-fold: (1) the in vivo stability of an antibody is conferred to the SGMI-inhibitors, an important benefit for therapeutic applications; (2) integration of the VH and VL genes carrying a bioactive peptide, (such as the SGMI-1 or -2 sequence) into the DTLacO cell line provides the means for ex vivo mutagenesis and selection of V regions with greater affinity and potency; (3) engrafting a first bioactive peptide (e.g. SGMI-1) into one of the long CDRs and engrafting a second bioactive peptide (e.g. SGMI-2) into another of the long CDRs of an antibody, will create a bi-specific antibody that has two functional activities (e.g., inhibits MASP-1 and MASP-2). While this example describes the invention in the context of engrafting SGMI sequences into the CDR-H3 and/or CDR-L1 of the chicken variable regions and retaining inhibitory activity, it will be understood by one of skill in the art that results here establish a paradigm for the display and delivery of other bio-active peptides within CDRs of the variable light and/or heavy chain of antibodies comprising chicken variable regions.

Methods:

To generate the chimeric chicken-human antibodies bearing bioactive peptides (SGMI-1 or SGMI-2) within CDR-H3 and/or CDR-L1, polynucleotides encoding the SGMI-1 and SGMI-2 peptides were inserted by In-Fusion cloning (Clontech primers shown in Table 3) into the pcDNA3 (Invitrogen)-based expression vectors of chicken-human chimeric heavy- and light-chain antibodies, described in WO2009029315 and US2010093033, incorporated herein by reference.

TABLE 3

PCR primers used for cloning the SGMI-1 and SGMI-2 polynucleotides into chicken V-regions, resulting in SGMI-1L-IgG1 and SGMI-2L-Igλ chimeric antibodies.

| Primer | Sequence |
|---|---|
| SGMI-1 Forward | CTACTGCGCCAAACTCGAGGTGACATGTGA (SEQ ID NO: 19) |
| SGMI-1 Reverse | CGTGGCCCCATGCCTGGTAGCACAATTTCC (SEQ ID NO: 20) |
| SGMI-2 Forward | CGGGGGTGGCAGC TTGGAAGTGACGTGTGA (SEQ ID NO: 21) |
| SGMI-2 Reverse | AGCCATAATAGTA CTGGTTACACCAGAGCT (SEQ ID NO: 22) |

1. SGMI-1 and SGMI-2 Engrafted into the CDR-H3 of a Parental Chicken Heavy Chain Variable Region.

Figure 3:
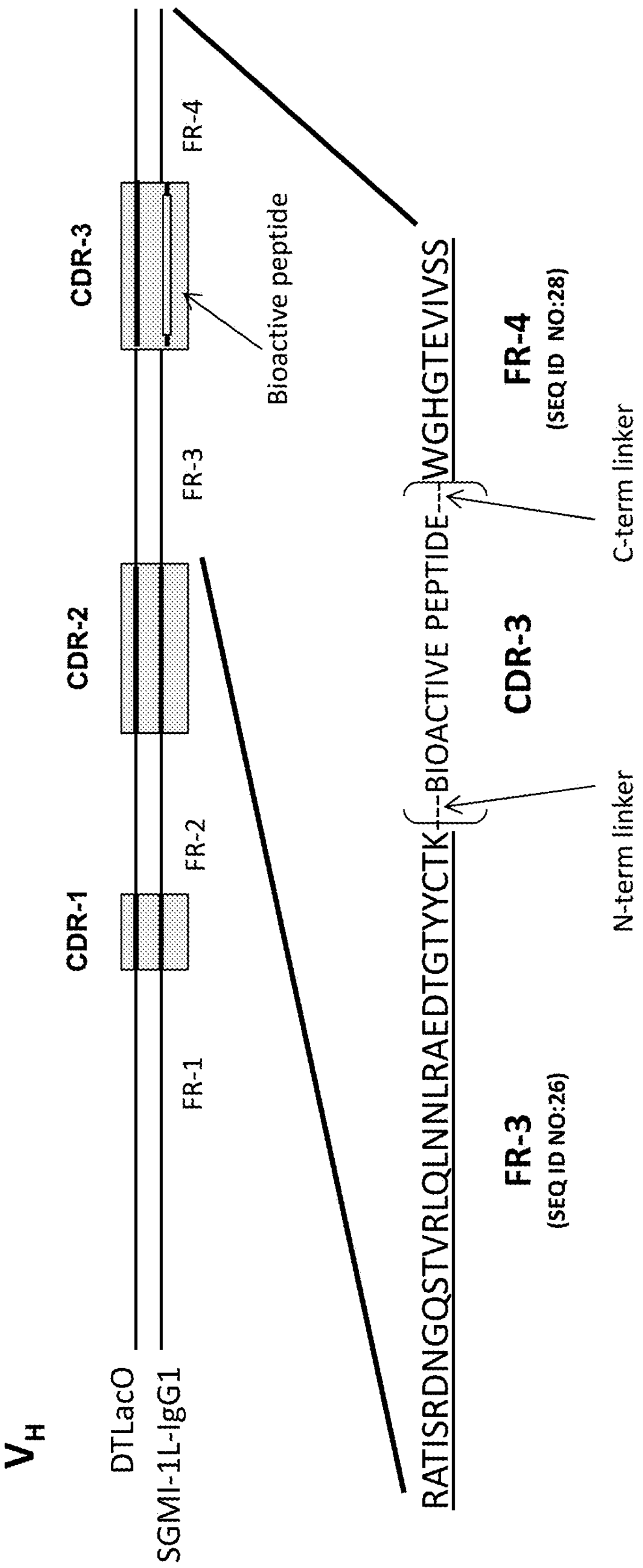
FIG. 3 illustrates an exemplary parental (DTLacO) variable heavy chain polypeptide sequence compared to a variable heavy chain polypeptide sequence comprising a bioactive peptide amino acid sequence engrafted within complementarity determining region-3 (CDR-3)

The DT40 chicken heavy chain variable region was chosen as the starting parental clone for use as a scaffold into which SGMI-1 or SGMI-2 peptide sequences were engrafted into the CDR-H3 region, as shown in FIGS. 3 and 4.

FIG. 3 illustrates an exemplary parental (DTLacO) variable heavy chain polypeptide sequence compared to a modified version of the variable heavy chain polypeptide sequence comprising a bioactive peptide amino acid sequence engrafted within CDR-H3. As shown in FIG. 3, the chicken heavy chain variable region contains three CDRs (CDR-H1, CDR-H2 and CDR-H3), flanked by four framework regions (FR-1, FR-2, FR-3 and FR-4). The inventors have surprisingly discovered that by engrafting a bioactive peptide (e.g. SGMI-1 or SGMI-2) into a CDR of the heavy chain variable region of the DT40 parental chicken antibody (which provides the antibody scaffold), the biological activity of the bioactive peptide was conferred to the parental antibody comprising the engrafted bioactive peptide sequence.

The parental chicken antibody provides the framework regions (FR1, FR2, FR3 and FR4) of the heavy and light chains, which are conserved between various clones. Any parental chicken antibody clone may be selected for use as a scaffold. In some embodiments, the parental chicken antibody clone may be selected based on desirable properties, such as stability.

Exemplary parental chicken heavy chain variable regions are provided below. As shown in FIG. 4, although the native CDR regions vary between parental clones, the Framework regions between the CDRs are conserved in chicken, accordingly, a consensus FR-1, FR-2, FR-3 and FR-4 sequence derived from an alignment of several different parental chicken heavy chain regions is also provided below. As further shown in FIG. 4, in FR-3 there is a conserved cysteine (C) residue at the third position N-terminal to CDR-H3 in the parental clones (corresponding to the cysteine at position 31 in SEQ ID NO:26), which is retained in FR-3 in the constructs containing an engrafted bioactive peptide in CDR-H3. As further shown in FIG. 4, in FR-4 there is a conserved tryptophan (W) residue at the position immediately adjacent to CDR-H3 in the parental clones (corresponding to the tryptophan at position 1 in SEQ ID NO:28), which is retained in FR-4 in the constructs containing an engrafted bioactive peptide in CDR-H3.

DTLacO Parental Chicken (Clone #1) Heavy Chain Variable Region: (DTLacO VH) (SEQ ID NO:23)

AVTLDESGGGLQTPGRALSLVCKASGFITSSYNMGWVRQAPGKGLEFVAG
IDNTGRYTGYGSAVKGRATISRDNGQSTVRLQLNNLRAEDTGTYYCAKAA
GGSGYCGSGAYIDAWGHGTEVIVSS

The $V_H$ CDRs (31-35 (H1); 50-66 (H2); and 99-114 (H3) are underlined, and the Framework regions (1-30 (FR-1); 36-49 (FR-2); 67-98 (FR-3) and 115-125 (FR-4) are italicized.

DTLacO Parental Chicken (Clone #2) Heavy Chain Variable Region (DTLacO VH) (SEQ ID NO:91)

AVTLDESGGGLQTPGGALSLVCKASGFTFSSNAMGWVRQAPGKGLEWVAG
IDDDGSGTRYAPAVKGRATISRDNGQSTLRLQLNNLRAEDTGIYYCTKCA
YSSGCDYEGGYIDAWGHGTEVIVSS

Conserved FR-1 Region from the DTLacO VH is Set Forth as SEQ ID NO:24:

AVTLDESGGGLQTPGXALSLVCKASGFTFS

Where X=R or G

Conserved FR-2 Region from the DTLacO VH is Set Forth as SEQ ID NO:25:

WVRQAPGKGLEXVA

Where X=F or W

Conserved FR-3 Region from the DTLacO VH is Set Forth as SEQ ID NO:26:

$RATISRDNGQST\mathbf{X}_1RLQLNNLRAEDTGIYY\mathbf{CX}_2K$

Where:
$X_1$=V or L, and
$X_2$=A or T

Conserved FR-3 Flanking Region Adjacent to CDR-H3 is Set Forth as SEQ ID NO:27:
YYCXK
where X=A or T Conserved FR-4 Region from the DTLacO VH is Set Forth as SEQ ID NO:28:

WGHGTEVIVSS

Conserved FR-4 Flanking Region Adjacent to CDR-H3 is Set Forth as SEQ ID NO:29
WGHGT As shown in FIG. 4, in some embodiments, a peptide linker was included at the amino terminus of the bioactive peptide, or at the carboxy terminus of the bioactive peptide, or at both locations. The peptide linker may be any flexible linker sequence, such a sequence shown in TABLE 4. In some embodiments, the linker sequence was derived from the native CDR-H3 sequence in the parental clone. As further shown in FIG. 4, in some embodiments, the bioactive peptide sequence replaced all but one of the sixteen original amino acid residues of the native CDR-H3 (see, e.g. SGMI-1L), wherein the remaining one amino acid sequence is included as a linker. In some embodiments, eight of the sixteen original amino acid residues of the native CDR-H3 were retained in either the C-terminal linker (see e.g., SGMI-1L5), and up to fourteen of the original sixteen amino acid residues of the native CDR-H3 were retained in the C-terminal and N-terminal linker regions (see SGMI-L7).

2. SGMI-1 and SGMI-2 Engrafted into the CDR-L1 of a Parental Chicken Light Chain Variable Region.

A DT40 chicken light chain variable region was chosen as the starting parental clone for use as a scaffold into which SGMI-1 or SGMI-2 peptide sequences were engrafted into the CDR-L1 region, as shown in FIGS. 5 and 6.

FIG. 5 illustrates an exemplary parental (DTLacO) variable light chain polypeptide sequence compared to a variable light chain polypeptide sequence comprising a bioactive peptide amino acid sequence engrafted within CDR-L1. As shown in FIG. 5, the chicken light chain variable region contains three CDRs (CDR-L1, CDR-L2 and CDR-L3), flanked by four framework regions (FR-1, FR-2, FR-3 and FR-4). Similar to the results obtained with CDR-H3 in the variable heavy chain polypeptide, the inventors have discovered that by engrafting a bioactive peptide sequence (e.g. SGMI-1) into CDR-L1 of the variable light chain polypeptide from a parental chicken antibody (which provides the antibody scaffold), the parental antibody comprising the engrafted bioactive peptide sequence is converted into an antibody that comprises biological activity of the bioactive peptide (i.e., inhibition of the lectin pathway was observed with the construct SGMI-IL, data not shown).

Exemplary parental chicken light chain variable regions are provided below. As shown in FIG. 6, although the native CDR regions vary between parental clones, the Framework regions between the CDRs are conserved in chicken, accordingly, a consensus FR-1, FR-2, FR-3 and FR-4 sequence derived from an alignment of several different parental chicken light chain regions is also provided below. As further shown in FIG. 6, in FR-1 there is a conserved cysteine (C) residue at the position immediately adjacent to CDR-L1 in the parental clones (corresponding to the cysteine at position 23 in SEQ ID NO:31), which is retained in FR-1 in the constructs containing an engrafted bioactive peptide in CDR-L1. As further shown in FIG. 6, in FR-2 there is a conserved tryptophan (W) residue at the position immediately adjacent the CDR-L1 in the parental clones (corresponding to the tryptophan at position 1 in SEQ ID NO:33), which is retained in FR-2 in the constructs containing an engrafted bioactive peptide in CDR-L1.

DTLacO Chicken (Clone #1) Light Chain Variable Region (DTLacO VL) (SEQ ID NO:30)

*ALTQPSSVSANPGGTVKITC*<u>SGDSSYYG</u>*WYQQKAPGSAPVTVIY*<u>DNTN</u>
<u>RPS</u>*NIPSRFSGSKSGSTATLTITGVRADDNAVYYC*<u>ASTDSSSTA</u>FGAG
*TTLTVL*

The $V_L$ CDRs (21-28 (L1); 45-51 (L2); and 84-92 are underlined and the Framework regions (1-20 (FR-1); 29-44 (FR-2); 52-83 (FR-3) and 93-102 (FR-4) are italicized.

DTLacO Chicken (Clone#2) Light Chain Variable Region (DTLacO VL) SEQ ID NO:92)

*ALTQPASVSANPGETVKITC*<u>SGGGSYAGSYYYG</u>*WYQQKAPGSAPVTLI*
*Y*<u>*YNNKRPS*</u>DIPS*RFSGSLSGSTNTLTITGVRADDEAVYFC*<u>GSADNSGAA</u>
*FGAGTTLTVL*

Conserved FR-1 Region from the DTLacO VL is Set Forth as SEQ ID NO:31:

$ALTQPX_1SVSANX_2GX_3TVKITC$

Where:
$X_1$=A or S
$X_2$=L or P
$X_3$=G or E

Conserved FR-1 Flanking Region Adjacent to CDR-L1 is Set Forth as SEQ ID NO:32

VKITC

Conserved FR-2 Region from the DTLacO VL is Set Forth as SEQ ID NO:33:

$WYQQKX_1PGSAPVTX_2IY$

Where
$X_1$=A or S,
$X_2$=V or L

Conserved FR-2 Flanking Region Adjacent to CDR-L1 is Set Forth as SEQ ID NO:34

WYQQK

Conserved FR-3 Region from the DTLacO VL is Set Forth as SEQ ID NO:35:

$X_1IPSRFSGSX_2SGSTX_3TLTITGVRADDX_4AVYX_5C$

Where:

$X_1$=N or D $X_2$=K or L $X_3$=A or N $X_4$=N or E $X_5$=Y or F

Conserved FR-4 Region from the DTLacO VL is Set Forth as SEQ ID NO:36

FGAGTTLTVL

As shown in FIG. 6, in some embodiments, a peptide linker was included at the amino terminus of the bioactive peptide, or at the carboxy terminus of the bioactive peptide, or at both locations. The peptide linker may be any flexible linker sequence, such as the sequences shown in TABLE 4. In some embodiments, the linker sequence was derived from the native CDR-L1 sequence in the parental clone. As further shown in FIG. 6, in some embodiments, the bioactive peptide replaced five of the thirteen original amino acid residues of the native CDR-L1 (see, e.g. SGMI-2L), retaining a portion of the original CDR-L1 sequence as a peptide linker flanking the bioactive peptide sequence.

TABLE 4

Exemplary Peptide Linkers for engrafting bioactive peptides into CDRs:

| SEQ ID NO: | Sequence |
|---|---|
| 12 | GTGGGSGSSSRS |
| 13 | GTGGGSGSSS |
| 37 | AAGGSG |
| 38 | AAGGSGGSGA |
| 39 | YIDA |
| 40 | AYIDA |
| 41 | GTGGGSGSSSYIDA |
| 42 | GSGAYIDA |
| 43 | AAGGSGGSGAYIDA |
| 44 | SGGGS |
| 45 | YYYG |
| 46 | GSGA |

In some embodiments, the chicken variable heavy chain region is fused to a human IgG1 constant region, resulting in a chicken/human chimeric antibody. An exemplary human IgG1 constant region is provided below as SEQ ID NO:47.

Human IgG1 Constant Region (CH1-Hinge-CH2-CH3): SEQ ID NO:47

ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKVE

PKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLN

-continued

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

In some embodiments, the chicken variable light chain region is fused to a human lambda light chain constant region, resulting in a chicken/human chimeric antibody. An exemplary human lambda light chain constant region is provided below as SEQ ID NO:48.

Human Lambda Light Chain Constant Region (SEQ ID NO:48)

GQPKAAPSVTLFPPSSEELQANKATLVCLISDFYPGAVTVAWKADSSPV

KAGVETTTPSKQSNNKYAASSYLSLTPEQWKSHRSYSCQVTHEGSTVEK

TVAPTECS

The resulting polynucleotide constructs were designated pcDNA3-SGMI-1L-IgG1, -1M-IgG1, -1S-IgG1, and -1-L1-IgG1 to -1-L12-IgG1 (SEQ ID NOS: 49, 51, 53, 55, 57, 59, 61, 63, 65, 67, 69, 71, 73, 75 and 77) and pcDNA3-SGMI-2L-Igλ, -2M-Igλ, and -2S-Igλ (SEQ ID NOS:79, 81 and 83), while the polypeptides were termed Ab-SGMI-1L-IgG1, -1M-IgG1, -1S-IgG1, and -1-L1-IgG1 to -1-L12-IgG1 (SEQ ID NOS: 50, 52, 54, 56, 58, 60, 62, 64, 66, 68, 70, 72, 74, 76 and 78), as shown in FIG. 4, and Ab-SGMI-2L-Igλ-, -2M-Igλ, and -2S-Igλ (SEQ ID NOS: 80, 82 and 84), as show in FIG. 6.

Freestyle™293-F or Expi293F™ cells were transiently transfected with combinations of expression plasmids as follows: (a) pcDNA3-SGMI-1-IgG1-1L, (et al.), plus a light chain plasmid encoding the DTLacO VL; (b) pcDNA3-SGMI-2-Igλ-L1 (et. al.), plus a heavy chain plasmid encoding the DTLacO VH; (c) pcDNA3-SGMI-1-IgG1-1L plus pcDNA3-SGMI-2-Igλ-L1. After four days of incubation at 37° C., the culture media were harvested and the SGMI-bearing chimeric antibodies were purified by Protein A affinity chromatography.

Results:

Chimeric Chicken/Human Antibodies Comprising SGMI-1 Engrafted into CDR-H3

The Wieslab® Complement System Screen, MBL Pathway, as described in Example 2, was used to measure functionality of the chimeric antibodies. Assays were run in duplicate with the SGMI-1Fc (generated as described in Example 2) as the positive (inhibitory) controls. A matching isotype antibody was included as a negative control.

Figure 7A:
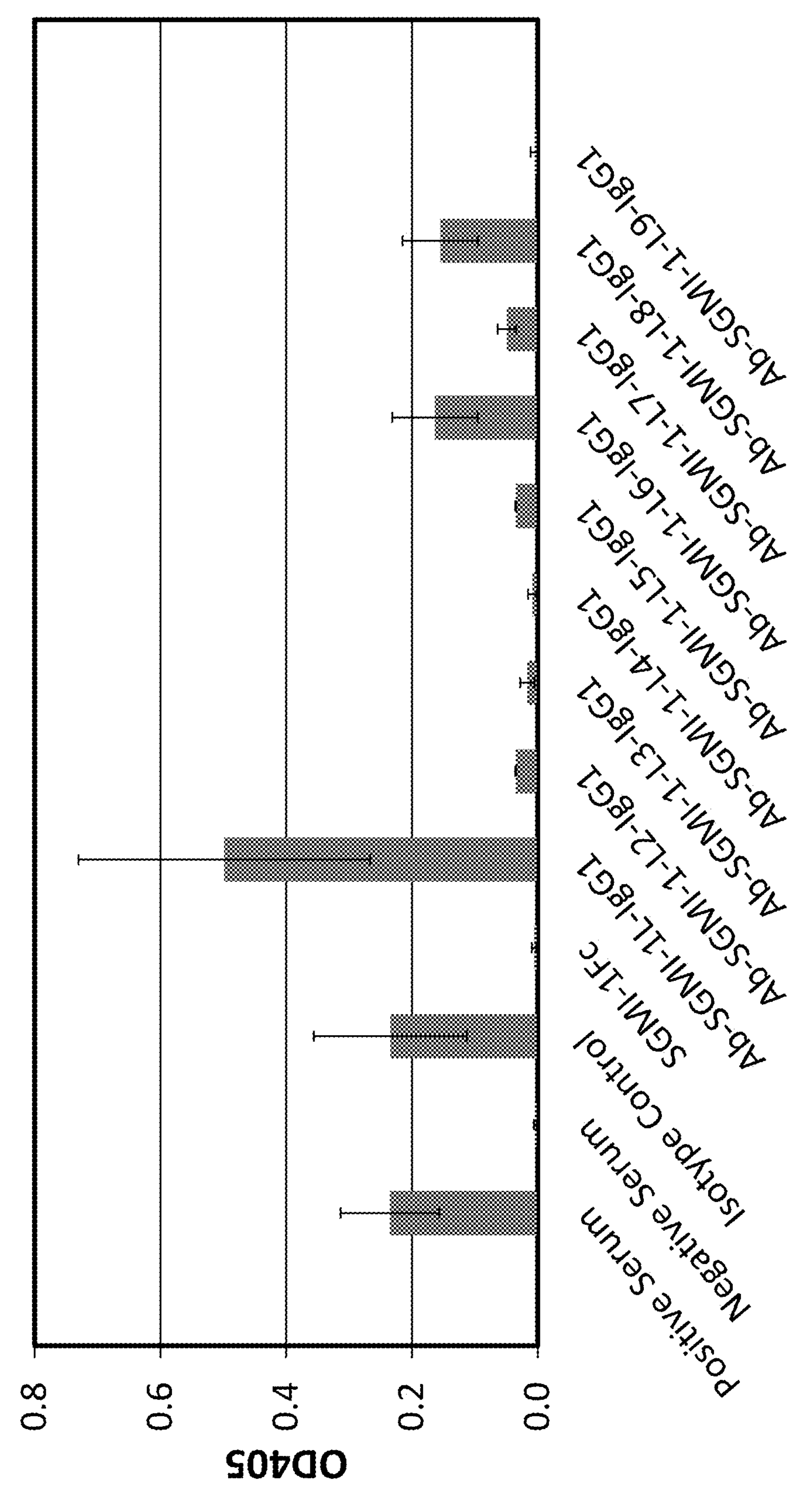
FIG. 7A graphically illustrates the inhibitory activity of various representative chimeric chicken/human mAbs containing SGMI-1 engrafted into CDR-H3 on C5b-C9 deposition.
Figure 7B:
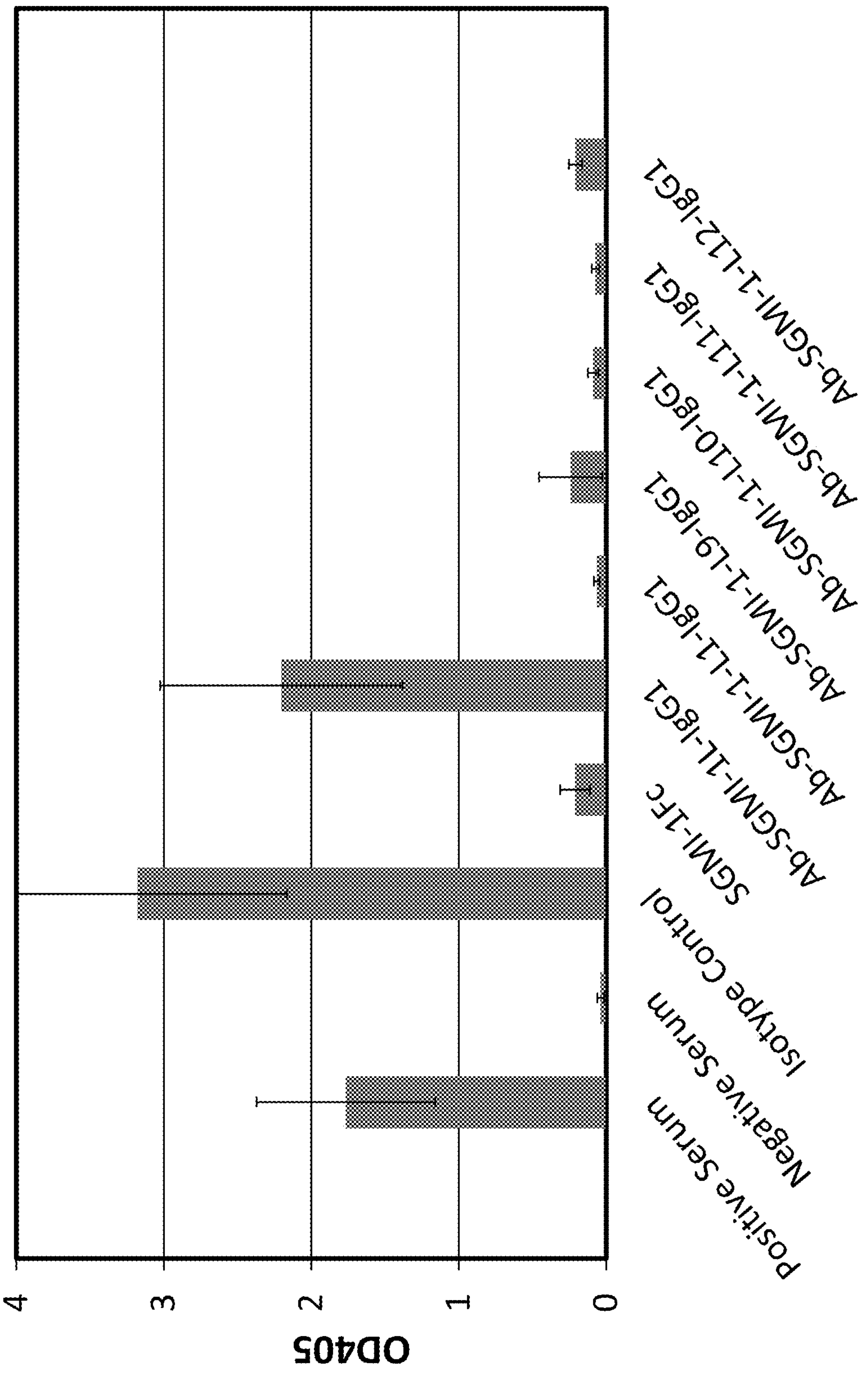
FIG. 7B graphically illustrates the inhibitory activity of additional various representative chimeric chicken/human mAbs containing SGMI-1 engrafted into CDR-3 on C5b-C9 deposition.

FIGS. 7A and 7B graphically illustrate the inhibitory activity of various representative chimeric chicken/human mAbs containing SGMI-1 engrafted into CDR-H3 on MBL complement activity. The data are distributed across two figures because the assays were conducted at different times. As shown in FIGS. 7A and 7B, several of the chimeric mAbs containing SGMI-1 engrafted within the CDR-H3 inhibit C5b-C9 deposition to a degree similar to the positive SGMI-Fc fusion protein (e.g., Ab-SGMI-1-L2, -L3, -L4, -L5, -L7, -L9, -L1, -L10, -L11 and -L12). As shown in FIG. 4, these constructs differ only in the nature of the flexible linkers separating the inhibitory peptide from the antibody framework regions. Interestingly, another chimeric mAb with SGMI-1 engrafted into the CDR-H3, referred to as "Ab-SGMI-1L," has no inhibitory activity. As shown in FIG. 4, Ab-SGMI-1L has only a one amino acid residue linker between the bioactive peptide and framework segments.

The Ab-SGMI-1 antibodies were also assessed for lectin pathway inhibition in an assay of C3b deposition on mannan-coated beads. This assay, which determines degree of activity by flow cytometry, offers greater resolution than the Wieslab® assay. The Lectin Pathway bead assay was carried out as follows: mannan was adsorbed to 7 μM-diameter polystyrene beads (Bangs Laboratories; Fishers, Ind., USA) overnight at 4° C. in carbonate-bicarbonate buffer (pH 9.6). The beads were washed in PBS and exposed to 10% serum, or 10% serum pre-incubated with antibodies or inhibitors. The serum-bead mixture was incubated at room temperature for one hour while agitating. Following the serum incubation, the beads were washed, and C3 deposition on the beads was measured by detection with an anti-C3c rabbit polyclonal antibody (Dako North America; Carpinteria, Calif., USA) and a PE-Cy5 conjugated goat anti-rabbit secondary antibody (Southern Biotech; Birmingham, Ala., USA). Following the staining procedure, the beads were analyzed using a FACS Calibur cytometer. The beads were gated as a uniform population using forward and side scatter, and C3 deposition was apparent as FL3-positive particles (FL-3, or "FL-3 channel" indicates the 3rd or red channel on the cytometer). The Geometric Mean Fluorescence Intensity (MFI) for the population for each experimental condition was plotted relative to the antibody/inhibitor concentration to evaluate lectin pathway inhibition.

Figure 8A:
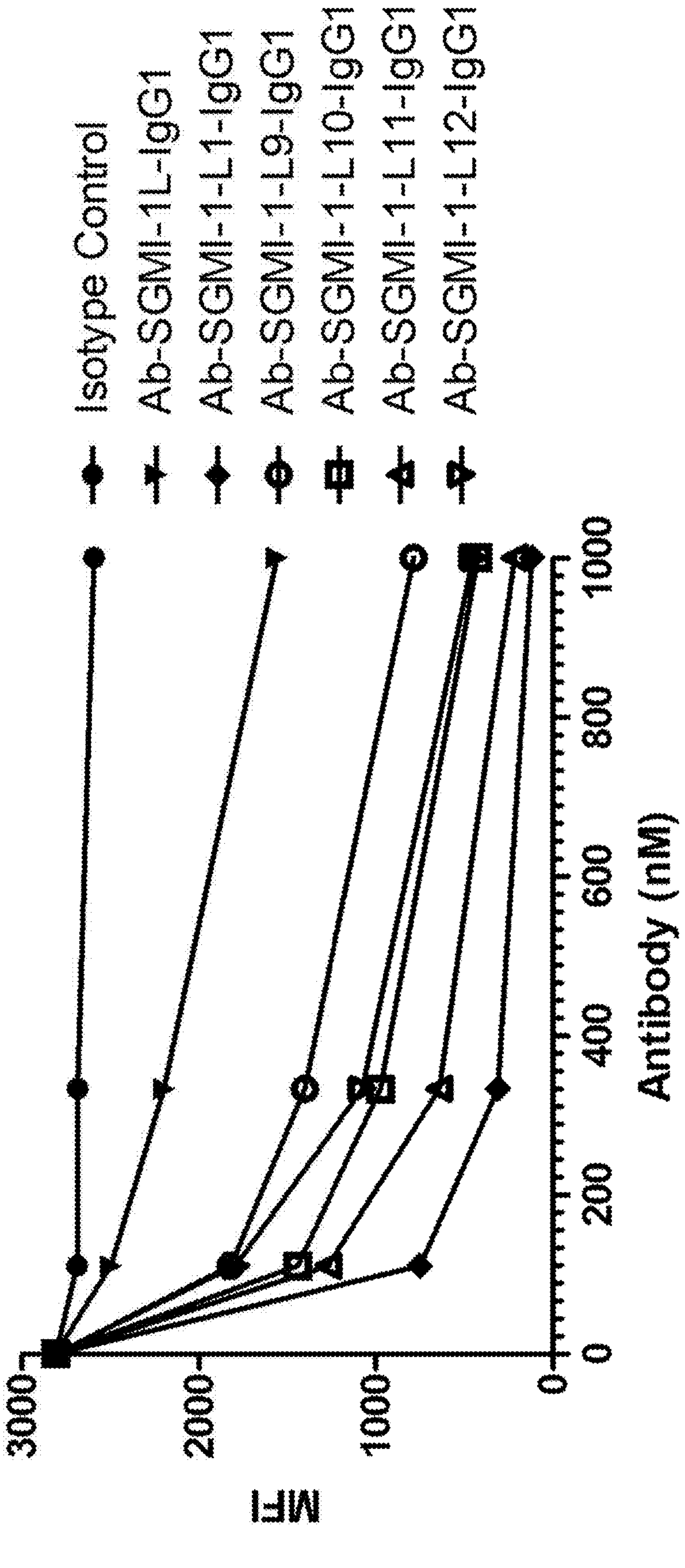
FIG. 8A graphically illustrates the inhibitory activity of various representative chimeric chicken/human mAbs containing SGMI-1 engrafted into CDR-H3 on complement C3b deposition activity in a dose-response manner.
Figure 8B:
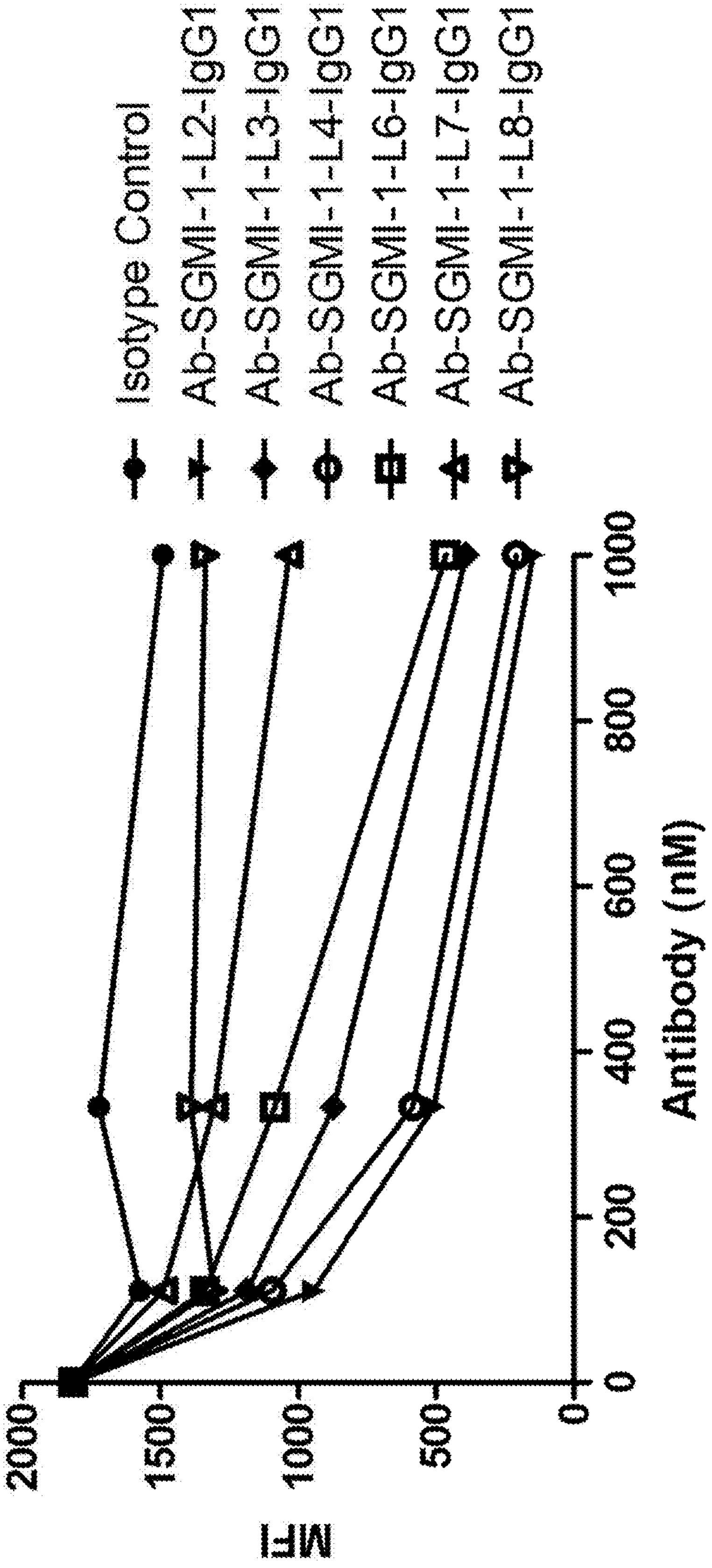
FIG. 8B graphically illustrates the inhibitory activity of additional various representative chimeric chicken/human mAbs containing SGMI-1 engrafted into CDR-H3 on complement C3b deposition activity in a dose-response manner.

As shown in FIGS. 8A and 8B, all of the antibodies containing SGMI-1 engrafted into CDR-H3 inhibited lectin pathway activity in the bead assay, but with varying degrees of potency. It is noted that the differences between the antibodies are more readily discerned in this bead assay as compared to the Wieslab® assay.

In summary, these results demonstrate that inhibitory therapeutic polypeptides may be generated by engrafting a bioactive peptide into the CDR-H3 of a chicken antibody scaffold.

Chimeric Chicken/Human Antibodies Comprising SGMI-2 Engrafted into CDR-L1

Figure 9A:
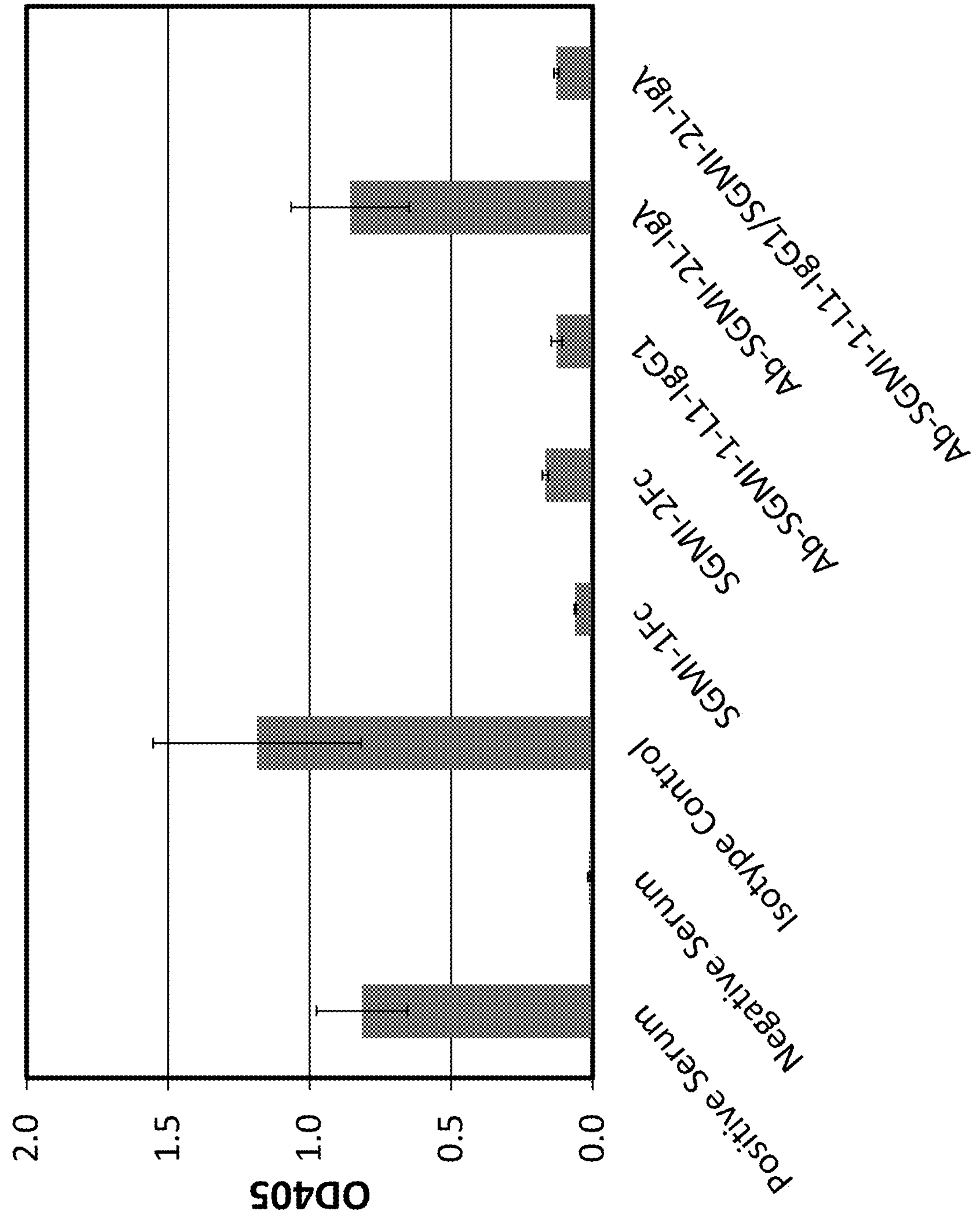
FIG. 9A graphically illustrates the inhibitory activity of a chimeric chicken/human mAb comprising SGMI-2 engrafted within CDR-L1 (Ab-SGMI-2L-Igλ) and a combination of SGMI-1 engrafted within CDR-H3 and SGMI-2 engrafted within CDR-L1 (Ab-SGMI-1-L1-IgG1/SGMI-2L-Igλ), demonstrating that the chimeric combination SGMI-1-SGMI-2 mAb (Ab-SBMI-1-L1-IgG1/SGMI-2L-Igλ) inhibits C5b-C9 deposition.

FIG. 9A graphically illustrates that a chimeric chicken/human mAb comprising SGMI-2 engrafted within CDR-L1 (Ab-SGMI-2L-Igλ) exerts little to no inhibitory activity in the Wieslab complement system MBL pathway assay. These results leave room for optimization of the linker elements flanking the bioactive peptide, which significantly impacted the efficacy of the SGMI-1-containing mAbs (as shown in FIGS. 7A and 7B).

Chimeric Chicken/Human Antibodies Comprising SGMI-1 and SGMI-2

Figure 9B:
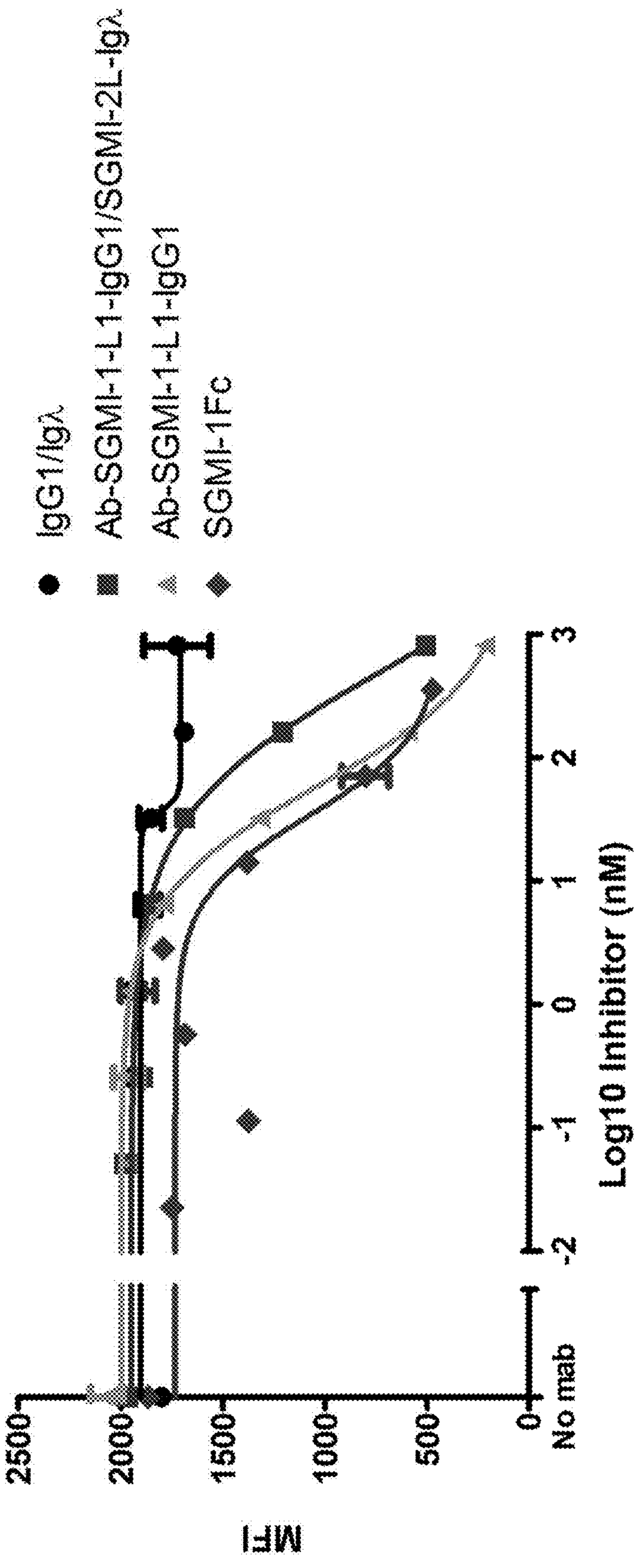
FIG. 9B graphically illustrates the inhibitory activity of a chimeric chicken/human mAb comprising a combination of SGMI-1 engrafted within CDR-H3 and SGMI-2 engrafted within CDR-L1 (Ab-SGMI-1-L1-IgG1/SGMI-2L-Igλ), demonstrating that the chimeric combination SGMI-1-SGMI-2 mAb (Ab-SGMI-1-L1-IgG1/SGMI-2L-Igλ) inhibits C5b-C9 deposition.

FIG. 9A also shows the activity of a chimeric chicken/human antibody comprising SGMI-1 and SGMI-2 engrafted into CDR-H3 and CDR-L1, respectively. Ab-SGMI-1-L1-IgG1/SGMI-2-L-Igλ is nearly as potent as the mAb containing only the SGMI-1 peptide (Ab-SGMI-1-L1-IgG1). This outcome was confirmed using the flow cytometric mannan-coated bead assay, as shown in FIG. 9B. Together, these data demonstrate that the SGMI-1 peptide engrafted into CDR-H3 inhibits the lectin pathway whether or not the SGMI-2 peptide is present engrafted into CDR-L1. Based on the results described herein, further optimization of the SGMI-2 flanking linkers is expected to add MASP-2 inhibitory activity to the antibody already carrying SGMI-1-mediated MASP-1 inhibitory activity.

Example 4

This Example describes the generation of chimeric antibodies comprising one or more bioactive peptides (e.g. SGMI-1 or SGMI-2) fused onto the amino or carboxy termini of the heavy and light chains of a chimeric chicken/human antibody.

Rationale:

As demonstrated in Examples 2 and 3, the inhibitory functions of the SGMI-1 and SGMI-2 peptides (and truncated variants thereof) were preserved in the SGMI-Fc proteins and also, for SGMI-1, when displayed within the CDR regions of a full antibody. In this Example, experiments were carried out to determine whether the SGMI peptides would retain activity when fused to the amino or carboxy termini of antibody heavy or light chains of a chimeric chicken/human antibody.

TABLE 5

Chimeric chicken/human antibodies with the bioactive peptides SGMI-1 and SGMI-2 fused to the N- or C-termini of the heavy or light chains.

| Antibody | Peptide Location on Antibody | | | | SEQ ID NO: |
|---|---|---|---|---|---|
| | HC-N | HC-C | LC-N | LC-C | |
| Ab-IgG1-S10 | SGMI-1 | — | — | — | 94 |
| Ab-IgG1-S20 | SGMI-2 | | — | — | 96 |
| Ab-IgG1-S01 | — | SGMI-1 | — | — | 98 |
| Ab-IgG1-S02 | — | SGMI-2 | — | — | 100 |
| Ab-Igλ-S10 | — | | SGMI-1 | — | 102 |
| Ab-Igλ-S20 | | | SGMI-2 | | 104 |
| Ab-Igλ-S01 | | | — | SGMI-1 | 106 |
| Ab-Igλ-S02 | | | | SGMI-2 | 108 |

Abbreviations in Table 5:
"HC-N" = amino terminus of heavy chain
"HC-C" = carboxyl terminus of heavy chain
"LC-N" = amino terminus of light chain
"LC-C" = carboxyl terminus of light chain For the N-terminal fusions shown in TABLE 5, a peptide linker (SEQ ID NO:14) was added between the bioactive peptide and the chicken variable region.

Figure 10:
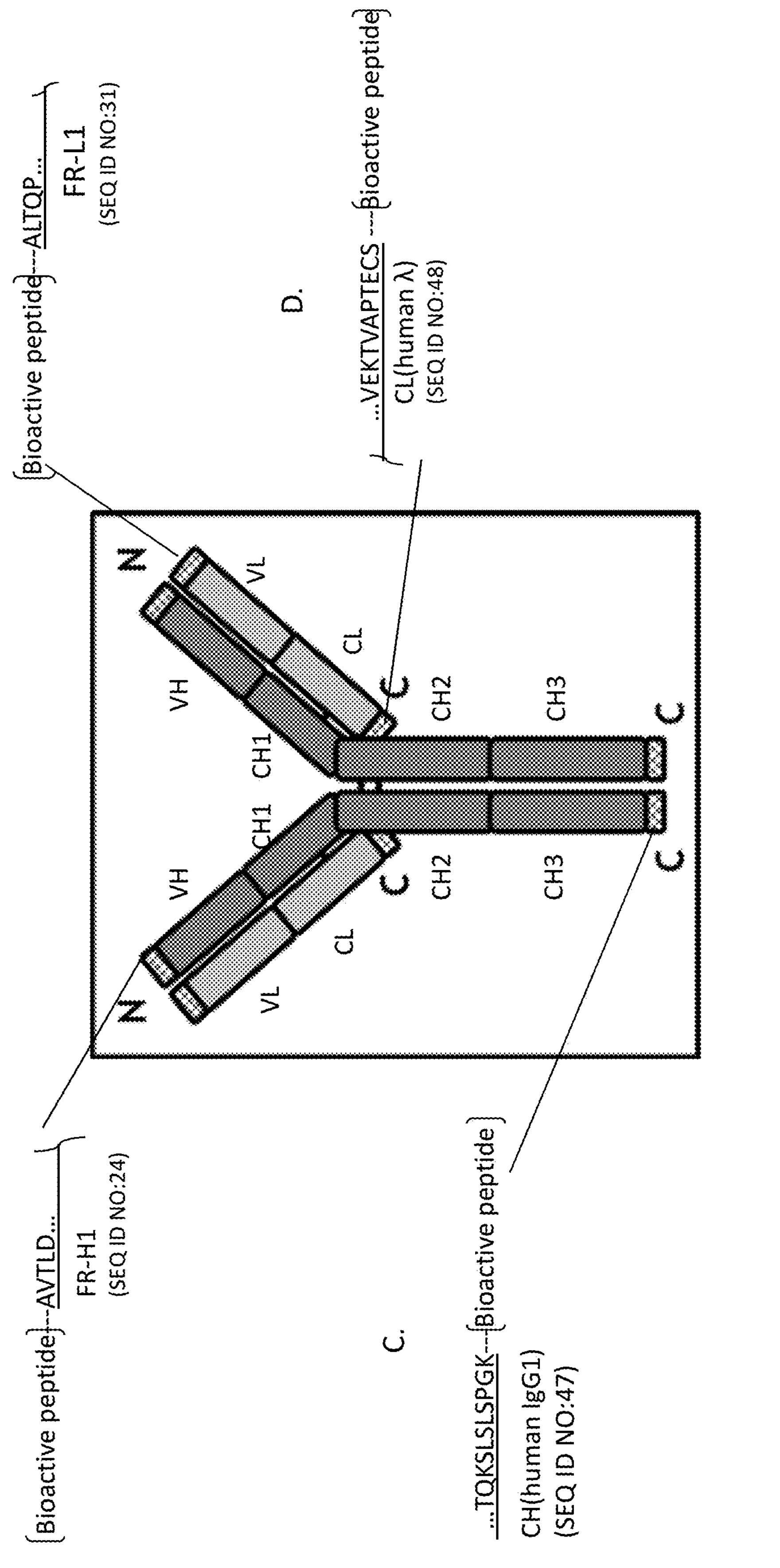
FIG. 10 illustrates a chimeric chicken/human antibody comprising bioactive peptides fused to the N-terminus of the heavy chain variable region (A); and/or the N-terminus of the light chain variable region (B); and/or the C-terminus of the heavy chain constant region (C); and/or the C-terminus of the light chain constant region (D)

For the C-terminal fusions shown in TABLE 5, a peptide linker (SEQ ID NO:37) was added between the constant region and the bioactive peptide, and a second peptide "GSGA" (SEQ ID NO:46) was added at the C-terminal end of the fusion polypeptide to protect C-terminal SGMI peptides from degradation. These fusion constructs are illustrated schematically in FIG. 10.

Figure 11:
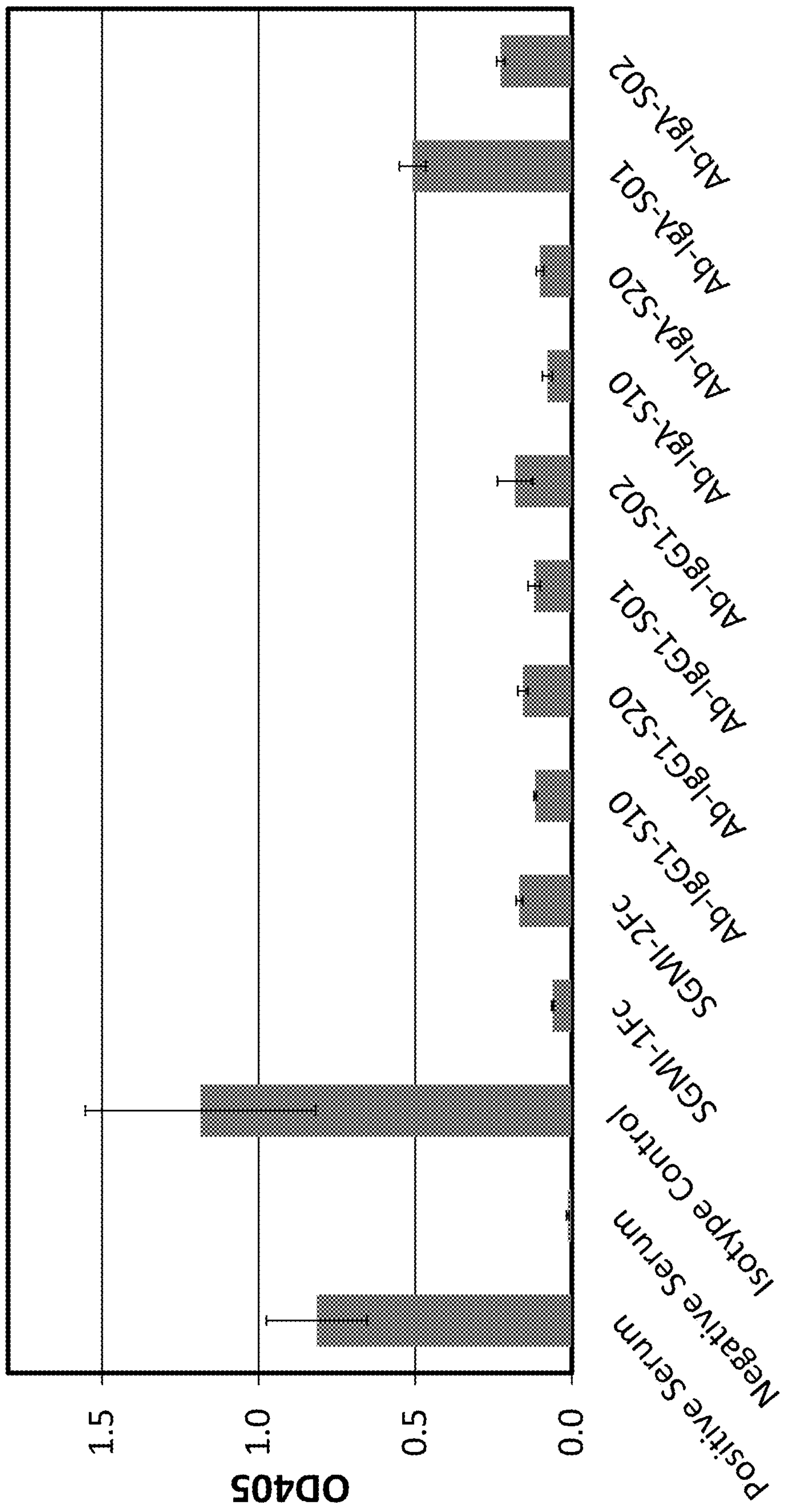
FIG. 11 graphically illustrates the inhibitory activity of chimeric chicken/human antibodies comprising bioactive SGMI-1 or SGMI-2 peptides fused to the N- or C-terminus of the heavy or light chain, demonstrating that all of the peptide-mAb fusions inhibit C5b-C9 deposition.

FIG. 11 illustrates the inhibitory activity of the N- and C-terminal peptides in the Wieslab assay. Compared to the positive and negative controls, all of the fusion mAbs inhibited C5b-9 deposition. All except for one fusion mAb—SGMI-1 fused to the C-terminus of the light chain—exhibited levels of inhibition comparable to those of the control SGMI-1 and SGMI-2 Fc-fusion proteins. Several of these N- and C-terminal peptide-mAb fusions were also tested in the flow cytometric mannan-coated bead assay described in Example 3, with similar results (data not shown). These antibodies m for the development of bi-specific antibodies bearing combinations of SGMI-1 and SGMI-2.

While the preferred embodiment of the invention has been illustrated and described, it will be appreciated that various changes can be made therein without departing from the spirit and scope of the invention.

The embodiments of the invention in which an exclusive property or priviliedge is claimed are defined as follows:

1. A method of inhibiting lectin pathway complement activation in a human subject comprising administering a composition comprising an isolated antibody which comprises a bioactive peptide comprising the amino acid sequence of SEQ ID NO:6, in an amount sufficient to inhibit lectin pathway complement activation in said human subject, wherein said antibody comprises a heavy chain comprising SEQ ID NO:56 and a light chain comprising SEQ ID NO:30.

2. The method of claim 1, wherein the light chain further comprises a human lambda light chain constant region.

* * * * *

UNITED STATES PATENT AND TRADEMARK OFFICE

CERTIFICATE OF CORRECTION

PATENT NO. : 11,045,544 B2
APPLICATION NO. : 15/459645
DATED : June 29, 2021
INVENTOR(S) : W. Jason Cummings et al.

It is certified that error appears in the above-identified patent and that said Letters Patent is hereby corrected as shown below:

On the Title Page

Page 2, in Column 1, item (56), in OTHER PUBLICATIONS, Line 14, delete "LacO/Lacl Regulatory" and insert -- LacO/Laci Regulatory --, therefor.

Page 2, in Column 1, item (56), in OTHER PUBLICATIONS, Line 43, delete "Immunoglobuline Variable" and insert -- Immunoglobulin Variable --, therefor.

Page 2, in Column 1, item (56), in OTHER PUBLICATIONS, Line 45, delete "Fragements" and insert -- Fragments --, therefor.

Page 2, in Column 2, item (56), in OTHER PUBLICATIONS, Line 7, delete "Lectin Pathway Activation Complex Encoed" and insert -- Lectin Pathway Activated Complex Encoded --, therefor.

Page 2, in Column 2, item (56), in OTHER PUBLICATIONS, Line 47, delete "Fragmetns,"" and insert -- Fragments --, therefor.

Page 2, in Column 2, item (56), in OTHER PUBLICATIONS, Line 63, delete "stiumlating" and insert -- stimulating --, therefor.

In the Specification

In Column 4, Lines 41-42, delete "peptide." and insert -- peptide; --, therefor.

In Column 6, Line 17, delete "linkers" and insert -- linkers; --, therefor.

In Column 6, Line 38, delete "1 S-IgGl)" and insert -- 1S-IgGl) --, therefor.

In Column 12, Line 17, delete "e.g." at all occurrences and insert -- e.g., --, therefor.

Signed and Sealed this
Twenty-seventh Day of December, 2022

Katherine Kelly Vidal

Katherine Kelly Vidal
*Director of the United States Patent and Trademark Office*

In Column 13, Line 9, delete “Kluyvermyces” and insert -- Kluyveromyces, --, therefor.

In Column 15, Line 67, delete “7,8 9” and insert -- 7,8, 9 --, therefor.

In Column 18, Lines 20-21, delete “bacterio-cidal and virocidal” and insert -- bactericidal and virucidal peptide drugs --, therefor.

In Column 20, Line 17, delete “(iii)” and insert -- (iv) --, therefor.

In Column 20, Line 17, delete “(iv)” and insert -- (v) --, therefor.

In Column 20, Line 18, delete “(v)” and insert -- (vi) --, therefor.

In Column 20, Line 19, delete “(vi)” and insert -- (vii) --, therefor.

In Column 20, Line 20, delete “(vii)” and insert -- (viii) --, therefor.

In Column 21, Line 20, delete “(viii)” and insert -- (ix) --, therefor.

In Column 20, Line 46, delete “Tacchykinin” and insert -- Tachykinin --, therefor.

In Column 20, Line 57, delete “Endothelian” and insert -- Endothelin --, therefor.

In the Claims

In Column 191, Line 47, delete “priviliedge” and insert -- privileged --, therefor.

SEQUENCE LISTING

```
<160> NUMBER OF SEQ ID NOS: 108

<210> SEQ ID NO 1
<211> LENGTH: 6476
<212> TYPE: DNA
<213> ORGANISM: Homo Sapiens

<400> SEQUENCE: 1

acacacagag tgatacaaat acctgcttga gcccctcagt tattttctct caagggctga     60

agtcagccac acaggataaa ggagggaagg gaaggagcag atcttttcgg taggaagaca    120

gattttgttg tcaggttcct gggagtgcaa gagcaagtca aaggagagag agaggagaga    180

ggaaaagcca gagggagaga gggggagagg ggatctgttg caggcagggg aaggcgtgac    240

ctgaatggag aatgccagcc aattccagag acacacaggg acctcagaac aaagataagg    300

catcacggac accacaccgg gcacgagctc acaggcaagt caagctggga ggaccaaggc    360

cgggcagccg ggagcaccca aggcaggaaa atgaggtggc tgcttctcta ttatgctctg    420

tgcttctccc tgtcaaaggc ttcagcccac accgtggagc taaacaatat gtttggccag    480

atccagtcgc ctggttatcc agactcctat cccagtgatt cagaggtgac ttggaatatc    540

actgtcccag atgggtttcg gatcaagctt tacttcatgc acttcaactt ggaatcctcc    600

tacctttgtg aatatgacta tgtgaaggta gaaactgagg accaggtgct ggcaaccttc    660

tgtggcaggg agaccacaga cacagagcag actcccggcc aggaggtggt cctctcccct    720

ggctccttca tgtccatcac tttccggtca gatttctcca atgaggagcg tttcacaggc    780

tttgatgccc actacatggc tgtggatgtg gacgagtgca aggagaggga ggacgaggag    840

ctgtcctgtg accactactg ccacaactac attggcggct actactgctc ctgccgcttc    900

ggctacatcc tccacacaga caacaggacc tgccgagtgg agtgcagtga caacctcttc    960

actcaaagga ctggggtgat caccagccct gacttcccaa acccttaccc caagagctct   1020

gaatgcctgt ataccatcga gctggaggag ggtttcatgg tcaacctgca gtttgaggac   1080

atatttgaca ttgaggacca tcctgaggtg ccctgcccct atgactacat caagatcaaa   1140

gttggtccaa aagttttggg gcctttctgt ggagagaaag ccccagaacc catcagcacc   1200

cagagccaca gtgtcctgat cctgttccat agtgacaact cgggagagaa ccggggctgg   1260

aggctctcat acagggctgc aggaaatgag tgcccagagc tacagcctcc tgtccatggg   1320

aaaatcgagc cctcccaagc caagtatttc ttcaaagacc aagtgctcgt cagctgtgac   1380

acaggctaca aagtgctgaa ggataatgtg gagatggaca cattccagat tgagtgtctg   1440

aaggatggga cgtggagtaa caagattccc acctgtaaaa ttgtagactg tagagcccca   1500

ggagagctgg aacacgggct gatcaccttc tctacaagga acaacctcac cacatacaag   1560

tctgagatca aatactcctg tcaggagccc tattacaaga tgctcaacaa taacacaggt   1620

atatatacct gttctgccca aggagtctgg atgaataaag tattggggag aagcctaccc   1680

acctgccttc cagtgtgtgg gctccccaag ttctcccgga agctgatggc caggatcttc   1740
```

aatggacgcc cagcccagaa aggcaccact ccctggattg ccatgctgtc acacctgaat 1800
gggcagccct tctgcggagg ctcccttcta ggctccagct ggatcgtgac cgccgcacac 1860
tgcctccacc agtcactcga tccggaagat ccgaccctac gtgattcaga cttgctcagc 1920
ccttctgact tcaaaatcat cctgggcaag cattggaggc tccggtcaga tgaaaatgaa 1980
cagcatctcg gcgtcaaaca caccactctc cacccccagt atgatcccaa cacattcgag 2040
aatgacgtgg ctctggtgga gctgttggag agcccagtgc tgaatgcctt cgtgatgccc 2100
atctgtctgc ctgagggacc ccagcaggaa ggagccatgg tcatcgtcag cggctggggg 2160
aagcagttct tgcaaaggtt cccagagacc ctgatggaga ttgaaatccc gattgttgac 2220
cacagcacct gccagaaggc ttatgccccg ctgaagaaga aagtgaccag ggacatgatc 2280
tgtgctgggg agaaggaagg gggaaaggac gcctgtgcgg gtgactctgg aggccccatg 2340
gtgaccctga atagagaaag aggccagtgg tacctggtgg gcactgtgtc ctggggtgat 2400
gactgtggga agaaggaccg ctacggagta tactcttaca tccaccacaa caaggactgg 2460
atccagaggg tcaccggagt gaggaactga atttggctcc tcagccccag caccaccagc 2520
tgtgggcagt cagtagcaga ggacgatcct ccgatgaaag cagccatttc tcctttcctt 2580
cctcccatcc cccctccttc ggcctatcca ttactgggca atagagcagg tatcttcacc 2640 ccttttcac tctctttaaa gagatggagc aagagagtgg tcagaacaca ggccgaatcc 2700
aggctctatc acttactagt ttgcagtgct gggcaggtga cttcatctct tcgaacttca 2760
gtttcttcat aagatggaaa tgctatacct tacctacctc gtaaaagtct gatgaggaaa 2820
agattaacta atagatgcat agcacttaac agagtgcata gcatacactg ttttcaataa 2880
atgcacctta gcagaaggtc gatgtgtcta ccaggcagac gaagctctct tacaaacccc 2940
tgcctgggtc ttagcattga tcagtgacac acctctcccc tcaaccttga ccatctccat 3000
ctgcccttaa atgctgtatg ctttttttgcc accgtgcaac ttgcccaaca tcaatcttca 3060
ccctcatccc taaaaaagta aaacagacaa ggttctgagt cctgtggtat gtcccctagc 3120
aaatgtaact aggaacatgc actagatgac agattgcggg agggcctgag agaagcaggg 3180
acaggaggga gcctggggat tgtggtttgg gaaggcagac acctggttct agaactagct 3240
ctgcccttag ccccctgtat gaccctatgc aagtcctcct ccctcatctc aaagggtcct 3300
caaagctctg acgatctaag atacaatgaa gccattttcc ccctgataag atgaggtaaa 3360
gccaatgtaa ccaaaaggca aaaattacaa tcggttcaaa ggaactttga tgcagacaaa 3420
atgctgctgc tgctgctcct gaaataccca cccctttcca ctacgggtgg gttcccaagg 3480
acatgggaca ggcaaagtgt gagccaaagg atccttcctt attcctaagc agagcatctg 3540
ctctgggccc tggcctcctt cccttcttgg gaaactgggc tgcatgaggt gggccctggt 3600
agtttgtacc ccaggcccct atactcttcc ttcctatgtc cacagctgac cccaagcagc 3660
cgttccccga ctcctcaccc ctgagcctca ccctgaactc cctcatcttg caaggccata 3720
agtgttttcc aagcaaaatg cctctcccat cctctctcag gaagcttcta gagactttat 3780
gccctccaga gctccaagat ataagccctc caagggatca gaagctccaa gttcctgtct 3840
tctgttttat agaaattgat cttccctggg ggactttaac tcttgacctg tatgcagctg 3900
ttggagtaat tccaggtctc ttgaaaaaaa agaggaagat aatggagaat gagaacatat 3960
atatatatat attaagcccc aggctgaata ctcagggaca gcaattcaca gcctgcctct 4020
ggttctataa acaagtcatt ctacctcttt gtgccctgct gtttattctg taaggggaag 4080

-continued

```
gtggcaatgg gacccagctc catcagacac ttgtcaagct agcagaaact ccattttcaa   4140
tgccaaagaa gaactgtaat gctgttttgg aatcatccca aggcatccca agacaccata   4200
tcttcccatt tcaagcactg cctgggcaca ccccaacatc ccaggctgtg gtggctcctg   4260
tgggaactac ctagatgaag agagtatcat ttataccttc taggagctcc tattgggaga   4320
catgaaacat atgtaattga ctaccatgta atagaacaaa ccctgccaag tgctgctttg   4380
gaaagtcatg gaggtaaaag aaagaccatt ctggtatgaa ggttttgggg gaggagatat   4440
caatcaagaa ggcttcccag aagaggtgac tggaccagag ccttgtccac aggtaagacg   4500
gaggaggcct tccacatgga gggagaacaa tagtaaatgt ccactcaaga tgtcctttat   4560
tataccagct cctcccacaa aaacacatgt ccagtggact ctttttctgg gatcagaacc   4620
aacaccaaaa agagcttttc tccttaaagt tagaattcta aacaggactt gaaatggcct   4680
caaggtttgt gcacaaatac tgacttctgg ctggacccag cttattctgt ttatttctcc   4740
aattgcaatt tcatccttat cctgagaaaa tgtctaaata ggccatggaa cccaggcttc   4800
cccgtgacct acaagcactt attagctgtg ccagctcctg cactgctgct aaggtccaag   4860
aaacccagat ctctcacaga gccatagaag cagagggctg gagtatctgt gaggacaaca   4920
accttgtcta acttcgcgac ctcattcttg agcatttcta ctgatgagaa actcactacc   4980
cccaattgca gctcattcaa ctttaaaatt gctgcttttt gaatcactga ttgtgaatat   5040
taatttaaaa aaataagtaa gaaaatgttt taaatgtgct gcctctttaa aaggtctcct   5100
ctttgtgcaa ccaaaaccca cctctctaga atacagtttg tataactgaa gctataattt   5160
cataccatga gtgctgctgt tagcaataat aatcatgccc ggattttatt aacaacagaa   5220
gctgttgctc gtatgaaaaa acaaacatta gttctaataa acatctgcat tgagtcaaag   5280
ctccctgttt gtttgtatgt cttttatgca ctgatgatta tagtgagttg ctttcattta   5340
ccaacatttt gttgtattcg tgtaggatca ctgtaccatg aagggagaga gactatgatg   5400
ggaagattgt tgtagataca aaagcatgtc ttaggttttt gggtcagttc tgtttaaata   5460
cctgtcctat tattcctgta aattatcaaa atatcccaga atgtcaatgt ttctgcatcc   5520
acattacaat tattaaatgc cactcattta ttaaatttac tattatcagt ggcatttaat   5580
aaatttgaat catatgttca gtgtttggtt tagaaaatat ggtgccatgt ctatgagtgg   5640
cctgttctgg attggagtac atgccttctt tctgccttga gttaatctta ctcaatggag   5700
aacaagaatc aaagaaacac caccaccaag aagcccttca agctagagtt gggcaagagt   5760
cagggagggg aatgtagacc actcatatga cagaggtgga aaccaatctt ggtctagaat   5820
aagtctcaaa atcaaaagac ttgaattcta gtgcagcgta ggttgactcc cttatttatt   5880
taattttccc atctctacac cgctagaata acctctctcc tgaggctgtt gaatctgatg   5940
aattagcaga taggaaagaa cttagaaaat tataagttca ctcaaatgta aaaggttata   6000
tgggaaataa tcaccactaa catttttgag tacttactat ctgcttgtta tacacattct   6060
ctaatttaat tttcacaaga aaattcatga aaggactata cttatccccc ttttacaggt   6120
gagcaacctg gagtgcagtg aagtgtaaaa tgtgggccga cttaggagca caaataccc   6180
agcaacaatg agcactctta gtacacaggt cttggtttct aaaatatcat catccgataa   6240
aaggaacaca ggctctttga agaaatgact gattccggga ttggggcaag aaacacacaa   6300
gctgagactg gagcatcttg cagtcccaga aagtgaagaa acgctgagga tatgtcaaag   6360
ggacacagga gccaaatgaa agagcttcca ctggccaaag ctggaatgtt gagcaacaaa   6420
gcaacatagc attggataat aacccaaagt ataaaataaa tattcatgag tacata       6476
```

<210> SEQ ID NO 2
<211> LENGTH: 699
<212> TYPE: PRT
<213> ORGANISM: Homo Sapiens

<400> SEQUENCE: 2

```
Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
        355                 360                 365

Ala Pro Gly Glu Leu Glu His Gly Leu Ile Thr Phe Ser Thr Arg Asn
```

```
    370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
                405                 410                 415

Gln Gly Val Trp Met Asn Lys Val Leu Gly Arg Ser Leu Pro Thr Cys
            420                 425                 430

Leu Pro Val Cys Gly Leu Pro Lys Phe Ser Arg Lys Leu Met Ala Arg
        435                 440                 445

Ile Phe Asn Gly Arg Pro Ala Gln Lys Gly Thr Thr Pro Trp Ile Ala
    450                 455                 460

Met Leu Ser His Leu Asn Gly Gln Pro Phe Cys Gly Gly Ser Leu Leu
465                 470                 475                 480

Gly Ser Ser Trp Ile Val Thr Ala Ala His Cys Leu His Gln Ser Leu
                485                 490                 495

Asp Pro Glu Asp Pro Thr Leu Arg Asp Ser Asp Leu Leu Ser Pro Ser
            500                 505                 510

Asp Phe Lys Ile Ile Leu Gly Lys His Trp Arg Leu Arg Ser Asp Glu
        515                 520                 525

Asn Glu Gln His Leu Gly Val Lys His Thr Thr Leu His Pro Gln Tyr
    530                 535                 540

Asp Pro Asn Thr Phe Glu Asn Asp Val Ala Leu Val Glu Leu Leu Glu
545                 550                 555                 560

Ser Pro Val Leu Asn Ala Phe Val Met Pro Ile Cys Leu Pro Glu Gly
                565                 570                 575

Pro Gln Gln Glu Gly Ala Met Val Ile Val Ser Gly Trp Gly Lys Gln
            580                 585                 590

Phe Leu Gln Arg Phe Pro Glu Thr Leu Met Glu Ile Glu Ile Pro Ile
        595                 600                 605

Val Asp His Ser Thr Cys Gln Lys Ala Tyr Ala Pro Leu Lys Lys Lys
    610                 615                 620

Val Thr Arg Asp Met Ile Cys Ala Gly Glu Lys Glu Gly Gly Lys Asp
625                 630                 635                 640

Ala Cys Ala Gly Asp Ser Gly Gly Pro Met Val Thr Leu Asn Arg Glu
                645                 650                 655

Arg Gly Gln Trp Tyr Leu Val Gly Thr Val Ser Trp Gly Asp Asp Cys
            660                 665                 670

Gly Lys Lys Asp Arg Tyr Gly Val Tyr Ser Tyr Ile His His Asn Lys
        675                 680                 685

Asp Trp Ile Gln Arg Val Thr Gly Val Arg Asn
    690                 695


<210> SEQ ID NO 3
<211> LENGTH: 2471
<212> TYPE: DNA
<213> ORGANISM: Homo Sapiens

<400> SEQUENCE: 3

agaccaggcc aggccagctg gacgggcaca ccatgaggct gctgaccctc ctgggccttc      60

tgtgtggctc ggtggccacc cccttgggcc cgaagtggcc tgaacctgtg ttcgggcgcc     120

tggcatcccc cggctttcca ggggagtatg ccaatgacca ggagcggcgc tggaccctga     180

ctgcaccccc cggctaccgc ctgcgcctct acttcaccca cttcgacctg gagctctccc     240

acctctgcga gtacgacttc gtcaagctga gctcgggggc caaggtgctg gccacgctgt     300
```

```
gcgggcagga gagcacagac acggagcggg cccctggcaa ggacactttc tactcgctgg    360
gctccagcct ggacattacc ttccgctccg actactccaa cgagaagccg ttcacggggt    420
tcgaggcctt ctatgcagcc gaggacattg acgagtgcca ggtggccccg ggagaggcgc    480
ccacctgcga ccaccactgc cacaaccacc tgggcggttt ctactgctcc tgccgcgcag    540
gctacgtcct gcaccgtaac aagcgcacct gctcagccct gtgctccggc caggtcttca    600
cccagaggtc tggggagctc agcagccctg aatacccacg gccgtatccc aaactctcca    660
gttgcactta cagcatcagc ctggaggagg ggttcagtgt cattctggac tttgtggagt    720
ccttcgatgt ggagacacac cctgaaaccc tgtgtcccta cgactttctc aagattcaaa    780
cagacagaga agaacatggc ccattctgtg ggaagacatt gccccacagg attgaaacaa    840
aaagcaacac ggtgaccatc acctttgtca cagatgaatc aggagaccac acaggctgga    900
agatccacta cacgagcaca gcgcagcctt gcccttatcc gatggcgcca cctaatggcc    960
acgtttcacc tgtgcaagcc aaatacatcc tgaaagacag cttctccatc ttttgcgaga   1020
ctggctatga gcttctgcaa ggtcacttgc ccctgaaatc ctttactgca gtttgtcaga   1080
aagatggatc ttgggaccgg ccaatgcccg cgtgcagcat tgttgactgt ggccctcctg   1140
atgatctacc cagtggccga gtggagtaca tcacaggtcc tggagtgacc acctacaaag   1200
ctgtgattca gtacagctgt gaagagacct tctacacaat gaaagtgaat gatggtaaat   1260
atgtgtgtga ggctgatgga ttctggacga gctccaaagg agaaaaatca ctcccagtct   1320
gtgagcctgt ttgtggacta tcagcccgca caacaggagg gcgtatatat ggagggcaaa   1380
aggcaaaacc tggtgatttt ccttggcaag tcctgatatt aggtggaacc acagcagcag   1440
gtgcactttt atatgacaac tgggtcctaa cagctgctca tgccgtctat gagcaaaaac   1500
atgatgcatc cgccctggac attcgaatgg gcaccctgaa aagactatca cctcattata   1560
cacaagcctg gtctgaagct gtttttatac atgaaggtta tactcatgat gctggctttg   1620
acaatgacat agcactgatt aaattgaata acaaagttgt aatcaatagc aacatcacgc   1680
ctatttgtct gccaagaaaa gaagctgaat cctttatgag gacagatgac attggaactg   1740
catctggatg ggggattaac caaaggggtt ttcttgctag aaatctaatg tatgtcgaca   1800
taccgattgt tgaccatcaa aaatgtactg ctgcatatga aaagccaccc tatccaaggg   1860
gaagtgtaac tgctaacatg ctttgtgctg gcttagaaag tgggggcaag gacagctgca   1920
gaggtgacag cggaggggca ctggtgtttc tagatagtga aacagagagg tggtttgtgg   1980
gaggaatagt gtcctggggt tccatgaatt gtggggaagc aggtcagtat ggagtctaca   2040
caaaagttat taactatatt ccctggatcg agaacataat tagtgatttt taacttgcgt   2100
gtctgcagtc aaggattctt catttttaga aatgcctgtg aagaccttgg cagcgacgtg   2160
gctcgagaag cattcatcat tactgtggac atggcagttg ttgctccacc caaaaaaaca   2220
gactccaggt gaggctgctg tcatttctcc acttgccagt ttaattccag ccttacccat   2280
tgactcaagg ggacataaac cacgagagtg acagtcatct ttgcccaccc agtgtaatgt   2340
cactgctcaa attacatttc attaccttaa aaagccagtc tcttttcata ctggctgttg   2400
gcatttctgt aaactgcctg tccatgctct ttgtttttaa acttgttctt attgaaaaaa   2460
aaaaaaaaaa a                                                        2471
```

<210> SEQ ID NO 4
<211> LENGTH: 686
<212> TYPE: PRT

<213> ORGANISM: Homo Sapiens

<400> SEQUENCE: 4

```
Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Ala Leu Cys Ser Gly Gln Val Phe Thr Gln Arg
            180                 185                 190

Ser Gly Glu Leu Ser Ser Pro Glu Tyr Pro Arg Pro Tyr Pro Lys Leu
        195                 200                 205

Ser Ser Cys Thr Tyr Ser Ile Ser Leu Glu Glu Gly Phe Ser Val Ile
    210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
            260                 265                 270

Thr Val Thr Ile Thr Phe Val Thr Asp Glu Ser Gly Asp His Thr Gly
        275                 280                 285

Trp Lys Ile His Tyr Thr Ser Thr Ala Gln Pro Cys Pro Tyr Pro Met
    290                 295                 300

Ala Pro Pro Asn Gly His Val Ser Pro Val Gln Ala Lys Tyr Ile Leu
305                 310                 315                 320

Lys Asp Ser Phe Ser Ile Phe Cys Glu Thr Gly Tyr Glu Leu Leu Gln
                325                 330                 335

Gly His Leu Pro Leu Lys Ser Phe Thr Ala Val Cys Gln Lys Asp Gly
            340                 345                 350

Ser Trp Asp Arg Pro Met Pro Ala Cys Ser Ile Val Asp Cys Gly Pro
        355                 360                 365

Pro Asp Asp Leu Pro Ser Gly Arg Val Glu Tyr Ile Thr Gly Pro Gly
    370                 375                 380

Val Thr Thr Tyr Lys Ala Val Ile Gln Tyr Ser Cys Glu Glu Thr Phe
385                 390                 395                 400
```

```
Tyr Thr Met Lys Val Asn Asp Gly Lys Tyr Val Cys Glu Ala Asp Gly
                405                 410                 415

Phe Trp Thr Ser Ser Lys Gly Glu Lys Ser Leu Pro Val Cys Glu Pro
            420                 425                 430

Val Cys Gly Leu Ser Ala Arg Thr Thr Gly Gly Arg Ile Tyr Gly Gly
        435                 440                 445

Gln Lys Ala Lys Pro Gly Asp Phe Pro Trp Gln Val Leu Ile Leu Gly
    450                 455                 460

Gly Thr Thr Ala Ala Gly Ala Leu Leu Tyr Asp Asn Trp Val Leu Thr
465                 470                 475                 480

Ala Ala His Ala Val Tyr Glu Gln Lys His Asp Ala Ser Ala Leu Asp
                485                 490                 495

Ile Arg Met Gly Thr Leu Lys Arg Leu Ser Pro His Tyr Thr Gln Ala
            500                 505                 510

Trp Ser Glu Ala Val Phe Ile His Glu Gly Tyr Thr His Asp Ala Gly
        515                 520                 525

Phe Asp Asn Asp Ile Ala Leu Ile Lys Leu Asn Asn Lys Val Val Ile
    530                 535                 540

Asn Ser Asn Ile Thr Pro Ile Cys Leu Pro Arg Lys Glu Ala Glu Ser
545                 550                 555                 560

Phe Met Arg Thr Asp Asp Ile Gly Thr Ala Ser Gly Trp Gly Leu Thr
                565                 570                 575

Gln Arg Gly Phe Leu Ala Arg Asn Leu Met Tyr Val Asp Ile Pro Ile
            580                 585                 590

Val Asp His Gln Lys Cys Thr Ala Ala Tyr Glu Lys Pro Pro Tyr Pro
        595                 600                 605

Arg Gly Ser Val Thr Ala Asn Met Leu Cys Ala Gly Leu Glu Ser Gly
    610                 615                 620

Gly Lys Asp Ser Cys Arg Gly Asp Ser Gly Gly Ala Leu Val Phe Leu
625                 630                 635                 640

Asp Ser Glu Thr Glu Arg Trp Phe Val Gly Gly Ile Val Ser Trp Gly
                645                 650                 655

Ser Met Asn Cys Gly Glu Ala Gly Gln Tyr Gly Val Tyr Thr Lys Val
            660                 665                 670

Ile Asn Tyr Ile Pro Trp Ile Glu Asn Ile Ile Ser Asp Phe
        675                 680                 685


<210> SEQ ID NO 5
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: Variant
<222> LOCATION: (1)..(1)
<223> OTHER INFORMATION: wherein Xaa at position 1 is Phe or Val
<220> FEATURE:
<221> NAME/KEY: Variant
<222> LOCATION: (4)..(4)
<223> OTHER INFORMATION: wherein Xaa at position 4 is Arg or Lys
<220> FEATURE:
<221> NAME/KEY: Variant
<222> LOCATION: (5)..(5)
<223> OTHER INFORMATION: wherein Xaa at position 5 is Lys or Leu
<220> FEATURE:
<221> NAME/KEY: Variant
<222> LOCATION: (6)..(6)
<223> OTHER INFORMATION: wherein Xaa at position 8 is Tyr or Trp
<220> FEATURE:
<221> NAME/KEY: Variant
```

<222> LOCATION: (8)..(8)
<223> OTHER INFORMATION: wherein Xaa at position 8 is Tyr or Asn

<400> SEQUENCE: 5

Xaa Cys Thr Xaa Xaa Xaa Cys Xaa Gln Val Lys Leu Trp Asn
1 5 10

<210> SEQ ID NO 6
<211> LENGTH: 36
<212> TYPE: PRT
<213> ORGANISM: Artificial Sequence
<220> FEATURE:
<223> OTHER INFORMATION: Synthetic

<400> SEQUENCE: 6

Leu Glu Val Thr Cys Glu Pro Gly Thr Thr Phe Lys Asp Lys Cys Asn
1 5 10 15

Thr Cys Arg Cys Gly Ser Asp Gly Lys Ser Ala Phe Cys Thr Arg Lys
20 25 30

Leu Cys Tyr Gln
35

<210> SEQ ID NO 7
<211> LENGTH: 33
<212> TYPE: PRT
<213> ORGANISM: Artificial Sequence
<220> FEATURE:
<223> OTHER INFORMATION: Synthetic

<400> SEQUENCE: 7

Thr Cys Glu Pro Gly Thr Thr Phe Lys Asp Lys Cys Asn Thr Cys Arg
1 5 10 15

Cys Gly Ser Asp Gly Lys Ser Ala Phe Cys Thr Arg Lys Leu Cys Tyr
20 25 30

Gln

<210> SEQ ID NO 8
<211> LENGTH: 20
<212> TYPE: PRT
<213> ORGANISM: Artificial Sequence
<220> FEATURE:
<223> OTHER INFORMATION: Synthetic

<400> SEQUENCE: 8

Thr Cys Arg Cys Gly Ser Asp Gly Lys Ser Ala Phe Cys Thr Arg Lys
1 5 10 15

Leu Cys Tyr Gln
20

<210> SEQ ID NO 9
<211> LENGTH: 36
<212> TYPE: PRT
<213> ORGANISM: Artificial Sequence
<220> FEATURE:
<223> OTHER INFORMATION: Synthetic

<400> SEQUENCE: 9

Leu Glu Val Thr Cys Glu Pro Gly Thr Thr Phe Lys Asp Lys Cys Asn
1 5 10 15

Thr Cys Arg Cys Gly Ser Asp Gly Lys Ser Ala Val Cys Thr Lys Leu
20 25 30

Trp Cys Asn Gln
35

<210> SEQ ID NO 10
<211> LENGTH: 33
<212> TYPE: PRT
<213> ORGANISM: Artificial Sequence
<220> FEATURE:
<223> OTHER INFORMATION: Synthetic

<400> SEQUENCE: 10

```
Thr Cys Glu Pro Gly Thr Thr Phe Lys Asp Lys Cys Asn Thr Cys Arg
1               5                   10                  15

Cys Gly Ser Asp Gly Lys Ser Ala Val Cys Thr Lys Leu Trp Cys Asn
            20                  25                  30

Gln
```

<210> SEQ ID NO 11
<211> LENGTH: 20
<212> TYPE: PRT
<213> ORGANISM: Artificial Sequence
<220> FEATURE:
<223> OTHER INFORMATION: Synthetic

<400> SEQUENCE: 11

```
Thr Cys Arg Cys Gly Ser Asp Gly Lys Ser Ala Val Cys Thr Lys Leu
1               5                   10                  15

Trp Cys Asn Gln
            20
```

<210> SEQ ID NO 12
<211> LENGTH: 227
<212> TYPE: PRT
<213> ORGANISM: Homo Sapiens

<400> SEQUENCE: 12

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13

Gly Thr Gly Gly Gly Ser Gly Ser Ser Ser Arg Ser
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic

<400> SEQUENCE: 14

Gly Thr Gly Gly Gly Ser Gly Ser Ser Ser
1               5                   10

<210> SEQ ID NO 15
<211> LENGTH: 888
<212> TYPE: DNA
<213> ORGANISM: Artificial Sequence
<220> FEATURE:
<223> OTHER INFORMATION: Synthetic

<400> SEQUENCE: 15
atgtacagga tgcaactcct gtcttgcatt gcactaagtc ttgcacttgt cacgaattcg 60
ctcgaggtga catgtgaacc cggtacgacg tttaaggata agtgcaacac atgtaggtgc 120
ggtagcgacg gcaaatcagc gttctgtacc cggaaattgt gctaccaggg aactggagga 180
gggtcggggt cctcgtcaag atctgacaaa actcacacat gcccaccgtg cccagcacct 240
gaactcctgg ggggaccgtc agtcttcctc ttccccccaa aacccaagga caccctcatg 300
atctcccgga cccctgaggt cacatgcgtg gtggtggacg tgagccacga agaccctgag 360
gtcaagttca actggtacgt ggacggcgtg gaggtgcata atgccaagac aaagccgcgg 420
gaggagcagt acaacagcac gtaccgtgtg gtcagcgtcc tcaccgtcct gcaccaggac 480
tggctgaatg gcaaggagta caagtgcaag gtctccaaca aagccctccc agcccccatc 540
gagaaaacca tctccaaagc caaagggcag ccccgagaac cacaggtgta caccctgccc 600
ccatcccggg aggagatgac caagaaccag gtcagcctga cctgcctggt caaaggcttc 660
tatcccagcg acatcgccgt ggagtgggag agcaatgggc agccggagaa caactacaag 720
accacgcctc ccgtgctgga ctccgacggc tccttcttcc tctacagcaa gctcaccgtg 780
gacaagagca ggtggcagca ggggaacgtc ttctcatgct ccgtgatgca cgaggctctg 840
cacaaccact acacgcagaa gagcctctcc ctgtctccgg gtaaatga 888

<210> SEQ ID NO 16
<211> LENGTH: 275
<212> TYPE: PRT

<213> ORGANISM: Artificial Sequence
<220> FEATURE:
<223> OTHER INFORMATION: Synthetic

<400> SEQUENCE: 16

```
Leu Glu Val Thr Cys Glu Pro Gly Thr Thr Phe Lys Asp Lys Cys Asn
1               5                   10                  15

Thr Cys Arg Cys Gly Ser Asp Gly Lys Ser Ala Phe Cys Thr Arg Lys
            20                  25                  30

Leu Cys Tyr Gln Gly Thr Gly Gly Gly Ser Gly Ser Ser Ser Arg Ser
        35                  40                  45

Asp Lys Thr His Thr Cys Pro Pro Cys Pro Ala Pro Glu Leu Leu Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser His
                85                  90                  95

Glu Asp Pro Glu Val Lys Phe Asn Trp Tyr Val Asp Gly Val Glu Val
            100                 105                 110

His Asn Ala Lys Thr Lys Pro Arg Glu Glu Gln Tyr Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Ala Leu Pro Ala Pro Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Arg Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Gln Gly Asn Val Phe Ser Cys Ser Val Met
                245                 250                 255

His Glu Ala Leu His Asn His Tyr Thr Gln Lys Ser Leu Ser Leu Ser
            260                 265                 270

Pro Gly Lys
        275
```

<210> SEQ ID NO 17
<211> LENGTH: 888
<212> TYPE: DNA
<213> ORGANISM: Artificial Sequence
<220> FEATURE:
<223> OTHER INFORMATION: Synthetic

<400> SEQUENCE: 17

```
atgtacagga tgcaactcct gtcttgcatt gcactaagtc ttgcacttgt cacgaattcg      60

ttggaagtga cgtgtgagcc cggaacgaca ttcaaagaca agtgcaatac ttgtcggtgc     120

ggttcagatg ggaaatcggc ggtctgcaca aagctctggt gtaaccaggg caccggtgga     180

gggtcgggat ccagctcaag atctgacaaa actcacacat gcccaccgtg cccagcacct     240

gaactcctgg ggggaccgtc agtcttcctc ttccccccaa aacccaagga caccctcatg     300
```

```
atctcccgga cccctgaggt cacatgcgtg gtggtggacg tgagccacga agaccctgag    360

gtcaagttca actggtacgt ggacggcgtg gaggtgcata atgccaagac aaagccgcgg    420

gaggagcagt acaacagcac gtaccgtgtg gtcagcgtcc tcaccgtcct gcaccaggac    480

tggctgaatg gcaaggagta caagtgcaag gtctccaaca aagccctccc agcccccatc    540

gagaaaacca tctccaaagc caaagggcag ccccgagaac cacaggtgta caccctgccc    600

ccatcccggg aggagatgac caagaaccag gtcagcctga cctgcctggt caaaggcttc    660

tatcccagcg acatcgccgt ggagtgggag agcaatgggc agccggagaa caactacaag    720

accacgcctc ccgtgctgga ctccgacggc tccttcttcc tctacagcaa gctcaccgtg    780

gacaagagca ggtggcagca ggggaacgtc ttctcatgct ccgtgatgca cgaggctctg    840

cacaaccact acacgcagaa gagcctctcc ctgtctccgg gtaaatga                888
```

```
<210> SEQ ID NO 18
<211> LENGTH: 275
<212> TYPE: PRT
<213> ORGANISM: Artificial Sequence
<220> FEATURE:
<223> OTHER INFORMATION: Synthetic

<400> SEQUENCE: 18

Leu Glu Val Thr Cys Glu Pro Gly Thr Thr Phe Lys Asp Lys Cys Asn
1               5                   10                  15

Thr Cys Arg Cys Gly Ser Asp Gly Lys Ser Ala Val Cys Thr Lys Leu
            20                  25                  30

Trp Cys Asn Gln Gly Thr Gly Gly Gly Ser Gly Ser Ser Ser Arg Ser
        35                  40                  45

Asp Lys Thr His Thr Cys Pro Pro Cys Pro Ala Pro Glu Leu Leu Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser His
                85                  90                  95

Glu Asp Pro Glu Val Lys Phe Asn Trp Tyr Val Asp Gly Val Glu Val
            100                 105                 110

His Asn Ala Lys Thr Lys Pro Arg Glu Glu Gln Tyr Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Ala Leu Pro Ala Pro Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Arg Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Gln Gly Asn Val Phe Ser Cys Ser Val Met
                245                 250                 255
```

-continued

```
His Glu Ala Leu His Asn His Tyr Thr Gln Lys Ser Leu Ser Leu Ser
            260                 265                 270

Pro Gly Lys
        275


<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19

ctactgcgcc aaactcgagg tgacatgtga                                    30


<210> SEQ ID NO 20
<211> LENGTH: 30
<212> TYPE: DNA
<213> ORGANISM: Artificial Sequence
<220> FEATURE:
<223> OTHER INFORMATION: Synthetic

<400> SEQUENCE: 20

cgtggcccca tgcctggtag cacaatttcc                                    30


<210> SEQ ID NO 21
<211> LENGTH: 30
<212> TYPE: DNA
<213> ORGANISM: Artificial Sequence
<220> FEATURE:
<223> OTHER INFORMATION: Synthetic

<400> SEQUENCE: 21

cgggggtggc agcttggaag tgacgtgtga                                    30


<210> SEQ ID NO 22
<211> LENGTH: 30
<212> TYPE: DNA
<213> ORGANISM: Artificial Sequence
<220> FEATURE:
<223> OTHER INFORMATION: Synthetic

<400> SEQUENCE: 22

agccataata gtactggtta caccagagct                                    30


<210> SEQ ID NO 23
<211> LENGTH: 125
<212> TYPE: PRT
<213> ORGANISM: Chicken

<400> SEQUENCE: 23

Ala Val Thr Leu Asp Glu Ser Gly Gly Gly Leu Gln Thr Pro Gly Arg
1               5                   10                  15

Ala Leu Ser Leu Val Cys Lys Ala Ser Gly Phe Thr Phe Ser Ser Tyr
            20                  25                  30

Asn Met Gly Trp Val Arg Gln Ala Pro Gly Lys Gly Leu Glu Phe Val
        35                  40                  45

Ala Gly Ile Asp Asn Thr Gly Arg Tyr Thr Gly Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95
```

```
Ala Lys Ala Ala Gly Gly Ser Gly Tyr Cys Gly Ser Gly Ala Tyr Ile
            100                 105                 110

Asp Ala Trp Gly His Gly Thr Glu Val Ile Val Ser Ser
        115                 120                 125


<210> SEQ ID NO 24
<211> LENGTH: 30
<212> TYPE: PRT
<213> ORGANISM: Chicken
<220> FEATURE:
<221> NAME/KEY: Variant
<222> LOCATION: (16)..(16)
<223> OTHER INFORMATION: wherein Xaa at position 16 is Arg or Gly

<400> SEQUENCE: 24

Ala Val Thr Leu Asp Glu Ser Gly Gly Gly Leu Gln Thr Pro Gly Xaa
1               5                   10                  15

Ala Leu Ser Leu Val Cys Lys Ala Ser Gly Phe Thr Phe Ser
            20                  25                  30


<210> SEQ ID NO 25
<211> LENGTH: 14
<212> TYPE: PRT
<213> ORGANISM: Chicken
<220> FEATURE:
<221> NAME/KEY: Variant
<222> LOCATION: (12)..(12)
<223> OTHER INFORMATION: wherein Xaa at position 12 is Phe or Trp

<400> SEQUENCE: 25

Trp Val Arg Gln Ala Pro Gly Lys Gly Leu Glu Xaa Val Ala
1               5                   10


<210> SEQ ID NO 26
<211> LENGTH: 32
<212> TYPE: PRT
<213> ORGANISM: Chicken
<220> FEATURE:
<221> NAME/KEY: Variant
<222> LOCATION: (13)..(13)
<223> OTHER INFORMATION: wherein Xaa at position 13 is Val or Leu
<220> FEATURE:
<221> NAME/KEY: Variant
<222> LOCATION: (31)..(31)
<223> OTHER INFORMATION: wherein Xaa at position 31 is Ala or Thr

<400> SEQUENCE: 26

Arg Ala Thr Ile Ser Arg Asp Asn Gly Gln Ser Thr Xaa Arg Leu Gln
1               5                   10                  15

Leu Asn Asn Leu Arg Ala Glu Asp Thr Gly Ile Tyr Tyr Cys Xaa Lys
            20                  25                  30


<210> SEQ ID NO 27
<211> LENGTH: 5
<212> TYPE: PRT
<213> ORGANISM: Chicken
<220> FEATURE:
<221> NAME/KEY: Variant
<222> LOCATION: (4)..(4)
<223> OTHER INFORMATION: wherein Xaa at position 4 is Ala or Thr

<400> SEQUENCE: 27

Tyr Tyr Cys Xaa Lys
1               5


<210> SEQ ID NO 28
```

<211> LENGTH: 11
<212> TYPE: PRT
<213> ORGANISM: Chicken

<400> SEQUENCE: 28

Trp Gly His Gly Thr Glu Val Ile Val Ser Ser
1 5 10

<210> SEQ ID NO 29
<211> LENGTH: 5
<212> TYPE: PRT
<213> ORGANISM: Chicken

<400> SEQUENCE: 29

Trp Gly His Gly Thr
1 5

<210> SEQ ID NO 30
<211> LENGTH: 102
<212> TYPE: PRT
<213> ORGANISM: Chicken

<400> SEQUENCE: 30

Ala Leu Thr Gln Pro Ser Ser Val Ser Ala Asn Pro Gly Gly Thr Val
1 5 10 15

Lys Ile Thr Cys Ser Gly Asp Ser Ser Tyr Tyr Gly Trp Tyr Gln Gln
20 25 30

Lys Ala Pro Gly Ser Ala Pro Val Thr Val Ile Tyr Asp Asn Thr Asn
35 40 45

Arg Pro Ser Asn Ile Pro Ser Arg Phe Ser Gly Ser Lys Ser Gly Ser
50 55 60

Thr Ala Thr Leu Thr Ile Thr Gly Val Arg Ala Asp Asp Asn Ala Val
65 70 75 80

Tyr Tyr Cys Ala Ser Thr Asp Ser Ser Ser Thr Ala Phe Gly Ala Gly
85 90 95

Thr Thr Leu Thr Val Leu
100

<210> SEQ ID NO 31
<211> LENGTH: 20
<212> TYPE: PRT
<213> ORGANISM: Chicken
<220> FEATURE:
<221> NAME/KEY: Variant
<222> LOCATION: (6)..(6)
<223> OTHER INFORMATION: wherein Xaa at position 6 is Ala or Ser
<220> FEATURE:
<221> NAME/KEY: Variant
<222> LOCATION: (12)..(12)
<223> OTHER INFORMATION: wherein Xaa at position 12 is Leu or Pro
<220> FEATURE:
<221> NAME/KEY: Variant
<222> LOCATION: (14)..(14)
<223> OTHER INFORMATION: wherein Xaa at position 14 is Gly or Glu

<400> SEQUENCE: 31

Ala Leu Thr Gln Pro Xaa Ser Val Ser Ala Asn Xaa Gly Xaa Thr Val
1 5 10 15

Lys Ile Thr Cys
20

<210> SEQ ID NO 32
<211> LENGTH: 5
<212> TYPE: PRT

```
<213> ORGANISM: Chicken

<400> SEQUENCE: 32

Val Lys Ile Thr Cys
1               5


<210> SEQ ID NO 33
<211> LENGTH: 16
<212> TYPE: PRT
<213> ORGANISM: Chicken
<220> FEATURE:
<221> NAME/KEY: Variant
<222> LOCATION: (6)..(6)
<223> OTHER INFORMATION: wherein Xaa at position 6 is Ala or Ser
<220> FEATURE:
<221> NAME/KEY: Variant
<222> LOCATION: (14)..(14)
<223> OTHER INFORMATION: wherein Xaa at position 14 is Val or Leu

<400> SEQUENCE: 33

Trp Tyr Gln Gln Lys Xaa Pro Gly Ser Ala Pro Val Thr Xaa Ile Tyr
1               5                   10                  15


<210> SEQ ID NO 34
<211> LENGTH: 5
<212> TYPE: PRT
<213> ORGANISM: Chicken

<400> SEQUENCE: 34

Trp Tyr Gln Gln Lys
1               5


<210> SEQ ID NO 35
<211> LENGTH: 32
<212> TYPE: PRT
<213> ORGANISM: Chicken
<220> FEATURE:
<221> NAME/KEY: Variant
<222> LOCATION: (1)..(1)
<223> OTHER INFORMATION: wherein Xaa at position 1 is Asn or Asp
<220> FEATURE:
<221> NAME/KEY: Variant
<222> LOCATION: (10)..(10)
<223> OTHER INFORMATION: wherein Xaa at position 10 is Lys or Leu
<220> FEATURE:
<221> NAME/KEY: Variant
<222> LOCATION: (15)..(15)
<223> OTHER INFORMATION: wherein Xaa at position 15 is Ala or Asn
<220> FEATURE:
<221> NAME/KEY: Variant
<222> LOCATION: (27)..(27)
<223> OTHER INFORMATION: wherein Xaa at position 27 is Asn or Glu
<220> FEATURE:
<221> NAME/KEY: Variant
<222> LOCATION: (31)..(31)
<223> OTHER INFORMATION: Wherein Xaa at position 31 is Tyr or Phe

<400> SEQUENCE: 35

Xaa Ile Pro Ser Arg Phe Ser Gly Ser Xaa Ser Gly Ser Thr Xaa Thr
1               5                   10                  15

Leu Thr Ile Thr Gly Val Arg Ala Asp Asp Xaa Ala Val Tyr Xaa Cys
            20                  25                  30


<210> SEQ ID NO 36
<211> LENGTH: 10
<212> TYPE: PRT
<213> ORGANISM: Chicken

<400> SEQUENCE: 36
```

```
Phe Gly Ala Gly Thr Thr Leu Thr Val Leu
1               5                   10


<210> SEQ ID NO 37
<211> LENGTH: 6
<212> TYPE: PRT
<213> ORGANISM: Artificial Sequence
<220> FEATURE:
<223> OTHER INFORMATION: Synthetic

<400> SEQUENCE: 37

Ala Ala Gly Gly Ser Gly
1               5


<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

Ala Ala Gly Gly Ser Gly Gly Ser Gly Ala
1               5                   10


<210> SEQ ID NO 39
<211> LENGTH: 4
<212> TYPE: PRT
<213> ORGANISM: Artificial Sequence
<220> FEATURE:
<223> OTHER INFORMATION: Synthetic

<400> SEQUENCE: 39

Tyr Ile Asp Ala
1


<210> SEQ ID NO 40
<211> LENGTH: 5
<212> TYPE: PRT
<213> ORGANISM: Artificial Sequence
<220> FEATURE:
<223> OTHER INFORMATION: Synthetic

<400> SEQUENCE: 40

Ala Tyr Ile Asp Ala
1               5


<210> SEQ ID NO 41
<211> LENGTH: 14
<212> TYPE: PRT
<213> ORGANISM: Artificial Sequence
<220> FEATURE:
<223> OTHER INFORMATION: Synthetic

<400> SEQUENCE: 41

Gly Thr Gly Gly Gly Ser Gly Ser Ser Ser Tyr Ile Asp Ala
1               5                   10


<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Gly Ser Gly Ala Tyr Ile Asp Ala
```

1 5

<210> SEQ ID NO 43
<211> LENGTH: 14
<212> TYPE: PRT
<213> ORGANISM: Artificial Sequence
<220> FEATURE:
<223> OTHER INFORMATION: Synthetic

<400> SEQUENCE: 43

Ala Ala Gly Gly Ser Gly Gly Ser Gly Ala Tyr Ile Asp Ala
1 5 10

<210> SEQ ID NO 44
<211> LENGTH: 5
<212> TYPE: PRT
<213> ORGANISM: Artificial Sequence
<220> FEATURE:
<223> OTHER INFORMATION: Synthetic

<400> SEQUENCE: 44

Ser Gly Gly Gly Ser
1 5

<210> SEQ ID NO 45
<211> LENGTH: 4
<212> TYPE: PRT
<213> ORGANISM: Artificial Sequence
<220> FEATURE:
<223> OTHER INFORMATION: Synthetic

<400> SEQUENCE: 45

Tyr Tyr Tyr Gly
1

<210> SEQ ID NO 46
<211> LENGTH: 4
<212> TYPE: PRT
<213> ORGANISM: Artificial Sequence
<220> FEATURE:
<223> OTHER INFORMATION: Synthetic

<400> SEQUENCE: 46

Gly Ser Gly Ala
1

<210> SEQ ID NO 47
<211> LENGTH: 330
<212> TYPE: PRT
<213> ORGANISM: Homo Sapiens

<400> SEQUENCE: 47

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 48
<211> LENGTH: 106
<212> TYPE: PRT
<213> ORGANISM: Homo Sapiens

<400> SEQUENCE: 48

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 49
<211> LENGTH: 1488
<212> TYPE: DNA
```

<213> ORGANISM: Artificial Sequence
<220> FEATURE:
<223> OTHER INFORMATION: Synthetic

<400> SEQUENCE: 49
atggagttcg gcctgagctg gctgttcctg gtggccatcc ttaagggcgt gcagtgcgcc 60
gtgacgttgg acgagtccgg gggcggcctc cagacgcccg ggggagcgct cagcctcgtc 120
tgcaaggcct ccgggttcac cttcagcagt aacgccatgg gttgggtgcg acaggcgccc 180
ggcaaggggc tggagtgggt cgctggtatt gatgatgatg gtagtggcac aagatacgcg 240
ccggcggtga agggccgtgc caccatctcg agggacaacg ggcagagcac actgaggctg 300
cagctgaaca acctcagggc tgaggacacc ggcacctact actgcgccaa actcgaggtg 360
acatgtgaac ccggtacgac gtttaaggat aagtgcaaca catgtaggtg cggtagcgac 420
ggcaaatcag cgttctgtac ccggaaattg tgctaccagg catggggcca cgggaccgaa 480
gtcatcgtct cctccgctag caccaagggc ccatcggtct tccccctggc accctcctcc 540
aagagcacct ctgggggcac agcggccctg ggctgcctgg tcaaggacta cttccccgaa 600
ccggtgacgg tgtcgtggaa ctcaggcgcc ctgaccagcg gcgtgcacac cttcccggct 660
gtcctacagt cctcaggact ctactccctc agcagcgtgg tgaccgtgcc ctccagcagc 720
ttgggcaccc agacctacat ctgcaacgtg aatcacaagc ccagcaacac caaggtggac 780
aagaaagttg agcccaaatc ttgtgacaaa actcacacat gcccaccgtg cccagcacct 840
gaactcctgg ggggaccgtc agtcttcctc ttccccccaa aacccaagga caccctcatg 900
atctcccgga cccctgaggt cacatgcgtg gtggtggacg tgagccacga agaccctgag 960
gtcaagttca actggtacgt ggacggcgtg gaggtgcata atgccaagac aaagccgcgg 1020
gaggagcagt acaacagcac gtaccgtgtg gtcagcgtcc tcaccgtcct gcaccaggac 1080
tggctgaatg gcaaggagta caagtgcaag gtctccaaca aagccctccc agcccccatc 1140
gagaaaacca tctccaaagc caaagggcag ccccgagaac cacaggtgta caccctgccc 1200
ccatcccggg atgagctgac caagaaccag gtcagcctga cctgcctggt caaaggcttc 1260
tatcccagcg acatcgccgt ggagtgggag agcaatgggc agccggagaa caactacaag 1320
accacgcctc ccgtgctgga ctccgacggc tccttcttcc tctacagcaa gctcaccgtg 1380
gacaagagca ggtggcagca ggggaacgtc ttctcatgct ccgtgatgca tgaggctctg 1440
cacaaccact acacacagaa gagcctctcc ctgtctccgg gtaaatga 1488

<210> SEQ ID NO 50
<211> LENGTH: 476
<212> TYPE: PRT
<213> ORGANISM: Artificial Sequence
<220> FEATURE:
<223> OTHER INFORMATION: Synthetic

<400> SEQUENCE: 50

Ala Val Thr Leu Asp Glu Ser Gly Gly Gly Leu Gln Thr Pro Gly Gly
1 5 10 15

Ala Leu Ser Leu Val Cys Lys Ala Ser Gly Phe Thr Phe Ser Ser Asn
20 25 30

Ala Met Gly Trp Val Arg Gln Ala Pro Gly Lys Gly Leu Glu Trp Val
35 40 45

Ala Gly Ile Asp Asp Asp Gly Ser Gly Thr Arg Tyr Ala Pro Ala Val
50 55 60

Lys Gly Arg Ala Thr Ile Ser Arg Asp Asn Gly Gln Ser Thr Leu Arg

-continued

```
65                  70                  75                  80

Leu Gln Leu Asn Asn Leu Arg Ala Glu Asp Thr Gly Thr Tyr Tyr Cys
                85                  90                  95

Ala Lys Leu Glu Val Thr Cys Glu Pro Gly Thr Thr Phe Lys Asp Lys
            100                 105                 110

Cys Asn Thr Cys Arg Cys Gly Ser Asp Gly Lys Ser Ala Phe Cys Thr
        115                 120                 125

Arg Lys Leu Cys Tyr Gln Ala Trp Gly His Gly Thr Glu Val Ile Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 51
```

<211> LENGTH: 1479
<212> TYPE: DNA
<213> ORGANISM: Artificial Sequence
<220> FEATURE:
<223> OTHER INFORMATION: Synthetic

<400> SEQUENCE: 51
atggagttcg gcctgagctg gctgttcctg gtggccatcc ttaagggcgt gcagtgcgcc 60
gtgacgttgg acgagtccgg gggcggcctc cagacgcccg ggggagcgct cagcctcgtc 120
tgcaaggcct ccgggttcac cttcagcagt aacgccatgg gttgggtgcg acaggcgccc 180
ggcaaggggc tggagtgggt cgctggtatt gatgatgatg gtagtggcac aagatacgcg 240
ccggcggtga agggccgtgc caccatctcg agggacaacg ggcagagcac actgaggctg 300
cagctgaaca acctcagggc tgaggacacc ggcacctact actgcgccaa aacatgtgaa 360
cccggtacga cgtttaagga taagtgcaac acatgtaggt gcggtagcga cggcaaatca 420
gcgttctgta cccggaaatt gtgctaccag gcatggggcc acgggaccga agtcatcgtc 480
tcctccgcta gcaccaaggg cccatcggtc ttcccctgg caccctcctc caagagcacc 540
tctgggggca cagcggccct gggctgcctg gtcaaggact acttccccga accggtgacg 600
gtgtcgtgga actcaggcgc cctgaccagc ggcgtgcaca ccttcccggc tgtcctacag 660
tcctcaggac tctactccct cagcagcgtg gtgaccgtgc cctccagcag cttgggcacc 720
cagacctaca tctgcaacgt gaatcacaag cccagcaaca ccaaggtgga caagaaagtt 780
gagcccaaat cttgtgacaa aactcacaca tgcccaccgt gcccagcacc tgaactcctg 840
gggggaccgt cagtcttcct cttcccccca aaacccaagg acaccctcat gatctcccgg 900
acccctgagg tcacatgcgt ggtggtggac gtgagccacg aagaccctga ggtcaagttc 960
aactggtacg tggacggcgt ggaggtgcat aatgccaaga caaagccgcg ggaggagcag 1020
tacaacagca cgtaccgtgt ggtcagcgtc ctcaccgtcc tgcaccagga ctggctgaat 1080
ggcaaggagt acaagtgcaa ggtctccaac aaagccctcc cagcccccat cgagaaaacc 1140
atctccaaag ccaaagggca gccccgagaa ccacaggtgt acaccctgcc cccatcccgg 1200
gatgagctga ccaagaacca ggtcagcctg acctgcctgg tcaaaggctt ctatcccagc 1260
gacatcgccg tggagtggga gagcaatggg cagccggaga acaactacaa gaccacgcct 1320
cccgtgctgg actccgacgg ctccttcttc ctctacagca agctcaccgt ggacaagagc 1380
aggtggcagc aggggaacgt cttctcatgc tccgtgatgc atgaggctct gcacaaccac 1440
tacacacaga agagcctctc cctgtctccg ggtaaatga 1479

<210> SEQ ID NO 52
<211> LENGTH: 473
<212> TYPE: PRT
<213> ORGANISM: Artificial Sequence
<220> FEATURE:
<223> OTHER INFORMATION: Synthetic

<400> SEQUENCE: 52

Ala Val Thr Leu Asp Glu Ser Gly Gly Gly Leu Gln Thr Pro Gly Gly
1 5 10 15

Ala Leu Ser Leu Val Cys Lys Ala Ser Gly Phe Thr Phe Ser Ser Asn
20 25 30

Ala Met Gly Trp Val Arg Gln Ala Pro Gly Lys Gly Leu Glu Trp Val
35 40 45

Ala Gly Ile Asp Asp Asp Gly Ser Gly Thr Arg Tyr Ala Pro Ala Val
50 55 60

```
Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Thr Cys Glu Pro Gly Thr Thr Phe Lys Asp Lys Cys Asn Thr
            100                 105                 110

Cys Arg Cys Gly Ser Asp Gly Lys Ser Ala Phe Cys Thr Arg Lys Leu
        115                 120                 125

Cys Tyr Gln Ala Trp Gly His Gly Thr Glu Val Ile Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

<210> SEQ ID NO 53
<211> LENGTH: 1440
<212> TYPE: DNA
<213> ORGANISM: Artificial Sequence
<220> FEATURE:
<223> OTHER INFORMATION: Synthetic

<400> SEQUENCE: 53

```
atggagttcg gcctgagctg gctgttcctg gtggccatcc ttaagggcgt gcagtgcgcc     60

gtgacgttgg acgagtccgg gggcggcctc cagacgcccg ggggagcgct cagcctcgtc    120

tgcaaggcct ccgggttcac cttcagcagt aacgccatgg gttgggtgcg acaggcgccc    180

ggcaaggggc tggagtgggt cgctggtatt gatgatgatg gtagtggcac aagatacgcg    240

ccggcggtga agggccgtgc caccatctcg agggacaacg ggcagagcac actgaggctg    300

cagctgaaca acctcagggc tgaggacacc ggcacctact actgcgccaa aacatgtagg    360

tgcggtagcg acggcaaatc agcgttctgt acccggaaat tgtgctacca ggcatggggc    420

cacgggaccg aagtcatcgt ctcctccgct agcaccaagg gcccatcggt cttccccctg    480

gcaccctcct ccaagagcac ctctgggggc acagcggccc tgggctgcct ggtcaaggac    540

tacttccccg aaccggtgac ggtgtcgtgg aactcaggcg ccctgaccag cggcgtgcac    600

accttcccgg ctgtcctaca gtcctcagga ctctactccc tcagcagcgt ggtgaccgtg    660

ccctccagca gcttgggcac ccagacctac atctgcaacg tgaatcacaa gcccagcaac    720

accaaggtgg acaagaaagt tgagcccaaa tcttgtgaca aaactcacac atgcccaccg    780

tgcccagcac ctgaactcct ggggggaccg tcagtcttcc tcttcccccc aaaacccaag    840

gacaccctca tgatctcccg gacccctgag gtcacatgcg tggtggtgga cgtgagccac    900

gaagaccctg aggtcaagtt caactggtac gtggacggcg tggaggtgca taatgccaag    960

acaaagccgc gggaggagca gtacaacagc acgtaccgtg tggtcagcgt cctcaccgtc   1020

ctgcaccagg actggctgaa tggcaaggag tacaagtgca aggtctccaa caaagccctc   1080

ccagccccca tcgagaaaac catctccaaa gccaaagggc agccccgaga accacaggtg   1140

tacaccctgc ccccatcccg ggatgagctg accaagaacc aggtcagcct gacctgcctg   1200

gtcaaaggct tctatcccag cgacatcgcc gtggagtggg agagcaatgg gcagccggag   1260

aacaactaca agaccacgcc tcccgtgctg gactccgacg gctccttctt cctctacagc   1320

aagctcaccg tggacaagag caggtggcag caggggaacg tcttctcatg ctccgtgatg   1380

catgaggctc tgcacaacca ctacacacag aagagcctct ccctgtctcc gggtaaatga   1440
```

<210> SEQ ID NO 54
<211> LENGTH: 460
<212> TYPE: PRT
<213> ORGANISM: Artificial Sequence
<220> FEATURE:
<223> OTHER INFORMATION: Synthetic

<400> SEQUENCE: 54

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60
```

```
Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Thr Cys Arg Cys Gly Ser Asp Gly Lys Ser Ala Phe Cys Thr
            100                 105                 110

Arg Lys Leu Cys Tyr Gln Ala Trp Gly His Gly Thr Glu Val Ile Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460
```

<210> SEQ ID NO 55
<211> LENGTH: 1527

<212> TYPE: DNA
<213> ORGANISM: Artificial Sequence
<220> FEATURE:
<223> OTHER INFORMATION: Synthetic

<400> SEQUENCE: 55
atggagttcg gcctgagctg gctgttcctg gtggccatcc ttaagggcgt gcagtgcgcc 60
gtgacgttgg acgagtccgg gggcggcctc cagacgcccg gggggagcgct cagcctcgtc 120 tgcaaggcct ccgggttcac cttcagcagt aacgccatgg gttgggtgcg acaggcgccc 180
ggcaaggggc tggagtgggt cgctggtatt gatgatgatg gtagtggcac aagatacgcg 240
ccggcggtga agggccgtgc caccatctcg agggacaacg ggcagagcac actgaggctg 300
cagctgaaca acctcagggc tgaggacacc ggcacctact actgcgccaa actcgaggtg 360
acatgtgaac ccggtacgac gtttaaggat aagtgcaaca catgtaggtg cggtagcgac 420
ggcaaatcag cgttctgtac ccggaaattg tgctaccagg gaactggagg agggtcgggg 480
tcctcgtcat atatcgacgc atggggccac gggaccgaag tcatcgtctc ctccgctagc 540
accaagggcc catcggtctt ccccctggca ccctcctcca agagcacctc tgggggcaca 600
gcggccctgg gctgcctggt caaggactac ttccccgaac cggtgacggt gtcgtggaac 660
tcaggcgccc tgaccagcgg cgtgcacacc ttcccggctg tcctacagtc ctcaggactc 720
tactccctca gcagcgtggt gaccgtgccc tccagcagct tgggcaccca gacctacatc 780
tgcaacgtga atcacaagcc cagcaacacc aaggtggaca agaaagttga gcccaaatct 840
tgtgacaaaa ctcacacatg cccaccgtgc ccagcacctg aactcctggg gggaccgtca 900
gtcttcctct tccccccaaa acccaaggac accctcatga tctcccggac ccctgaggtc 960
acatgcgtgg tggtggacgt gagccacgaa gaccctgagg tcaagttcaa ctggtacgtg 1020
gacggcgtgg aggtgcataa tgccaagaca aagccgcggg aggagcagta caacagcacg 1080
taccgtgtgg tcagcgtcct caccgtcctg caccaggact ggctgaatgg caaggagtac 1140
aagtgcaagg tctccaacaa agccctccca gcccccatcg agaaaaccat ctccaaagcc 1200
aaagggcagc cccgagaacc acaggtgtac accctgcccc catcccggga tgagctgacc 1260
aagaaccagg tcagcctgac ctgcctggtc aaaggcttct atcccagcga catcgccgtg 1320
gagtgggaga gcaatgggca gccggagaac aactacaaga ccacgcctcc cgtgctggac 1380
tccgacggct ccttcttcct ctacagcaag ctcaccgtgg acaagagcag gtggcagcag 1440
gggaacgtct tctcatgctc cgtgatgcat gaggctctgc acaaccacta cacacagaag 1500
agcctctccc tgtctccggg taaatga 1527

<210> SEQ ID NO 56
<211> LENGTH: 489
<212> TYPE: PRT
<213> ORGANISM: Artificial Sequence
<220> FEATURE:
<223> OTHER INFORMATION: Synthetic

<400> SEQUENCE: 56

Ala Val Thr Leu Asp Glu Ser Gly Gly Gly Leu Gln Thr Pro Gly Gly
1 5 10 15

Ala Leu Ser Leu Val Cys Lys Ala Ser Gly Phe Thr Phe Ser Ser Asn
20 25 30

Ala Met Gly Trp Val Arg Gln Ala Pro Gly Lys Gly Leu Glu Trp Val
35 40 45

Ala Gly Ile Asp Asp Asp Gly Ser Gly Thr Arg Tyr Ala Pro Ala Val

```
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Leu Glu Val Thr Cys Glu Pro Gly Thr Thr Phe Lys Asp Lys
            100                 105                 110

Cys Asn Thr Cys Arg Cys Gly Ser Asp Gly Lys Ser Ala Phe Cys Thr
        115                 120                 125

Arg Lys Leu Cys Tyr Gln Gly Thr Gly Gly Gly Ser Gly Ser Ser Ser
    130                 135                 140

Tyr Ile Asp Ala Trp Gly His Gly Thr Glu Val Ile Val Ser Ser Ala
145                 150                 155                 160

Ser Thr Lys Gly Pro Ser Val Phe Pro Leu Ala Pro Ser Ser Lys Ser
                165                 170                 175

Thr Ser Gly Gly Thr Ala Ala Leu Gly Cys Leu Val Lys Asp Tyr Phe
            180                 185                 190

Pro Glu Pro Val Thr Val Ser Trp Asn Ser Gly Ala Leu Thr Ser Gly
        195                 200                 205

Val His Thr Phe Pro Ala Val Leu Gln Ser Ser Gly Leu Tyr Ser Leu
    210                 215                 220

Ser Ser Val Val Thr Val Pro Ser Ser Ser Leu Gly Thr Gln Thr Tyr
225                 230                 235                 240

Ile Cys Asn Val Asn His Lys Pro Ser Asn Thr Lys Val Asp Lys Lys
                245                 250                 255

Val Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
    370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480
```

Lys Ser Leu Ser Leu Ser Pro Gly Lys
485

<210> SEQ ID NO 57
<211> LENGTH: 1557
<212> TYPE: DNA
<213> ORGANISM: Artificial Sequence
<220> FEATURE:
<223> OTHER INFORMATION: Synthetic

<400> SEQUENCE: 57
atggagttcg gcctgagctg gctgttcctg gtggccatcc ttaagggcgt gcagtgcgcc 60
gtgacgttgg acgagtccgg gggcggcctc cagacgcccg gggagcgct cagcctcgtc 120 tgcaaggcct ccgggttcac cttcagcagt aacgccatgg gttgggtgcg acaggcgccc 180
ggcaaggggc tggagtgggt cgctggtatt gatgatgatg gtagtggcac aagatacgcg 240
ccggcggtga agggccgtgc caccatctcg agggacaacg ggcagagcac actgaggctg 300
cagctgaaca acctcagggc tgaggacacc ggcacctact actgcgccaa aggcaccggt 360
ggagggtcgg gatccagctc actcgaggtg acatgtgaac ccggtacgac gtttaaggat 420
aagtgcaaca catgtaggtg cggtagcgac ggcaaatcag cgttctgtac ccggaaattg 480
tgctaccagg gaactggagg agggtcgggg tcctcgtcat atatcgacgc atggggccac 540
gggaccgaag tcatcgtctc ctccgctagc accaagggcc catcggtctt ccccctggca 600
ccctcctcca agagcacctc tgggggcaca gcggccctgg gctgcctggt caaggactac 660
ttccccgaac cggtgacggt gtcgtggaac tcaggcgccc tgaccagcgg cgtgcacacc 720
ttcccggctg tcctacagtc ctcaggactc tactccctca gcagcgtggt gaccgtgccc 780
tccagcagct tgggcaccca gacctacatc tgcaacgtga atcacaagcc cagcaacacc 840
aaggtggaca agaaagttga gcccaaatct tgtgacaaaa ctcacacatg cccaccgtgc 900
ccagcacctg aactcctggg gggaccgtca gtcttcctct tccccccaaa acccaaggac 960
accctcatga tctcccggac ccctgaggtc acatgcgtgg tggtggacgt gagccacgaa 1020
gaccctgagg tcaagttcaa ctggtacgtg gacggcgtgg aggtgcataa tgccaagaca 1080
aagccgcggg aggagcagta caacagcacg taccgtgtgg tcagcgtcct caccgtcctg 1140
caccaggact ggctgaatgg caaggagtac aagtgcaagg tctccaacaa agccctccca 1200
gcccccatcg agaaaaccat ctccaaagcc aaagggcagc cccgagaacc acaggtgtac 1260
accctgcccc catcccggga tgagctgacc aagaaccagg tcagcctgac ctgcctggtc 1320
aaaggcttct atcccagcga catcgccgtg gagtgggaga gcaatgggca gccggagaac 1380
aactacaaga ccacgcctcc cgtgctggac tccgacggct ccttcttcct ctacagcaag 1440
ctcaccgtgg acaagagcag gtggcagcag gggaacgtct tctcatgctc cgtgatgcat 1500
gaggctctgc acaaccacta cacacagaag agcctctccc tgtctccggg taaatga 1557

<210> SEQ ID NO 58
<211> LENGTH: 499
<212> TYPE: PRT
<213> ORGANISM: Artificial Sequence
<220> FEATURE:
<223> OTHER INFORMATION: Synthetic

<400> SEQUENCE: 58

Ala Val Thr Leu Asp Glu Ser Gly Gly Gly Leu Gln Thr Pro Gly Gly
1 5 10 15

-continued

```
Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Gly Thr Gly Gly Gly Ser Gly Ser Ser Ser Leu Glu Val Thr
            100                 105                 110

Cys Glu Pro Gly Thr Thr Phe Lys Asp Lys Cys Asn Thr Cys Arg Cys
        115                 120                 125

Gly Ser Asp Gly Lys Ser Ala Phe Cys Thr Arg Lys Leu Cys Tyr Gln
    130                 135                 140

Gly Thr Gly Gly Gly Ser Gly Ser Ser Ser Tyr Ile Asp Ala Trp Gly
145                 150                 155                 160

His Gly Thr Glu Val Ile Val Ser Ser Ala Ser Thr Lys Gly Pro Ser
                165                 170                 175

Val Phe Pro Leu Ala Pro Ser Ser Lys Ser Thr Ser Gly Gly Thr Ala
            180                 185                 190

Ala Leu Gly Cys Leu Val Lys Asp Tyr Phe Pro Glu Pro Val Thr Val
        195                 200                 205

Ser Trp Asn Ser Gly Ala Leu Thr Ser Gly Val His Thr Phe Pro Ala
    210                 215                 220

Val Leu Gln Ser Ser Gly Leu Tyr Ser Leu Ser Ser Val Val Thr Val
225                 230                 235                 240

Pro Ser Ser Ser Leu Gly Thr Gln Thr Tyr Ile Cys Asn Val Asn His
                245                 250                 255

Lys Pro Ser Asn Thr Lys Val Asp Lys Lys Val Glu Pro Lys Ser Cys
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
```

-continued

```
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys


<210> SEQ ID NO 59
<211> LENGTH: 1545
<212> TYPE: DNA
<213> ORGANISM: Artificial Sequence
<220> FEATURE:
<223> OTHER INFORMATION: Synthetic

<400> SEQUENCE: 59

atggagttcg gcctgagctg gctgttcctg gtggccatcc ttaagggcgt gcagtgcgcc     60

gtgacgttgg acgagtccgg gggcggcctc cagacgcccg gggagcgct cagcctcgtc    120

tgcaaggcct ccgggttcac cttcagcagt aacgccatgg gttgggtgcg acaggcgccc    180

ggcaaggggc tggagtgggt cgctggtatt gatgatgatg gtagtggcac aagatacgcg    240

ccggcggtga agggccgtgc caccatctcg agggacaacg ggcagagcac actgaggctg    300

cagctgaaca acctcagggc tgaggacacc ggcacctact actgcgccaa agccgctggt    360

ggtagtggtc tcgaggtgac atgtgaaccc ggtacgacgt ttaaggataa gtgcaacaca    420

tgtaggtgcg gtagcgacgg caaatcagcg ttctgtaccc ggaaattgtg ctaccaggga    480

actggaggag ggtcggggtc ctcgtcatat atcgacgcat ggggccacgg gaccgaagtc    540

atcgtctcct ccgctagcac caagggccca tcggtcttcc ccctggcacc ctcctccaag    600

agcacctctg ggggcacagc ggccctgggc tgcctggtca aggactactt ccccgaaccg    660

gtgacggtgt cgtggaactc aggcgccctg accagcggcg tgcacacctt cccggctgtc    720

ctacagtcct caggactcta ctccctcagc agcgtggtga ccgtgccctc cagcagcttg    780

ggcacccaga cctacatctg caacgtgaat cacaagccca gcaacaccaa ggtggacaag    840

aaagttgagc ccaaatcttg tgacaaaact cacacatgcc caccgtgccc agcacctgaa    900

ctcctggggg gaccgtcagt cttcctcttc cccccaaaac ccaaggacac cctcatgatc    960

tcccggaccc ctgaggtcac atgcgtggtg gtggacgtga gccacgaaga ccctgaggtc   1020

aagttcaact ggtacgtgga cggcgtggag gtgcataatg ccaagacaaa gccgcgggag   1080

gagcagtaca acagcacgta ccgtgtggtc agcgtcctca ccgtcctgca ccaggactgg   1140

ctgaatggca aggagtacaa gtgcaaggtc tccaacaaag ccctcccagc ccccatcgag   1200

aaaaccatct ccaaagccaa agggcagccc cgagaaccac aggtgtacac cctgccccca   1260

tcccgggatg agctgaccaa gaaccaggtc agcctgacct gcctggtcaa aggcttctat   1320

cccagcgaca tcgccgtgga gtgggagagc aatgggcagc cggagaacaa ctacaagacc   1380

acgcctcccg tgctggactc cgacggctcc ttcttcctct acagcaagct caccgtggac   1440

aagagcaggt ggcagcaggg gaacgtcttc tcatgctccg tgatgcatga ggctctgcac   1500

aaccactaca cacagaagag cctctccctg tctccgggta aatga                   1545


<210> SEQ ID NO 60
<211> LENGTH: 495
<212> TYPE: PRT
```

<213> ORGANISM: Artificial Sequence
<220> FEATURE:
<223> OTHER INFORMATION: Synthetic

<400> SEQUENCE: 60

Ala Val Thr Leu Asp Glu Ser Gly Gly Gly Leu Gln Thr Pro Gly Gly
1 5 10 15

Ala Leu Ser Leu Val Cys Lys Ala Ser Gly Phe Thr Phe Ser Ser Asn
20 25 30

Ala Met Gly Trp Val Arg Gln Ala Pro Gly Lys Gly Leu Glu Trp Val
35 40 45

Ala Gly Ile Asp Asp Asp Gly Ser Gly Thr Arg Tyr Ala Pro Ala Val
50 55 60

Lys Gly Arg Ala Thr Ile Ser Arg Asp Asn Gly Gln Ser Thr Leu Arg
65 70 75 80

Leu Gln Leu Asn Asn Leu Arg Ala Glu Asp Thr Gly Thr Tyr Tyr Cys
85 90 95

Ala Lys Ala Ala Gly Gly Ser Gly Leu Glu Val Thr Cys Glu Pro Gly
100 105 110

Thr Thr Phe Lys Asp Lys Cys Asn Thr Cys Arg Cys Gly Ser Asp Gly
115 120 125

Lys Ser Ala Phe Cys Thr Arg Lys Leu Cys Tyr Gln Gly Thr Gly Gly
130 135 140

Gly Ser Gly Ser Ser Ser Tyr Ile Asp Ala Trp Gly His Gly Thr Glu
145 150 155 160

Val Ile Val Ser Ser Ala Ser Thr Lys Gly Pro Ser Val Phe Pro Leu
165 170 175

Ala Pro Ser Ser Lys Ser Thr Ser Gly Gly Thr Ala Ala Leu Gly Cys
180 185 190

Leu Val Lys Asp Tyr Phe Pro Glu Pro Val Thr Val Ser Trp Asn Ser
195 200 205

Gly Ala Leu Thr Ser Gly Val His Thr Phe Pro Ala Val Leu Gln Ser
210 215 220

Ser Gly Leu Tyr Ser Leu Ser Ser Val Val Thr Val Pro Ser Ser Ser
225 230 235 240

Leu Gly Thr Gln Thr Tyr Ile Cys Asn Val Asn His Lys Pro Ser Asn
245 250 255

Thr Lys Val Asp Lys Lys Val Glu Pro Lys Ser Cys Asp Lys Thr His
260 265 270

Thr Cys Pro Pro Cys Pro Ala Pro Glu Leu Leu Gly Gly Pro Ser Val
275 280 285

Phe Leu Phe Pro Pro Lys Pro Lys Asp Thr Leu Met Ile Ser Arg Thr
290 295 300

Pro Glu Val Thr Cys Val Val Val Asp Val Ser His Glu Asp Pro Glu
305 310 315 320

Val Lys Phe Asn Trp Tyr Val Asp Gly Val Glu Val His Asn Ala Lys
325 330 335

Thr Lys Pro Arg Glu Glu Gln Tyr Asn Ser Thr Tyr Arg Val Val Ser
340 345 350

Val Leu Thr Val Leu His Gln Asp Trp Leu Asn Gly Lys Glu Tyr Lys
355 360 365

Cys Lys Val Ser Asn Lys Ala Leu Pro Ala Pro Ile Glu Lys Thr Ile
370 375 380

Ser Lys Ala Lys Gly Gln Pro Arg Glu Pro Gln Val Tyr Thr Leu Pro

-continued

```
385                 390                 395                 400

Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Lys Leu Thr Val Asp Lys Ser Arg
    450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys
                485                 490                 495


<210> SEQ ID NO 61
<211> LENGTH: 1557
<212> TYPE: DNA
<213> ORGANISM: Artificial Sequence
<220> FEATURE:
<223> OTHER INFORMATION: Synthetic

<400> SEQUENCE: 61

atggagttcg gcctgagctg gctgttcctg gtggccatcc ttaagggcgt gcagtgcgcc      60

gtgacgttgg acgagtccgg gggcggcctc cagacgcccg gggggagcgct cagcctcgtc    120

tgcaaggcct ccgggttcac cttcagcagt aacgccatgg gttgggtgcg acaggcgccc     180

ggcaaggggc tggagtgggt cgctggtatt gatgatgatg gtagtggcac aagatacgcg     240

ccggcggtga agggccgtgc caccatctcg agggacaacg ggcagagcac actgaggctg     300

cagctgaaca acctcagggc tgaggacacc ggcacctact actgcgccaa agccgctggt     360

ggtagtggtg gtagtggtgc tctcgaggtg acatgtgaac ccggtacgac gtttaaggat     420

aagtgcaaca catgtaggtg cggtagcgac ggcaaatcag cgttctgtac ccggaaattg     480

tgctaccagg gaactggagg agggtcgggg tcctcgtcat atatcgacgc atggggccac     540

gggaccgaag tcatcgtctc ctccgctagc accaagggcc catcggtctt ccccctggca     600

ccctcctcca agagcacctc tgggggcaca gcggccctgg gctgcctggt caaggactac     660

ttccccgaac cggtgacggt gtcgtggaac tcaggcgccc tgaccagcgg cgtgcacacc     720

ttcccggctg tcctacagtc ctcaggactc tactccctca gcagcgtggt gaccgtgccc     780

tccagcagct tgggcaccca gacctacatc tgcaacgtga atcacaagcc cagcaacacc     840

aaggtggaca agaaagttga gcccaaatct tgtgacaaaa ctcacacatg cccaccgtgc     900

ccagcacctg aactcctggg gggaccgtca gtcttcctct tccccccaaa acccaaggac     960

accctcatga tctcccggac ccctgaggtc acatgcgtgg tggtggacgt gagccacgaa    1020

gaccctgagg tcaagttcaa ctggtacgtg gacggcgtgg aggtgcataa tgccaagaca    1080

aagccgcggg aggagcagta caacagcacg taccgtgtgg tcagcgtcct caccgtcctg    1140

caccaggact ggctgaatgg caaggagtac aagtgcaagg tctccaacaa agccctccca    1200

gcccccatcg agaaaaccat ctccaaagcc aaagggcagc cccgagaacc acaggtgtac    1260

accctgcccc catcccggga tgagctgacc aagaaccagg tcagcctgac ctgcctggtc    1320

aaaggcttct atcccagcga catcgccgtg gagtgggaga gcaatgggca gccggagaac    1380

aactacaaga ccacgcctcc cgtgctggac tccgacggct ccttcttcct ctacagcaag    1440

ctcaccgtgg acaagagcag gtggcagcag gggaacgtct tctcatgctc cgtgatgcat    1500
```

gaggctctgc acaaccacta cacacagaag agcctctccc tgtctccggg taaatga 1557

<210> SEQ ID NO 62
<211> LENGTH: 499
<212> TYPE: PRT
<213> ORGANISM: Artificial Sequence
<220> FEATURE:
<223> OTHER INFORMATION: Synthetic

<400> SEQUENCE: 62

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Ala Ala Gly Gly Ser Gly Gly Ser Gly Ala Leu Glu Val Thr
            100                 105                 110

Cys Glu Pro Gly Thr Thr Phe Lys Asp Lys Cys Asn Thr Cys Arg Cys
        115                 120                 125

Gly Ser Asp Gly Lys Ser Ala Phe Cys Thr Arg Lys Leu Cys Tyr Gln
    130                 135                 140

Gly Thr Gly Gly Gly Ser Gly Ser Ser Ser Tyr Ile Asp Ala Trp Gly
145                 150                 155                 160

His Gly Thr Glu Val Ile Val Ser Ser Ala Ser Thr Lys Gly Pro Ser
                165                 170                 175

Val Phe Pro Leu Ala Pro Ser Ser Lys Ser Thr Ser Gly Gly Thr Ala
            180                 185                 190

Ala Leu Gly Cys Leu Val Lys Asp Tyr Phe Pro Glu Pro Val Thr Val
        195                 200                 205

Ser Trp Asn Ser Gly Ala Leu Thr Ser Gly Val His Thr Phe Pro Ala
    210                 215                 220

Val Leu Gln Ser Ser Gly Leu Tyr Ser Leu Ser Ser Val Val Thr Val
225                 230                 235                 240

Pro Ser Ser Ser Leu Gly Thr Gln Thr Tyr Ile Cys Asn Val Asn His
                245                 250                 255

Lys Pro Ser Asn Thr Lys Val Asp Lys Lys Val Glu Pro Lys Ser Cys
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350
```

Arg Val Val Ser Val Leu Thr Val Leu His Gln Asp Trp Leu Asn Gly
355 360 365

Lys Glu Tyr Lys Cys Lys Val Ser Asn Lys Ala Leu Pro Ala Pro Ile
370 375 380

Glu Lys Thr Ile Ser Lys Ala Lys Gly Gln Pro Arg Glu Pro Gln Val
385 390 395 400

Tyr Thr Leu Pro Pro Ser Arg Asp Glu Leu Thr Lys Asn Gln Val Ser
405 410 415

Leu Thr Cys Leu Val Lys Gly Phe Tyr Pro Ser Asp Ile Ala Val Glu
420 425 430

Trp Glu Ser Asn Gly Gln Pro Glu Asn Asn Tyr Lys Thr Thr Pro Pro
435 440 445

Val Leu Asp Ser Asp Gly Ser Phe Phe Leu Tyr Ser Lys Leu Thr Val
450 455 460

Asp Lys Ser Arg Trp Gln Gln Gly Asn Val Phe Ser Cys Ser Val Met
465 470 475 480

His Glu Ala Leu His Asn His Tyr Thr Gln Lys Ser Leu Ser Leu Ser
485 490 495

Pro Gly Lys

<210> SEQ ID NO 63
<211> LENGTH: 1509
<212> TYPE: DNA
<213> ORGANISM: Artificial Sequence
<220> FEATURE:
<223> OTHER INFORMATION: Synthetic

<400> SEQUENCE: 63
atggagttcg gcctgagctg gctgttcctg gtggccatcc ttaagggcgt gcagtgcgcc 60
gtgacgttgg acgagtccgg gggcggcctc cagacgcccg gggggagcgct cagcctcgtc 120 tgcaaggcct ccgggttcac cttcagcagt aacgccatgg gttgggtgcg acaggcgccc 180
ggcaaggggc tggagtgggt cgctggtatt gatgatgatg gtagtggcac aagatacgcg 240
ccggcggtga agggccgtgc caccatctcg agggacaacg ggcagagcac actgaggctg 300
cagctgaaca acctcagggc tgaggacacc ggcacctact actgcgccaa actcgaggtg 360
acatgtgaac ccggtacgac gtttaaggat aagtgcaaca catgtaggtg cggtagcgac 420
ggcaaatcag cgttctgtac ccggaaattg tgctaccagg gtagtggtgc ttatatcgac 480
gcatggggcc acgggaccga agtcatcgtc tcctccgcta gcaccaaggg cccatcggtc 540 ttcccctgg caccctcctc caagagcacc tctgggggca cagcggccct gggctgcctg 600
gtcaaggact acttccccga accggtgacg gtgtcgtgga actcaggcgc cctgaccagc 660
ggcgtgcaca ccttcccggc tgtcctacag tcctcaggac tctactccct cagcagcgtg 720
gtgaccgtgc cctccagcag cttgggcacc cagacctaca tctgcaacgt gaatcacaag 780
cccagcaaca ccaaggtgga caagaaagtt gagcccaaat cttgtgacaa aactcacaca 840
tgcccaccgt gcccagcacc tgaactcctg gggggaccgt cagtcttcct cttcccccca 900
aaacccaagg acaccctcat gatctcccgg acccctgagg tcacatgcgt ggtggtggac 960
gtgagccacg aagaccctga ggtcaagttc aactggtacg tggacggcgt ggaggtgcat 1020
aatgccaaga caaagccgcg ggaggagcag tacaacagca cgtaccgtgt ggtcagcgtc 1080
ctcaccgtcc tgcaccagga ctggctgaat ggcaaggagt acaagtgcaa ggtctccaac 1140
aaagccctcc cagcccccat cgagaaaacc atctccaaag ccaaagggca gccccgagaa 1200

-continued

```
ccacaggtgt acaccctgcc cccatcccgg gatgagctga ccaagaacca ggtcagcctg   1260

acctgcctgg tcaaaggctt ctatcccagc gacatcgccg tggagtggga gagcaatggg   1320

cagccggaga acaactacaa gaccacgcct cccgtgctgg actccgacgg ctccttcttc   1380

ctctacagca agctcaccgt ggacaagagc aggtggcagc aggggaacgt cttctcatgc   1440

tccgtgatgc atgaggctct gcacaaccac tacacacaga agagcctctc cctgtctccg   1500

ggtaaatga                                                           1509


<210> SEQ ID NO 64
<211> LENGTH: 483
<212> TYPE: PRT
<213> ORGANISM: Artificial Sequence
<220> FEATURE:
<223> OTHER INFORMATION: Synthetic

<400> SEQUENCE: 64

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Leu Glu Val Thr Cys Glu Pro Gly Thr Thr Phe Lys Asp Lys
            100                 105                 110

Cys Asn Thr Cys Arg Cys Gly Ser Asp Gly Lys Ser Ala Phe Cys Thr
        115                 120                 125

Arg Lys Leu Cys Tyr Gln Gly Ser Gly Ala Tyr Ile Asp Ala Trp Gly
    130                 135                 140

His Gly Thr Glu Val Ile Val Ser Ser Ala Ser Thr Lys Gly Pro Ser
145                 150                 155                 160

Val Phe Pro Leu Ala Pro Ser Ser Lys Ser Thr Ser Gly Gly Thr Ala
                165                 170                 175

Ala Leu Gly Cys Leu Val Lys Asp Tyr Phe Pro Glu Pro Val Thr Val
            180                 185                 190

Ser Trp Asn Ser Gly Ala Leu Thr Ser Gly Val His Thr Phe Pro Ala
        195                 200                 205

Val Leu Gln Ser Ser Gly Leu Tyr Ser Leu Ser Ser Val Val Thr Val
    210                 215                 220

Pro Ser Ser Ser Leu Gly Thr Gln Thr Tyr Ile Cys Asn Val Asn His
225                 230                 235                 240

Lys Pro Ser Asn Thr Lys Val Asp Lys Lys Val Glu Pro Lys Ser Cys
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300
```

-continued

```
Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys
```

<210> SEQ ID NO 65
<211> LENGTH: 1539
<212> TYPE: DNA
<213> ORGANISM: Artificial Sequence
<220> FEATURE:
<223> OTHER INFORMATION: Synthetic

<400> SEQUENCE: 65

```
atggagttcg gcctgagctg gctgttcctg gtggccatcc ttaagggcgt gcagtgcgcc     60

gtgacgttgg acgagtccgg gggcggcctc cagacgcccg gggggagcgct cagcctcgtc   120

tgcaaggcct ccgggttcac cttcagcagt aacgccatgg gttgggtgcg acaggcgccc    180

ggcaaggggc tggagtgggt cgctggtatt gatgatgatg gtagtggcac aagatacgcg    240

ccggcggtga agggccgtgc caccatctcg agggacaacg ggcagagcac actgaggctg    300

cagctgaaca acctcagggc tgaggacacc ggcacctact actgcgccaa aggcaccggt    360

ggagggtcgg gatccagctc actcgaggtg acatgtgaac ccggtacgac gtttaaggat    420

aagtgcaaca catgtaggtg cggtagcgac ggcaaatcag cgttctgtac ccggaaattg    480

tgctaccagg gtagtggtgc ttatatcgac gcatggggcc acgggaccga agtcatcgtc    540

tcctccgcta gcaccaaggg cccatcggtc ttccccctgg caccctcctc caagagcacc    600

tctgggggca cagcggccct gggctgcctg gtcaaggact acttccccga accggtgacg    660

gtgtcgtgga actcaggcgc cctgaccagc ggcgtgcaca ccttcccggc tgtcctacag    720

tcctcaggac tctactccct cagcagcgtg gtgaccgtgc cctccagcag cttgggcacc    780

cagacctaca tctgcaacgt gaatcacaag cccagcaaca ccaaggtgga caagaaagtt    840

gagcccaaat cttgtgacaa aactcacaca tgcccaccgt gcccagcacc tgaactcctg    900

gggggaccgt cagtcttcct cttcccccca aaacccaagg acaccctcat gatctcccgg    960

acccctgagg tcacatgcgt ggtggtggac gtgagccacg aagaccctga ggtcaagttc   1020
```

-continued

```
aactggtacg tggacggcgt ggaggtgcat aatgccaaga caaagccgcg ggaggagcag   1080

tacaacagca cgtaccgtgt ggtcagcgtc ctcaccgtcc tgcaccagga ctggctgaat   1140

ggcaaggagt acaagtgcaa ggtctccaac aaagccctcc cagcccccat cgagaaaacc   1200

atctccaaag ccaaagggca gccccgagaa ccacaggtgt acaccctgcc cccatcccgg   1260

gatgagctga ccaagaacca ggtcagcctg acctgcctgg tcaaaggctt ctatcccagc   1320

gacatcgccg tggagtggga gagcaatggg cagccggaga acaactacaa gaccacgcct   1380

cccgtgctgg actccgacgg ctccttcttc ctctacagca agctcaccgt ggacaagagc   1440

aggtggcagc aggggaacgt cttctcatgc tccgtgatgc atgaggctct gcacaaccac   1500

tacacacaga agagcctctc cctgtctccg ggtaaatga                           1539


<210> SEQ ID NO 66
<211> LENGTH: 493
<212> TYPE: PRT
<213> ORGANISM: Artificial Sequence
<220> FEATURE:
<223> OTHER INFORMATION: Synthetic

<400> SEQUENCE: 66

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Gly Thr Gly Gly Gly Ser Gly Ser Ser Ser Leu Glu Val Thr
            100                 105                 110

Cys Glu Pro Gly Thr Thr Phe Lys Asp Lys Cys Asn Thr Cys Arg Cys
        115                 120                 125

Gly Ser Asp Gly Lys Ser Ala Phe Cys Thr Arg Lys Leu Cys Tyr Gln
    130                 135                 140

Gly Ser Gly Ala Tyr Ile Asp Ala Trp Gly His Gly Thr Glu Val Ile
145                 150                 155                 160

Val Ser Ser Ala Ser Thr Lys Gly Pro Ser Val Phe Pro Leu Ala Pro
                165                 170                 175

Ser Ser Lys Ser Thr Ser Gly Gly Thr Ala Ala Leu Gly Cys Leu Val
            180                 185                 190

Lys Asp Tyr Phe Pro Glu Pro Val Thr Val Ser Trp Asn Ser Gly Ala
        195                 200                 205

Leu Thr Ser Gly Val His Thr Phe Pro Ala Val Leu Gln Ser Ser Gly
    210                 215                 220

Leu Tyr Ser Leu Ser Ser Val Val Thr Val Pro Ser Ser Ser Leu Gly
225                 230                 235                 240

Thr Gln Thr Tyr Ile Cys Asn Val Asn His Lys Pro Ser Asn Thr Lys
                245                 250                 255

Val Asp Lys Lys Val Glu Pro Lys Ser Cys Asp Lys Thr His Thr Cys
            260                 265                 270
```

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 67
<211> LENGTH: 1527
<212> TYPE: DNA
<213> ORGANISM: Artificial Sequence
<220> FEATURE:
<223> OTHER INFORMATION: Synthetic

<400> SEQUENCE: 67
atggagttcg gcctgagctg gctgttcctg gtggccatcc ttaagggcgt gcagtgcgcc 60
gtgacgttgg acgagtccgg gggcggcctc cagacgcccg ggggagcgct cagcctcgtc 120
tgcaaggcct ccgggttcac cttcagcagt aacgccatgg gttgggtgcg acaggcgccc 180
ggcaaggggc tggagtgggt cgctggtatt gatgatgatg gtagtggcac aagatacgcg 240
ccggcggtga agggccgtgc caccatctcg agggacaacg ggcagagcac actgaggctg 300
cagctgaaca acctcagggc tgaggacacc ggcacctact actgcgccaa agccgctggt 360
ggtagtggtc tcgaggtgac atgtgaaccc ggtacgacgt ttaaggataa gtgcaacaca 420
tgtaggtgcg gtagcgacgg caaatcagcg ttctgtaccc ggaaattgtg ctaccagggt 480
agtggtgctt atatcgacgc atggggccac gggaccgaag tcatcgtctc ctccgctagc 540
accaagggcc catcggtctt ccccctggca ccctcctcca agagcacctc tgggggcaca 600
gcggccctgg gctgcctggt caaggactac ttccccgaac cggtgacggt gtcgtggaac 660
tcaggcgccc tgaccagcgg cgtgcacacc ttcccggctg tcctacagtc ctcaggactc 720
tactccctca gcagcgtggt gaccgtgccc tccagcagct tgggcaccca gacctacatc 780
tgcaacgtga atcacaagcc cagcaacacc aaggtggaca agaaagttga gcccaaatct 840

```
tgtgacaaaa ctcacacatg cccaccgtgc ccagcacctg aactcctggg gggaccgtca    900

gtcttcctct tccccccaaa acccaaggac accctcatga tctcccggac ccctgaggtc    960

acatgcgtgg tggtggacgt gagccacgaa gaccctgagg tcaagttcaa ctggtacgtg   1020

gacggcgtgg aggtgcataa tgccaagaca aagccgcggg aggagcagta caacagcacg   1080

taccgtgtgg tcagcgtcct caccgtcctg caccaggact ggctgaatgg caaggagtac   1140

aagtgcaagg tctccaacaa agccctccca gcccccatcg agaaaaccat ctccaaagcc   1200

aaagggcagc cccgagaacc acaggtgtac accctgcccc catcccggga tgagctgacc   1260

aagaaccagg tcagcctgac ctgcctggtc aaaggcttct atcccagcga catcgccgtg   1320

gagtgggaga gcaatgggca gccggagaac aactacaaga ccacgcctcc cgtgctggac   1380

tccgacggct ccttcttcct ctacagcaag ctcaccgtgg acaagagcag gtggcagcag   1440

gggaacgtct tctcatgctc cgtgatgcat gaggctctgc acaaccacta cacacagaag   1500

agcctctccc tgtctccggg taaatga                                       1527
```

<210> SEQ ID NO 68
<211> LENGTH: 489
<212> TYPE: PRT
<213> ORGANISM: Artificial Sequence
<220> FEATURE:
<223> OTHER INFORMATION: Synthetic

<400> SEQUENCE: 68

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Ala Ala Gly Gly Ser Gly Leu Glu Val Thr Cys Glu Pro Gly
            100                 105                 110

Thr Thr Phe Lys Asp Lys Cys Asn Thr Cys Arg Cys Gly Ser Asp Gly
        115                 120                 125

Lys Ser Ala Phe Cys Thr Arg Lys Leu Cys Tyr Gln Gly Ser Gly Ala
    130                 135                 140

Tyr Ile Asp Ala Trp Gly His Gly Thr Glu Val Ile Val Ser Ser Ala
145                 150                 155                 160

Ser Thr Lys Gly Pro Ser Val Phe Pro Leu Ala Pro Ser Ser Lys Ser
                165                 170                 175

Thr Ser Gly Gly Thr Ala Ala Leu Gly Cys Leu Val Lys Asp Tyr Phe
            180                 185                 190

Pro Glu Pro Val Thr Val Ser Trp Asn Ser Gly Ala Leu Thr Ser Gly
        195                 200                 205

Val His Thr Phe Pro Ala Val Leu Gln Ser Ser Gly Leu Tyr Ser Leu
    210                 215                 220

Ser Ser Val Val Thr Val Pro Ser Ser Ser Leu Gly Thr Gln Thr Tyr
225                 230                 235                 240
```

```
Ile Cys Asn Val Asn His Lys Pro Ser Asn Thr Lys Val Asp Lys Lys
                245                 250                 255

Val Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
    370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485
```

<210> SEQ ID NO 69
<211> LENGTH: 1539
<212> TYPE: DNA
<213> ORGANISM: Artificial Sequence
<220> FEATURE:
<223> OTHER INFORMATION: Synthetic

<400> SEQUENCE: 69

```
atggagttcg gcctgagctg gctgttcctg gtggccatcc ttaagggcgt gcagtgcgcc      60

gtgacgttgg acgagtccgg gggcggcctc cagacgcccg gggggagcgct cagcctcgtc    120

tgcaaggcct ccgggttcac cttcagcagt aacgccatgg gttgggtgcg acaggcgccc    180

ggcaaggggc tggagtgggt cgctggtatt gatgatgatg gtagtggcac aagatacgcg    240

ccggcggtga agggccgtgc caccatctcg agggacaacg ggcagagcac actgaggctg    300

cagctgaaca acctcagggc tgaggacacc ggcacctact actgcgccaa agccgctggt    360

ggtagtggtg gtagtggtgc tctcgaggtg acatgtgaac ccggtacgac gtttaaggat    420

aagtgcaaca catgtaggtg cggtagcgac ggcaaatcag cgttctgtac ccggaaattg    480

tgctaccagg gtagtggtgc ttatatcgac gcatggggcc acgggaccga agtcatcgtc    540

tcctccgcta gcaccaaggg cccatcggtc ttccccctgg caccctcctc caagagcacc    600
```

```
tctgggggca cagcggccct gggctgcctg gtcaaggact acttccccga accggtgacg    660

gtgtcgtgga actcaggcgc cctgaccagc ggcgtgcaca ccttcccggc tgtcctacag    720

tcctcaggac tctactccct cagcagcgtg gtgaccgtgc cctccagcag cttgggcacc    780

cagacctaca tctgcaacgt gaatcacaag cccagcaaca ccaaggtgga caagaaagtt    840

gagcccaaat cttgtgacaa aactcacaca tgcccaccgt gcccagcacc tgaactcctg    900

gggggaccgt cagtcttcct cttcccccca aaacccaagg acaccctcat gatctcccgg    960

acccctgagg tcacatgcgt ggtggtggac gtgagccacg aagaccctga ggtcaagttc   1020

aactggtacg tggacggcgt ggaggtgcat aatgccaaga caaagccgcg ggaggagcag   1080

tacaacagca cgtaccgtgt ggtcagcgtc ctcaccgtcc tgcaccagga ctggctgaat   1140

ggcaaggagt acaagtgcaa ggtctccaac aaagccctcc cagcccccat cgagaaaacc   1200

atctccaaag ccaaagggca gccccgagaa ccacaggtgt acaccctgcc cccatcccgg   1260

gatgagctga ccaagaacca ggtcagcctg acctgcctgg tcaaaggctt ctatcccagc   1320

gacatcgccg tggagtggga gagcaatggg cagccggaga acaactacaa gaccacgcct   1380

cccgtgctgg actccgacgg ctccttcttc ctctacagca agctcaccgt ggacaagagc   1440

aggtggcagc aggggaacgt cttctcatgc tccgtgatgc atgaggctct gcacaaccac   1500

tacacacaga agagcctctc cctgtctccg ggtaaatga                          1539
```

<210> SEQ ID NO 70
<211> LENGTH: 493
<212> TYPE: PRT
<213> ORGANISM: Artificial Sequence
<220> FEATURE:
<223> OTHER INFORMATION: Synthetic

<400> SEQUENCE: 70

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Ala Ala Gly Gly Ser Gly Gly Ser Gly Ala Leu Glu Val Thr
            100                 105                 110

Cys Glu Pro Gly Thr Thr Phe Lys Asp Lys Cys Asn Thr Cys Arg Cys
        115                 120                 125

Gly Ser Asp Gly Lys Ser Ala Phe Cys Thr Arg Lys Leu Cys Tyr Gln
    130                 135                 140

Gly Ser Gly Ala Tyr Ile Asp Ala Trp Gly His Gly Thr Glu Val Ile
145                 150                 155                 160

Val Ser Ser Ala Ser Thr Lys Gly Pro Ser Val Phe Pro Leu Ala Pro
                165                 170                 175

Ser Ser Lys Ser Thr Ser Gly Gly Thr Ala Ala Leu Gly Cys Leu Val
            180                 185                 190

Lys Asp Tyr Phe Pro Glu Pro Val Thr Val Ser Trp Asn Ser Gly Ala
```

```
        195                 200                 205

Leu Thr Ser Gly Val His Thr Phe Pro Ala Val Leu Gln Ser Ser Gly
    210                 215                 220

Leu Tyr Ser Leu Ser Ser Val Val Thr Val Pro Ser Ser Ser Leu Gly
225                 230                 235                 240

Thr Gln Thr Tyr Ile Cys Asn Val Asn His Lys Pro Ser Asn Thr Lys
                245                 250                 255

Val Asp Lys Lys Val Glu Pro Lys Ser Cys Asp Lys Thr His Thr Cys
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490


<210> SEQ ID NO 71
<211> LENGTH: 1527
<212> TYPE: DNA
<213> ORGANISM: Artificial Sequence
<220> FEATURE:
<223> OTHER INFORMATION: Synthetic

<400> SEQUENCE: 71

atggagttcg gcctgagctg gctgttcctg gtggccatcc ttaagggcgt gcagtgcgcc     60

gtgacgttgg acgagtccgg gggcggcctc cagacgcccg ggggagcgct cagcctcgtc    120

tgcaaggcct ccgggttcac cttcagcagt aacgccatgg gttgggtgcg acaggcgccc    180

ggcaaggggc tggagtgggt cgctggtatt gatgatgatg gtagtggcac aagatacgcg    240

ccggcggtga agggccgtgc caccatctcg agggacaacg ggcagagcac actgaggctg    300

cagctgaaca acctcagggc tgaggacacc ggcacctact actgcgccaa actcgaggtg    360

acatgtgaac ccggtacgac gtttaaggat aagtgcaaca catgtaggtg cggtagcgac    420
```

```
ggcaaatcag cgttctgtac ccggaaattg tgctaccagg ccgctggtgg tagtggtggt    480

agtggtgctt atatcgacgc atggggccac gggaccgaag tcatcgtctc ctccgctagc    540

accaagggcc catcggtctt ccccctggca ccctcctcca agagcacctc tgggggcaca    600

gcggccctgg gctgcctggt caaggactac ttccccgaac cggtgacggt gtcgtggaac    660

tcaggcgccc tgaccagcgg cgtgcacacc ttcccggctg tcctacagtc ctcaggactc    720

tactccctca gcagcgtggt gaccgtgccc tccagcagct tgggcaccca gacctacatc    780

tgcaacgtga atcacaagcc cagcaacacc aaggtggaca agaaagttga gcccaaatct    840

tgtgacaaaa ctcacacatg cccaccgtgc ccagcacctg aactcctggg gggaccgtca    900

gtcttcctct tccccccaaa acccaaggac accctcatga tctcccggac ccctgaggtc    960

acatgcgtgg tggtggacgt gagccacgaa gaccctgagg tcaagttcaa ctggtacgtg   1020

gacggcgtgg aggtgcataa tgccaagaca aagccgcggg aggagcagta caacagcacg   1080

taccgtgtgg tcagcgtcct caccgtcctg caccaggact ggctgaatgg caaggagtac   1140

aagtgcaagg tctccaacaa agccctccca gcccccatcg agaaaaccat ctccaaagcc   1200

aaagggcagc cccgagaacc acaggtgtac accctgcccc catcccggga tgagctgacc   1260

aagaaccagg tcagcctgac ctgcctggtc aaaggcttct atcccagcga catcgccgtg   1320

gagtgggaga gcaatgggca gccggagaac aactacaaga ccacgcctcc cgtgctggac   1380

tccgacggct ccttcttcct ctacagcaag ctcaccgtgg acaagagcag gtggcagcag   1440

gggaacgtct tctcatgctc cgtgatgcat gaggctctgc acaaccacta cacacagaag   1500

agcctctccc tgtctccggg taaatga                                       1527


<210> SEQ ID NO 72
<211> LENGTH: 489
<212> TYPE: PRT
<213> ORGANISM: Artificial Sequence
<220> FEATURE:
<223> OTHER INFORMATION: Synthetic

<400> SEQUENCE: 72

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Leu Glu Val Thr Cys Glu Pro Gly Thr Thr Phe Lys Asp Lys
            100                 105                 110

Cys Asn Thr Cys Arg Cys Gly Ser Asp Gly Lys Ser Ala Phe Cys Thr
        115                 120                 125

Arg Lys Leu Cys Tyr Gln Ala Ala Gly Gly Ser Gly Gly Ser Gly Ala
    130                 135                 140

Tyr Ile Asp Ala Trp Gly His Gly Thr Glu Val Ile Val Ser Ser Ala
145                 150                 155                 160
```

-continued

```
Ser Thr Lys Gly Pro Ser Val Phe Pro Leu Ala Pro Ser Ser Lys Ser
                165                 170                 175

Thr Ser Gly Gly Thr Ala Ala Leu Gly Cys Leu Val Lys Asp Tyr Phe
            180                 185                 190

Pro Glu Pro Val Thr Val Ser Trp Asn Ser Gly Ala Leu Thr Ser Gly
        195                 200                 205

Val His Thr Phe Pro Ala Val Leu Gln Ser Ser Gly Leu Tyr Ser Leu
    210                 215                 220

Ser Ser Val Val Thr Val Pro Ser Ser Ser Leu Gly Thr Gln Thr Tyr
225                 230                 235                 240

Ile Cys Asn Val Asn His Lys Pro Ser Asn Thr Lys Val Asp Lys Lys
                245                 250                 255

Val Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
    370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485
```

<210> SEQ ID NO 73
<211> LENGTH: 1557
<212> TYPE: DNA
<213> ORGANISM: Artificial Sequence
<220> FEATURE:
<223> OTHER INFORMATION: Synthetic

<400> SEQUENCE: 73

```
atggagttcg gcctgagctg gctgttcctg gtggccatcc ttaagggcgt gcagtgcgcc      60

gtgacgttgg acgagtccgg gggcggcctc cagacgcccg ggggagcgct cagcctcgtc     120

tgcaaggcct ccgggttcac cttcagcagt aacgccatgg gttgggtgcg acaggcgccc     180
```

```
ggcaaggggc tggagtgggt cgctggtatt gatgatgatg gtagtggcac aagatacgcg    240

ccggcggtga agggccgtgc caccatctcg agggacaacg ggcagagcac actgaggctg    300

cagctgaaca acctcagggc tgaggacacc ggcacctact actgcgccaa aggcaccggt    360

ggagggtcgg gatccagctc actcgaggtg acatgtgaac ccggtacgac gtttaaggat    420

aagtgcaaca catgtaggtg cggtagcgac ggcaaatcag cgttctgtac ccggaaattg    480

tgctaccagg ccgctggtgg tagtggtggt agtggtgctt atatcgacgc atggggccac    540

gggaccgaag tcatcgtctc ctccgctagc accaagggcc catcggtctt cccccctggca    600

ccctcctcca agagcacctc tgggggcaca gcggccctgg gctgcctggt caaggactac    660

ttccccgaac cggtgacggt gtcgtggaac tcaggcgccc tgaccagcgg cgtgcacacc    720

ttcccggctg tcctacagtc ctcaggactc tactccctca gcagcgtggt gaccgtgccc    780

tccagcagct tgggcaccca gacctacatc tgcaacgtga atcacaagcc cagcaacacc    840

aaggtggaca agaaagttga gcccaaatct tgtgacaaaa ctcacacatg cccaccgtgc    900

ccagcacctg aactcctggg gggaccgtca gtcttcctct tccccccaaa acccaaggac    960

accctcatga tctcccggac ccctgaggtc acatgcgtgg tggtggacgt gagccacgaa   1020

gaccctgagg tcaagttcaa ctggtacgtg gacggcgtgg aggtgcataa tgccaagaca   1080

aagccgcggg aggagcagta caacagcacg taccgtgtgg tcagcgtcct caccgtcctg   1140

caccaggact ggctgaatgg caaggagtac aagtgcaagg tctccaacaa agccctccca   1200

gcccccatcg agaaaaccat ctccaaagcc aaagggcagc cccgagaacc acaggtgtac   1260

accctgcccc catcccggga tgagctgacc aagaaccagg tcagcctgac ctgcctggtc   1320

aaaggcttct atcccagcga catcgccgtg gagtgggaga gcaatgggca gccggagaac   1380

aactacaaga ccacgcctcc cgtgctggac tccgacggct ccttcttcct ctacagcaag   1440

ctcaccgtgg acaagagcag gtggcagcag gggaacgtct tctcatgctc cgtgatgcat   1500

gaggctctgc acaaccacta cacacagaag agcctctccc tgtctccggg taaatga      1557
```

<210> SEQ ID NO 74
<211> LENGTH: 499
<212> TYPE: PRT
<213> ORGANISM: Artificial Sequence
<220> FEATURE:
<223> OTHER INFORMATION: Synthetic

<400> SEQUENCE: 74

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Gly Thr Gly Gly Gly Ser Gly Ser Ser Ser Leu Glu Val Thr
            100                 105                 110

Cys Glu Pro Gly Thr Thr Phe Lys Asp Lys Cys Asn Thr Cys Arg Cys
        115                 120                 125
```

```
Gly Ser Asp Gly Lys Ser Ala Phe Cys Thr Arg Lys Leu Cys Tyr Gln
    130                 135                 140

Ala Ala Gly Gly Ser Gly Gly Ser Gly Ala Tyr Ile Asp Ala Trp Gly
145                 150                 155                 160

His Gly Thr Glu Val Ile Val Ser Ser Ala Ser Thr Lys Gly Pro Ser
                165                 170                 175

Val Phe Pro Leu Ala Pro Ser Ser Lys Ser Thr Ser Gly Gly Thr Ala
            180                 185                 190

Ala Leu Gly Cys Leu Val Lys Asp Tyr Phe Pro Glu Pro Val Thr Val
        195                 200                 205

Ser Trp Asn Ser Gly Ala Leu Thr Ser Gly Val His Thr Phe Pro Ala
    210                 215                 220

Val Leu Gln Ser Ser Gly Leu Tyr Ser Leu Ser Ser Val Val Thr Val
225                 230                 235                 240

Pro Ser Ser Ser Leu Gly Thr Gln Thr Tyr Ile Cys Asn Val Asn His
                245                 250                 255

Lys Pro Ser Asn Thr Lys Val Asp Lys Lys Val Glu Pro Lys Ser Cys
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys
```

<210> SEQ ID NO 75
<211> LENGTH: 1545
<212> TYPE: DNA
<213> ORGANISM: Artificial Sequence
<220> FEATURE:
<223> OTHER INFORMATION: Synthetic

<400> SEQUENCE: 75
atggagttcg gcctgagctg gctgttcctg gtggccatcc ttaagggcgt gcagtgcgcc 60
gtgacgttgg acgagtccgg gggcggcctc cagacgcccg ggggagcgct cagcctcgtc 120
tgcaaggcct ccgggttcac cttcagcagt aacgccatgg gttgggtgcg acaggcgccc 180
ggcaaggggc tggagtgggt cgctggtatt gatgatgatg gtagtggcac aagatacgcg 240
ccggcggtga agggccgtgc caccatctcg agggacaacg ggcagagcac actgaggctg 300
cagctgaaca acctcagggc tgaggacacc ggcacctact actgcgccaa agccgctggt 360
ggtagtggtc tcgaggtgac atgtgaaccc ggtacgacgt ttaaggataa gtgcaacaca 420
tgtaggtgcg gtagcgacgg caaatcagcg ttctgtaccc ggaaattgtg ctaccaggcc 480
gctggtggta gtggtggtag tggtgcttat atcgacgcat ggggccacgg gaccgaagtc 540
atcgtctcct ccgctagcac caagggccca tcggtcttcc ccctggcacc ctcctccaag 600
agcacctctg ggggcacagc ggccctgggc tgcctggtca aggactactt ccccgaaccg 660
gtgacggtgt cgtggaactc aggcgccctg accagcggcg tgcacacctt cccggctgtc 720
ctacagtcct caggactcta ctccctcagc agcgtggtga ccgtgccctc cagcagcttg 780
ggcacccaga cctacatctg caacgtgaat cacaagccca gcaacaccaa ggtggacaag 840
aaagttgagc ccaaatcttg tgacaaaact cacacatgcc caccgtgccc agcacctgaa 900
ctcctggggg gaccgtcagt cttcctcttc cccccaaaac ccaaggacac cctcatgatc 960
tcccggaccc ctgaggtcac atgcgtggtg gtggacgtga gccacgaaga ccctgaggtc 1020
aagttcaact ggtacgtgga cggcgtggag gtgcataatg ccaagacaaa gccgcgggag 1080
gagcagtaca acagcacgta ccgtgtggtc agcgtcctca ccgtcctgca ccaggactgg 1140
ctgaatggca aggagtacaa gtgcaaggtc tccaacaaag ccctcccagc ccccatcgag 1200
aaaaccatct ccaaagccaa agggcagccc cgagaaccac aggtgtacac cctgccccca 1260
tcccgggatg agctgaccaa gaaccaggtc agcctgacct gcctggtcaa aggcttctat 1320
cccagcgaca tcgccgtgga gtgggagagc aatgggcagc cggagaacaa ctacaagacc 1380
acgcctcccg tgctggactc cgacggctcc ttcttcctct acagcaagct caccgtggac 1440
aagagcaggt ggcagcaggg gaacgtcttc tcatgctccg tgatgcatga ggctctgcac 1500
aaccactaca cacagaagag cctctccctg tctccgggta aatga 1545

<210> SEQ ID NO 76
<211> LENGTH: 495
<212> TYPE: PRT
<213> ORGANISM: Artificial Sequence
<220> FEATURE:
<223> OTHER INFORMATION: Synthetic

<400> SEQUENCE: 76

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

-continued

```
Leu Gln Leu Asn Asn Leu Arg Ala Glu Asp Thr Gly Thr Tyr Tyr Cys
                85                  90                  95

Ala Lys Ala Ala Gly Gly Ser Gly Leu Glu Val Thr Cys Glu Pro Gly
            100                 105                 110

Thr Thr Phe Lys Asp Lys Cys Asn Thr Cys Arg Cys Gly Ser Asp Gly
        115                 120                 125

Lys Ser Ala Phe Cys Thr Arg Lys Leu Cys Tyr Gln Ala Ala Gly Gly
    130                 135                 140

Ser Gly Gly Ser Gly Ala Tyr Ile Asp Ala Trp Gly His Gly Thr Glu
145                 150                 155                 160

Val Ile Val Ser Ser Ala Ser Thr Lys Gly Pro Ser Val Phe Pro Leu
                165                 170                 175

Ala Pro Ser Ser Lys Ser Thr Ser Gly Gly Thr Ala Ala Leu Gly Cys
            180                 185                 190

Leu Val Lys Asp Tyr Phe Pro Glu Pro Val Thr Val Ser Trp Asn Ser
        195                 200                 205

Gly Ala Leu Thr Ser Gly Val His Thr Phe Pro Ala Val Leu Gln Ser
    210                 215                 220

Ser Gly Leu Tyr Ser Leu Ser Ser Val Val Thr Val Pro Ser Ser Ser
225                 230                 235                 240

Leu Gly Thr Gln Thr Tyr Ile Cys Asn Val Asn His Lys Pro Ser Asn
                245                 250                 255

Thr Lys Val Asp Lys Lys Val Glu Pro Lys Ser Cys Asp Lys Thr His
            260                 265                 270

Thr Cys Pro Pro Cys Pro Ala Pro Glu Leu Leu Gly Gly Pro Ser Val
        275                 280                 285

Phe Leu Phe Pro Pro Lys Pro Lys Asp Thr Leu Met Ile Ser Arg Thr
    290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Ala Leu Pro Ala Pro Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Lys Leu Thr Val Asp Lys Ser Arg
    450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys
                485                 490                 495
```

<210> SEQ ID NO 77
<211> LENGTH: 1557
<212> TYPE: DNA
<213> ORGANISM: Artificial Sequence
<220> FEATURE:
<223> OTHER INFORMATION: Synthetic

<400> SEQUENCE: 77

```
atggagttcg gcctgagctg gctgttcctg gtggccatcc ttaagggcgt gcagtgcgcc     60

gtgacgttgg acgagtccgg gggcggcctc cagacgcccg ggggagcgct cagcctcgtc    120

tgcaaggcct ccgggttcac cttcagcagt aacgccatgg gttgggtgcg acaggcgccc    180

ggcaaggggc tggagtgggt cgctggtatt gatgatgatg gtagtggcac aagatacgcg    240

ccggcggtga agggccgtgc caccatctcg agggacaacg ggcagagcac actgaggctg    300

cagctgaaca acctcagggc tgaggacacc ggcacctact actgcgccaa agccgctggt    360

ggtagtggtg gtagtggtgc tctcgaggtg acatgtgaac ccggtacgac gtttaaggat    420

aagtgcaaca catgtaggtg cggtagcgac ggcaaatcag cgttctgtac ccggaaattg    480

tgctaccagg ccgctggtgg tagtggtggt agtggtgctt atatcgacgc atggggccac    540

gggaccgaag tcatcgtctc ctccgctagc accaagggcc catcggtctt cccccctggca    600

ccctcctcca agagcacctc tgggggcaca gcggccctgg gctgcctggt caaggactac    660

ttccccgaac cggtgacggt gtcgtggaac tcaggcgccc tgaccagcgg cgtgcacacc    720

ttcccggctg tcctacagtc ctcaggactc tactccctca gcagcgtggt gaccgtgccc    780

tccagcagct tgggcaccca gacctacatc tgcaacgtga atcacaagcc cagcaacacc    840

aaggtggaca agaaagttga gcccaaatct tgtgacaaaa ctcacacatg cccaccgtgc    900

ccagcacctg aactcctggg gggaccgtca gtcttcctct tcccccccaaa acccaaggac    960

accctcatga tctcccggac ccctgaggtc acatgcgtgg tggtggacgt gagccacgaa   1020

gaccctgagg tcaagttcaa ctggtacgtg gacggcgtgg aggtgcataa tgccaagaca   1080

aagccgcggg aggagcagta caacagcacg taccgtgtgg tcagcgtcct caccgtcctg   1140

caccaggact ggctgaatgg caaggagtac aagtgcaagg tctccaacaa agccctccca   1200

gcccccatcg agaaaaccat ctccaaagcc aaagggcagc cccgagaacc acaggtgtac   1260

accctgcccc catcccggga tgagctgacc aagaaccagg tcagcctgac ctgcctggtc   1320

aaaggcttct atcccagcga catcgccgtg gagtgggaga gcaatgggca gccggagaac   1380

aactacaaga ccacgcctcc cgtgctggac tccgacggct ccttcttcct ctacagcaag   1440

ctcaccgtgg acaagagcag gtggcagcag gggaacgtct tctcatgctc cgtgatgcat   1500

gaggctctgc acaaccacta cacacagaag agcctctccc tgtctccggg taaatga      1557
```

<210> SEQ ID NO 78
<211> LENGTH: 499
<212> TYPE: PRT
<213> ORGANISM: Artificial Sequence
<220> FEATURE:
<223> OTHER INFORMATION: Synthetic

<400> SEQUENCE: 78

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
```

```
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Ala Ala Gly Gly Ser Gly Gly Ser Gly Ala Leu Glu Val Thr
            100                 105                 110

Cys Glu Pro Gly Thr Thr Phe Lys Asp Lys Cys Asn Thr Cys Arg Cys
        115                 120                 125

Gly Ser Asp Gly Lys Ser Ala Phe Cys Thr Arg Lys Leu Cys Tyr Gln
    130                 135                 140

Ala Ala Gly Gly Ser Gly Gly Ser Gly Ala Tyr Ile Asp Ala Trp Gly
145                 150                 155                 160

His Gly Thr Glu Val Ile Val Ser Ser Ala Ser Thr Lys Gly Pro Ser
                165                 170                 175

Val Phe Pro Leu Ala Pro Ser Ser Lys Ser Thr Ser Gly Gly Thr Ala
            180                 185                 190

Ala Leu Gly Cys Leu Val Lys Asp Tyr Phe Pro Glu Pro Val Thr Val
        195                 200                 205

Ser Trp Asn Ser Gly Ala Leu Thr Ser Gly Val His Thr Phe Pro Ala
    210                 215                 220

Val Leu Gln Ser Ser Gly Leu Tyr Ser Leu Ser Ser Val Val Thr Val
225                 230                 235                 240

Pro Ser Ser Ser Leu Gly Thr Gln Thr Tyr Ile Cys Asn Val Asn His
                245                 250                 255

Lys Pro Ser Asn Thr Lys Val Asp Lys Lys Val Glu Pro Lys Ser Cys
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460
```

Asp Lys Ser Arg Trp Gln Gln Gly Asn Val Phe Ser Cys Ser Val Met
465 470 475 480

His Glu Ala Leu His Asn His Tyr Thr Gln Lys Ser Leu Ser Leu Ser
485 490 495

Pro Gly Lys

<210> SEQ ID NO 79
<211> LENGTH: 795
<212> TYPE: DNA
<213> ORGANISM: Artificial Sequence
<220> FEATURE:
<223> OTHER INFORMATION: Synthetic

<400> SEQUENCE: 79
atggcctgga ttcctctact tctccccctc ctcactctct gcacaggatc cgaagccgcg 60
ctgactcagc ctgcctcggt gtcagcaaac ccaggagaaa ccgtcaagat cacctgctcc 120
gggggtggca gcttggaagt gacgtgtgag cccggaacga cattcaaaga caagtgcaat 180
acttgtcggt gcggttcaga tgggaaatcg gcggtctgca caaagctctg gtgtaaccag 240
tactattatg gctggtacca gcagaaggca cctggcagtg cccctgtcac tctgatctat 300
tacaacaaca agagaccctc ggacatccct tcacgattct ccggttccct atccggctcc 360
acaaacacat taaccatcac tggggtccga gccgatgacg aggctgtcta tttctgtggg 420
agtgcagaca acagtggtgc tgcatttggg gccgggacaa ccctgacagt acttggtcag 480
cccaaggctg ccccttcggt caccctgttc ccgccctcct ctgaggagct tcaagccaac 540
aaggccacac tggtgtgtct cataagtgac ttctacccgg gagccgtgac agtggcctgg 600
aaggcagata gcagccccgt caaggcggga gtggagacca ccacaccctc caaacaaagc 660
aacaacaagt acgcggccag cagctatctg agcctgacgc ctgagcagtg gaagtcccac 720
agaagctaca gctgccaggt cacgcatgaa gggagcaccg tggagaagac agtggcccct 780
acagaatgtt catag 795

<210> SEQ ID NO 80
<211> LENGTH: 245
<212> TYPE: PRT
<213> ORGANISM: Artificial Sequence
<220> FEATURE:
<223> OTHER INFORMATION: Synthetic

<400> SEQUENCE: 80

Ala Leu Thr Gln Pro Ala Ser Val Ser Ala Asn Pro Gly Glu Thr Val
1 5 10 15

Lys Ile Thr Cys Ser Gly Gly Gly Ser Leu Glu Val Thr Cys Glu Pro
20 25 30

Gly Thr Thr Phe Lys Asp Lys Cys Asn Thr Cys Arg Cys Gly Ser Asp
35 40 45

Gly Lys Ser Ala Val Cys Thr Lys Leu Trp Cys Asn Gln Tyr Tyr Tyr
50 55 60

Gly Trp Tyr Gln Gln Lys Ala Pro Gly Ser Ala Pro Val Thr Leu Ile
65 70 75 80

Tyr Tyr Asn Asn Lys Arg Pro Ser Asp Ile Pro Ser Arg Phe Ser Gly
85 90 95

Ser Leu Ser Gly Ser Thr Asn Thr Leu Thr Ile Thr Gly Val Arg Ala
100 105 110

Asp Asp Glu Ala Val Tyr Phe Cys Gly Ser Ala Asp Asn Ser Gly Ala 115 120 125

Ala Phe Gly Ala Gly Thr Thr Leu Thr Val Leu Gly Gln Pro Lys Ala
130 135 140

Ala Pro Ser Val Thr Leu Phe Pro Pro Ser Ser Glu Glu Leu Gln Ala
145 150 155 160

Asn Lys Ala Thr Leu Val Cys Leu Ile Ser Asp Phe Tyr Pro Gly Ala
165 170 175

Val Thr Val Ala Trp Lys Ala Asp Ser Ser Pro Val Lys Ala Gly Val
180 185 190

Glu Thr Thr Thr Pro Ser Lys Gln Ser Asn Asn Lys Tyr Ala Ala Ser
195 200 205

Ser Tyr Leu Ser Leu Thr Pro Glu Gln Trp Lys Ser His Arg Ser Tyr
210 215 220

Ser Cys Gln Val Thr His Glu Gly Ser Thr Val Glu Lys Thr Val Ala
225 230 235 240

Pro Thr Glu Cys Ser
245

<210> SEQ ID NO 81
<211> LENGTH: 786
<212> TYPE: DNA
<213> ORGANISM: Artificial Sequence
<220> FEATURE:
<223> OTHER INFORMATION: Synthetic

<400> SEQUENCE: 81
atggcctgga ttcctctact tctccccctc ctcactctct gcacaggatc cgaagccgcg 60
ctgactcagc ctgcctcggt gtcagcaaac ccaggagaaa ccgtcaagat cacctgctcc 120
gggggtggca gcacgtgtga gcccggaacg acattcaaag acaagtgcaa tacttgtcgg 180
tgcggttcag atgggaaatc ggcggtctgc acaaagctct ggtgtaacca gtactattat 240
ggctggtacc agcagaaggc acctggcagt gcccctgtca ctctgatcta ttacaacaac 300
aagagaccct cggacatccc ttcacgattc tccggttccc tatccggctc cacaaacaca 360
ttaaccatca ctggggtccg agccgatgac gaggctgtct atttctgtgg gagtgcagac 420
aacagtggtg ctgcatttgg ggccgggaca accctgacag tacttggtca gcccaaggct 480
gccccttcgg tcaccctgtt cccgccctcc tctgaggagc ttcaagccaa caaggccaca 540
ctggtgtgtc tcataagtga cttctacccg ggagccgtga cagtggcctg gaaggcagat 600
agcagccccg tcaaggcggg agtggagacc accacaccct ccaaacaaag caacaacaag 660
tacgcggcca gcagctatct gagcctgacg cctgagcagt ggaagtccca cagaagctac 720
agctgccagg tcacgcatga agggagcacc gtggagaaga cagtggcccc tacagaatgt 780
tcatag 786

<210> SEQ ID NO 82
<211> LENGTH: 242
<212> TYPE: PRT
<213> ORGANISM: Artificial Sequence
<220> FEATURE:
<223> OTHER INFORMATION: Synthetic

<400> SEQUENCE: 82

Ala Leu Thr Gln Pro Ala Ser Val Ser Ala Asn Pro Gly Glu Thr Val
1 5 10 15

Lys Ile Thr Cys Ser Gly Gly Gly Ser Thr Cys Glu Pro Gly Thr Thr
20 25 30

```
Phe Lys Asp Lys Cys Asn Thr Cys Arg Cys Gly Ser Asp Gly Lys Ser
        35                  40                  45

Ala Val Cys Thr Lys Leu Trp Cys Asn Gln Tyr Tyr Tyr Gly Trp Tyr
    50                  55                  60

Gln Gln Lys Ala Pro Gly Ser Ala Pro Val Thr Leu Ile Tyr Tyr Asn
65                  70                  75                  80

Asn Lys Arg Pro Ser Asp Ile Pro Ser Arg Phe Ser Gly Ser Leu Ser
                85                  90                  95

Gly Ser Thr Asn Thr Leu Thr Ile Thr Gly Val Arg Ala Asp Asp Glu
            100                 105                 110

Ala Val Tyr Phe Cys Gly Ser Ala Asp Asn Ser Gly Ala Ala Phe Gly
        115                 120                 125

Ala Gly Thr Thr Leu Thr Val Leu Gly Gln Pro Lys Ala Ala Pro Ser
    130                 135                 140

Val Thr Leu Phe Pro Pro Ser Ser Glu Glu Leu Gln Ala Asn Lys Ala
145                 150                 155                 160

Thr Leu Val Cys Leu Ile Ser Asp Phe Tyr Pro Gly Ala Val Thr Val
                165                 170                 175

Ala Trp Lys Ala Asp Ser Ser Pro Val Lys Ala Gly Val Glu Thr Thr
            180                 185                 190

Thr Pro Ser Lys Gln Ser Asn Asn Lys Tyr Ala Ala Ser Ser Tyr Leu
        195                 200                 205

Ser Leu Thr Pro Glu Gln Trp Lys Ser His Arg Ser Tyr Ser Cys Gln
    210                 215                 220

Val Thr His Glu Gly Ser Thr Val Glu Lys Thr Val Ala Pro Thr Glu
225                 230                 235                 240

Cys Ser
```

<210> SEQ ID NO 83
<211> LENGTH: 747
<212> TYPE: DNA
<213> ORGANISM: Artificial Sequence
<220> FEATURE:
<223> OTHER INFORMATION: Synthetic

<400> SEQUENCE: 83

```
atggcctgga ttcctctact tctcccccctc ctcactctct gcacaggatc cgaagccgcg      60

ctgactcagc ctgcctcggt gtcagcaaac ccaggagaaa ccgtcaagat cacctgctcc     120

gggggtggca gcacttgtcg gtgcggttca gatgggaaat cggcggtctg cacaaagctc     180

tggtgtaacc agtactatta tggctggtac cagcagaagg cacctggcag tgcccctgtc     240

actctgatct attacaacaa caagagaccc tcggacatcc cttcacgatt ctccggttcc     300

ctatccggct ccacaaacac attaaccatc actggggtcc gagccgatga cgaggctgtc     360

tatttctgtg ggagtgcaga caacagtggt gctgcatttg ggccgggac aaccctgaca      420

gtacttggtc agcccaaggc tgccccttcg gtcaccctgt tcccgccctc ctctgaggag     480

cttcaagcca acaaggccac actggtgtgt ctcataagtg acttctaccc gggagccgtg     540

acagtggcct ggaaggcaga tagcagcccc gtcaaggcgg gagtggagac caccacaccc     600

tccaaacaaa gcaacaacaa gtacgcggcc agcagctatc tgagcctgac gcctgagcag     660

tggaagtccc acagaagcta cagctgccag gtcacgcatg aagggagcac cgtggagaag     720

acagtggccc ctacagaatg ttcatag                                         747
```

<210> SEQ ID NO 84
<211> LENGTH: 229
<212> TYPE: PRT
<213> ORGANISM: Artificial Sequence
<220> FEATURE:
<223> OTHER INFORMATION: Synthetic

<400> SEQUENCE: 84

```
Ala Leu Thr Gln Pro Ala Ser Val Ser Ala Asn Pro Gly Glu Thr Val
1               5                   10                  15

Lys Ile Thr Cys Ser Gly Gly Gly Ser Thr Cys Arg Cys Gly Ser Asp
            20                  25                  30

Gly Lys Ser Ala Val Cys Thr Lys Leu Trp Cys Asn Gln Tyr Tyr Tyr
        35                  40                  45

Gly Trp Tyr Gln Gln Lys Ala Pro Gly Ser Ala Pro Val Thr Leu Ile
    50                  55                  60

Tyr Tyr Asn Asn Lys Arg Pro Ser Asp Ile Pro Ser Arg Phe Ser Gly
65                  70                  75                  80

Ser Leu Ser Gly Ser Thr Asn Thr Leu Thr Ile Thr Gly Val Arg Ala
                85                  90                  95

Asp Asp Glu Ala Val Tyr Phe Cys Gly Ser Ala Asp Asn Ser Gly Ala
            100                 105                 110

Ala Phe Gly Ala Gly Thr Thr Leu Thr Val Leu Gly Gln Pro Lys Ala
        115                 120                 125

Ala Pro Ser Val Thr Leu Phe Pro Pro Ser Ser Glu Glu Leu Gln Ala
    130                 135                 140

Asn Lys Ala Thr Leu Val Cys Leu Ile Ser Asp Phe Tyr Pro Gly Ala
145                 150                 155                 160

Val Thr Val Ala Trp Lys Ala Asp Ser Ser Pro Val Lys Ala Gly Val
                165                 170                 175

Glu Thr Thr Thr Pro Ser Lys Gln Ser Asn Asn Lys Tyr Ala Ala Ser
            180                 185                 190

Ser Tyr Leu Ser Leu Thr Pro Glu Gln Trp Lys Ser His Arg Ser Tyr
        195                 200                 205

Ser Cys Gln Val Thr His Glu Gly Ser Thr Val Glu Lys Thr Val Ala
    210                 215                 220

Pro Thr Glu Cys Ser
225
```

<210> SEQ ID NO 85
<211> LENGTH: 795
<212> TYPE: DNA
<213> ORGANISM: Artificial Sequence
<220> FEATURE:
<223> OTHER INFORMATION: Synthetic

<400> SEQUENCE: 85

```
atggcctgga ttcctctact tctccccctc ctcactctct gcacaggatc cgaagccgcg      60

ctgactcagc ctgcctcggt gtcagcaaac ccaggagaaa ccgtcaagat cacctgctcc     120

gggggtggca gcctcgaggt gacatgtgaa cccggtacga cgtttaagga taagtgcaac     180

acatgtaggt gcggtagcga cggcaaatca gcgttctgta cccggaaatt gtgctaccag     240

tactattatg gctggtacca gcagaaggca cctggcagtg cccctgtcac tctgatctat     300

tacaacaaca agagaccctc ggacatccct tcacgattct ccggttccct atccggctcc     360

acaaacacat taaccatcac tggggtccga gccgatgacg aggctgtcta tttctgtggg     420

agtgcagaca acagtggtgc tgcatttggg gccgggacaa ccctgacagt acttggtcag     480
```

cccaaggctg ccccttcggt caccctgttc ccgccctcct ctgaggagct tcaagccaac 540
aaggccacac tggtgtgtct cataagtgac ttctacccgg gagccgtgac agtggcctgg 600
aaggcagata gcagccccgt caaggcggga gtggagacca ccacaccctc caaacaaagc 660
aacaacaagt acgcggccag cagctatctg agcctgacgc ctgagcagtg gaagtcccac 720
agaagctaca gctgccaggt cacgcatgaa gggagcaccg tggagaagac agtggcccct 780
acagaatgtt catag 795

<210> SEQ ID NO 86
<211> LENGTH: 245
<212> TYPE: PRT
<213> ORGANISM: Artificial Sequence
<220> FEATURE:
<223> OTHER INFORMATION: Synthetic

<400> SEQUENCE: 86

Ala Leu Thr Gln Pro Ala Ser Val Ser Ala Asn Pro Gly Glu Thr Val
1 5 10 15

Lys Ile Thr Cys Ser Gly Gly Gly Ser Leu Glu Val Thr Cys Glu Pro
20 25 30

Gly Thr Thr Phe Lys Asp Lys Cys Asn Thr Cys Arg Cys Gly Ser Asp
35 40 45

Gly Lys Ser Ala Phe Cys Thr Arg Lys Leu Cys Tyr Gln Tyr Tyr Tyr
50 55 60

Gly Trp Tyr Gln Gln Lys Ala Pro Gly Ser Ala Pro Val Thr Leu Ile
65 70 75 80

Tyr Tyr Asn Asn Lys Arg Pro Ser Asp Ile Pro Ser Arg Phe Ser Gly
85 90 95

Ser Leu Ser Gly Ser Thr Asn Thr Leu Thr Ile Thr Gly Val Arg Ala
100 105 110

Asp Asp Glu Ala Val Tyr Phe Cys Gly Ser Ala Asp Asn Ser Gly Ala
115 120 125

Ala Phe Gly Ala Gly Thr Thr Leu Thr Val Leu Gly Gln Pro Lys Ala
130 135 140

Ala Pro Ser Val Thr Leu Phe Pro Pro Ser Ser Glu Glu Leu Gln Ala
145 150 155 160

Asn Lys Ala Thr Leu Val Cys Leu Ile Ser Asp Phe Tyr Pro Gly Ala
165 170 175

Val Thr Val Ala Trp Lys Ala Asp Ser Ser Pro Val Lys Ala Gly Val
180 185 190

Glu Thr Thr Thr Pro Ser Lys Gln Ser Asn Asn Lys Tyr Ala Ala Ser
195 200 205

Ser Tyr Leu Ser Leu Thr Pro Glu Gln Trp Lys Ser His Arg Ser Tyr
210 215 220

Ser Cys Gln Val Thr His Glu Gly Ser Thr Val Glu Lys Thr Val Ala
225 230 235 240

Pro Thr Glu Cys Ser
245

<210> SEQ ID NO 87
<211> LENGTH: 786
<212> TYPE: DNA
<213> ORGANISM: Artificial Sequence
<220> FEATURE:
<223> OTHER INFORMATION: Synthetic

<400> SEQUENCE: 87

```
atggcctgga ttcctctact tctcccccctc ctcactctct gcacaggatc cgaagccgcg     60
ctgactcagc ctgcctcggt gtcagcaaac ccaggagaaa ccgtcaagat cacctgctcc    120
gggggtggca gcacatgtga acccggtacg acgtttaagg ataagtgcaa cacatgtagg    180
tgcggtagcg acggcaaatc agcgttctgt acccggaaat tgtgctacca gtactattat    240
ggctggtacc agcagaaggc acctggcagt gcccctgtca ctctgatcta ttacaacaac    300
aagagaccct cggacatccc ttcacgattc tccggttccc tatccggctc cacaaacaca    360
ttaaccatca ctggggtccg agccgatgac gaggctgtct atttctgtgg gagtgcagac    420
aacagtggtg ctgcatttgg ggccgggaca accctgacag tacttggtca gcccaaggct    480
gccccttcgg tcaccctgtt cccgccctcc tctgaggagc ttcaagccaa caaggccaca    540
ctggtgtgtc tcataagtga cttctacccg ggagccgtga cagtggcctg gaaggcagat    600
agcagccccg tcaaggcggg agtggagacc accacaccct ccaaacaaag caacaacaag    660
tacgcggcca gcagctatct gagcctgacg cctgagcagt ggaagtccca cagaagctac    720
agctgccagg tcacgcatga agggagcacc gtggagaaga cagtggcccc tacagaatgt    780
tcatag                                                               786
```

<210> SEQ ID NO 88
<211> LENGTH: 242
<212> TYPE: PRT
<213> ORGANISM: Artificial Sequence
<220> FEATURE:
<223> OTHER INFORMATION: Synthetic

<400> SEQUENCE: 88

```
Ala Leu Thr Gln Pro Ala Ser Val Ser Ala Asn Pro Gly Glu Thr Val
1               5                   10                  15

Lys Ile Thr Cys Ser Gly Gly Gly Ser Thr Cys Glu Pro Gly Thr Thr
            20                  25                  30

Phe Lys Asp Lys Cys Asn Thr Cys Arg Cys Gly Ser Asp Gly Lys Ser
        35                  40                  45

Ala Phe Cys Thr Arg Lys Leu Cys Tyr Gln Tyr Tyr Tyr Gly Trp Tyr
    50                  55                  60

Gln Gln Lys Ala Pro Gly Ser Ala Pro Val Thr Leu Ile Tyr Tyr Asn
65                  70                  75                  80

Asn Lys Arg Pro Ser Asp Ile Pro Ser Arg Phe Ser Gly Ser Leu Ser
                85                  90                  95

Gly Ser Thr Asn Thr Leu Thr Ile Thr Gly Val Arg Ala Asp Asp Glu
            100                 105                 110

Ala Val Tyr Phe Cys Gly Ser Ala Asp Asn Ser Gly Ala Ala Phe Gly
        115                 120                 125

Ala Gly Thr Thr Leu Thr Val Leu Gly Gln Pro Lys Ala Ala Pro Ser
    130                 135                 140

Val Thr Leu Phe Pro Pro Ser Ser Glu Glu Leu Gln Ala Asn Lys Ala
145                 150                 155                 160

Thr Leu Val Cys Leu Ile Ser Asp Phe Tyr Pro Gly Ala Val Thr Val
                165                 170                 175

Ala Trp Lys Ala Asp Ser Ser Pro Val Lys Ala Gly Val Glu Thr Thr
            180                 185                 190

Thr Pro Ser Lys Gln Ser Asn Asn Lys Tyr Ala Ala Ser Ser Tyr Leu
        195                 200                 205
```

```
Ser Leu Thr Pro Glu Gln Trp Lys Ser His Arg Ser Tyr Ser Cys Gln
    210                 215                 220

Val Thr His Glu Gly Ser Thr Val Glu Lys Thr Val Ala Pro Thr Glu
225                 230                 235                 240

Cys Ser
```

<210> SEQ ID NO 89
<211> LENGTH: 747
<212> TYPE: DNA
<213> ORGANISM: Artificial Sequence
<220> FEATURE:
<223> OTHER INFORMATION: Synthetic

<400> SEQUENCE: 89

```
atggcctgga ttcctctact tctcccccte ctcactctct gcacaggatc cgaagccgcg        60
ctgactcagc ctgcctcggt gtcagcaaac ccaggagaaa ccgtcaagat cacctgctcc       120
gggggtggca gcacatgtag gtgcggtagc gacggcaaat cagcgttctg tacccggaaa       180
ttgtgctacc agtactatta tggctggtac cagcagaagg cacctggcag tgcccctgtc       240
actctgatct attacaacaa caagagaccc tcggacatcc cttcacgatt ctccggttcc       300
ctatccggct ccacaaacac attaaccatc actggggtcc gagccgatga cgaggctgtc       360
tatttctgtg ggagtgcaga caacagtggt gctgcatttg gggccgggac aaccctgaca       420
gtacttggtc agcccaaggc tgccccttcg gtcaccctgt tcccgccctc ctctgaggag       480
cttcaagcca acaaggccac actggtgtgt ctcataagtg acttctaccc gggagccgtg       540
acagtggcct ggaaggcaga tagcagcccc gtcaaggcgg gagtggagac caccacaccc       600
tccaaacaaa gcaacaacaa gtacgcggcc agcagctatc tgagcctgac gcctgagcag       660
tggaagtccc acagaagcta cagctgccag gtcacgcatg aagggagcac cgtggagaag       720
acagtggccc ctacagaatg ttcatag                                           747
```

<210> SEQ ID NO 90
<211> LENGTH: 229
<212> TYPE: PRT
<213> ORGANISM: Artificial Sequence
<220> FEATURE:
<223> OTHER INFORMATION: Synthetic

<400> SEQUENCE: 90

```
Ala Leu Thr Gln Pro Ala Ser Val Ser Ala Asn Pro Gly Glu Thr Val
1               5                   10                  15

Lys Ile Thr Cys Ser Gly Gly Gly Ser Thr Cys Arg Cys Gly Ser Asp
            20                  25                  30

Gly Lys Ser Ala Phe Cys Thr Arg Lys Leu Cys Tyr Gln Tyr Tyr Tyr
        35                  40                  45

Gly Trp Tyr Gln Gln Lys Ala Pro Gly Ser Ala Pro Val Thr Leu Ile
    50                  55                  60

Tyr Tyr Asn Asn Lys Arg Pro Ser Asp Ile Pro Ser Arg Phe Ser Gly
65                  70                  75                  80

Ser Leu Ser Gly Ser Thr Asn Thr Leu Thr Ile Thr Gly Val Arg Ala
                85                  90                  95

Asp Asp Glu Ala Val Tyr Phe Cys Gly Ser Ala Asp Asn Ser Gly Ala
                100                 105                 110

Ala Phe Gly Ala Gly Thr Thr Leu Thr Val Leu Gly Gln Pro Lys Ala
            115                 120                 125

Ala Pro Ser Val Thr Leu Phe Pro Pro Ser Ser Glu Glu Leu Gln Ala
```

```
    130                 135                 140

Asn Lys Ala Thr Leu Val Cys Leu Ile Ser Asp Phe Tyr Pro Gly Ala
145                 150                 155                 160

Val Thr Val Ala Trp Lys Ala Asp Ser Ser Pro Val Lys Ala Gly Val
                165                 170                 175

Glu Thr Thr Thr Pro Ser Lys Gln Ser Asn Asn Lys Tyr Ala Ala Ser
            180                 185                 190

Ser Tyr Leu Ser Leu Thr Pro Glu Gln Trp Lys Ser His Arg Ser Tyr
        195                 200                 205

Ser Cys Gln Val Thr His Glu Gly Ser Thr Val Glu Lys Thr Val Ala
    210                 215                 220

Pro Thr Glu Cys Ser
225


<210> SEQ ID NO 91
<211> LENGTH: 125
<212> TYPE: PRT
<213> ORGANISM: Artificial Sequence
<220> FEATURE:
<223> OTHER INFORMATION: Synthetic

<400> SEQUENCE: 91

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Ile Tyr Tyr Cys
                85                  90                  95

Thr Lys Cys Ala Tyr Ser Ser Gly Cys Asp Tyr Glu Gly Gly Tyr Ile
            100                 105                 110

Asp Ala Trp Gly His Gly Thr Glu Val Ile Val Ser Ser
        115                 120                 125


<210> SEQ ID NO 92
<211> LENGTH: 107
<212> TYPE: PRT
<213> ORGANISM: Artificial Sequence
<220> FEATURE:
<223> OTHER INFORMATION: Synthetic

<400> SEQUENCE: 92

Ala Leu Thr Gln Pro Ala Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
        35                  40                  45

Tyr Tyr Asn Asn Lys Arg Pro Ser Asp Ile Pro Ser Arg Phe Ser Gly
    50                  55                  60

Ser Leu Ser Gly Ser Thr Asn Thr Leu Thr Ile Thr Gly Val Arg Ala
65                  70                  75                  80
```

-continued

```
Asp Asp Glu Ala Val Tyr Phe Cys Gly Ser Ala Asp Asn Ser Gly Ala
                85                  90                  95

Ala Phe Gly Ala Gly Thr Thr Leu Thr Val Leu
            100                 105


<210> SEQ ID NO 93
<211> LENGTH: 1563
<212> TYPE: DNA
<213> ORGANISM: Artificial Sequence
<220> FEATURE:
<223> OTHER INFORMATION: Synthetic

<400> SEQUENCE: 93

atggagttcg gcctgagctg gctgttcctg gtggccatcc ttaagggcgt gcagtgcctc      60

gaggtgacat gtgaacccgg tacgacgttt aaggataagt gcaacacatg taggtgcggt     120

agcgacggca aatcagcgtt ctgtacccgg aaattgtgct accagggaac tggaggaggg     180

tcggggtcct cgtcagccgt gacgttggac gagtccgggg gcggcctcca gacgcccggg     240

ggagcgctca gcctcgtctg caaggcctcc gggttcacct tcagcagtaa cgccatgggt     300

tgggtgcgac aggcgcccgg caaggggctg gagtgggtcg ctggtattga tgatgatggt     360

agtggcacaa gatacgcgcc ggcggtgaag ggccgtgcca ccatctcgag ggacaacggg     420

cagagcacac tgaggctgca gctgaacaac ctcagggctg aggacaccgg catctactac     480

tgcacgaaat gtgcttacag tagtggttgt gattatgaag gtggttatat cgacgcatgg     540

ggccacggga ccgaagtcat cgtctcctcc gctagcacca agggcccatc ggtcttcccc     600

ctggcaccct cctccaagag cacctctggg ggcacagcgg ccctgggctg cctggtcaag     660

gactacttcc ccgaaccggt gacggtgtcg tggaactcag gcgccctgac cagcggcgtg     720

cacaccttcc cggctgtcct acagtcctca ggactctact ccctcagcag cgtggtgacc     780

gtgccctcca gcagcttggg cacccagacc tacatctgca acgtgaatca caagcccagc     840

aacaccaagg tggacaagaa agttgagccc aaatcttgtg acaaaactca cacatgccca     900

ccgtgcccag cacctgaact cctgggggga ccgtcagtct tcctcttccc cccaaaaccc     960

aaggacaccc tcatgatctc ccggacccct gaggtcacat gcgtggtggt ggacgtgagc    1020

cacgaagacc ctgaggtcaa gttcaactgg tacgtggacg gcgtggaggt gcataatgcc    1080

aagacaaagc cgcgggagga gcagtacaac agcacgtacc gtgtggtcag cgtcctcacc    1140

gtcctgcacc aggactggct gaatggcaag gagtacaagt gcaaggtctc caacaaagcc    1200

ctcccagccc ccatcgagaa aaccatctcc aaagccaaag ggcagccccg agaaccacag    1260

gtgtacaccc tgcccccatc ccgggatgag ctgaccaaga accaggtcag cctgacctgc    1320

ctggtcaaag gcttctatcc cagcgacatc gccgtggagt gggagagcaa tgggcagccg    1380

gagaacaact acaagaccac gcctcccgtg ctggactccg acggctcctt cttcctctac    1440

agcaagctca ccgtggacaa gagcaggtgg cagcagggga acgtcttctc atgctccgtg    1500

atgcatgagg ctctgcacaa ccactacaca cagaagagcc tctccctgtc tccgggtaaa    1560

tga                                                                  1563


<210> SEQ ID NO 94
<211> LENGTH: 501
<212> TYPE: PRT
<213> ORGANISM: Artificial Sequence
<220> FEATURE:
<223> OTHER INFORMATION: Synthetic

<400> SEQUENCE: 94
```

```
Leu Glu Val Thr Cys Glu Pro Gly Thr Thr Phe Lys Asp Lys Cys Asn
1               5                   10                  15

Thr Cys Arg Cys Gly Ser Asp Gly Lys Ser Ala Phe Cys Thr Arg Lys
            20                  25                  30

Leu Cys Tyr Gln Gly Thr Gly Gly Gly Ser Gly Ser Ser Ser Ala Val
        35                  40                  45

Thr Leu Asp Glu Ser Gly Gly Gly Leu Gln Thr Pro Gly Gly Ala Leu
    50                  55                  60

Ser Leu Val Cys Lys Ala Ser Gly Phe Thr Phe Ser Ser Asn Ala Met
65                  70                  75                  80

Gly Trp Val Arg Gln Ala Pro Gly Lys Gly Leu Glu Trp Val Ala Gly
                85                  90                  95

Ile Asp Asp Asp Gly Ser Gly Thr Arg Tyr Ala Pro Ala Val Lys Gly
            100                 105                 110

Arg Ala Thr Ile Ser Arg Asp Asn Gly Gln Ser Thr Leu Arg Leu Gln
        115                 120                 125

Leu Asn Asn Leu Arg Ala Glu Asp Thr Gly Ile Tyr Tyr Cys Thr Lys
    130                 135                 140

Cys Ala Tyr Ser Ser Gly Cys Asp Tyr Glu Gly Gly Tyr Ile Asp Ala
145                 150                 155                 160

Trp Gly His Gly Thr Glu Val Ile Val Ser Ser Ala Ser Thr Lys Gly
                165                 170                 175

Pro Ser Val Phe Pro Leu Ala Pro Ser Ser Lys Ser Thr Ser Gly Gly
            180                 185                 190

Thr Ala Ala Leu Gly Cys Leu Val Lys Asp Tyr Phe Pro Glu Pro Val
        195                 200                 205

Thr Val Ser Trp Asn Ser Gly Ala Leu Thr Ser Gly Val His Thr Phe
    210                 215                 220

Pro Ala Val Leu Gln Ser Ser Gly Leu Tyr Ser Leu Ser Ser Val Val
225                 230                 235                 240

Thr Val Pro Ser Ser Ser Leu Gly Thr Gln Thr Tyr Ile Cys Asn Val
                245                 250                 255

Asn His Lys Pro Ser Asn Thr Lys Val Asp Lys Lys Val Glu Pro Lys
            260                 265                 270

Ser Cys Asp Lys Thr His Thr Cys Pro Pro Cys Pro Ala Pro Glu Leu
        275                 280                 285

Leu Gly Gly Pro Ser Val Phe Leu Phe Pro Pro Lys Pro Lys Asp Thr
    290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
    370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Lys Asn Gln
                405                 410                 415
```

```
Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Lys Leu
    450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys
            500


<210> SEQ ID NO 95
<211> LENGTH: 1563
<212> TYPE: DNA
<213> ORGANISM: Artificial Sequence
<220> FEATURE:
<223> OTHER INFORMATION: Synthetic

<400> SEQUENCE: 95

atggagttcg gcctgagctg gctgttcctg gtggccatcc ttaagggcgt gcagtgcttg      60

gaagtgacgt gtgagcccgg aacgacattc aaagacaagt gcaatacttg tcggtgcggt     120

tcagatggga aatcggcggt ctgcacaaag ctctggtgta accagggcac cggtggaggg     180

tcgggatcca gctcagccgt gacgttggac gagtccgggg gcggcctcca gacgcccggg     240

ggagcgctca gcctcgtctg caaggcctcc gggttcacct tcagcagtaa cgccatgggt     300

tgggtgcgac aggcgcccgg caaggggctg gagtgggtcg ctggtattga tgatgatggt     360

agtggcacaa gatacgcgcc ggcggtgaag ggccgtgcca ccatctcgag ggacaacggg     420

cagagcacac tgaggctgca gctgaacaac ctcagggctg aggacaccgg catctactac     480

tgcacgaaat gtgcttacag tagtggttgt gattatgaag gtggttatat cgacgcatgg     540

ggccacggga ccgaagtcat cgtctcctcc gctagcacca agggcccatc ggtcttcccc     600

ctggcaccct cctccaagag cacctctggg ggcacagcgg ccctgggctg cctggtcaag     660

gactacttcc ccgaaccggt gacggtgtcg tggaactcag gcgccctgac cagcggcgtg     720

cacaccttcc cggctgtcct acagtcctca ggactctact ccctcagcag cgtggtgacc     780

gtgccctcca gcagcttggg cacccagacc tacatctgca acgtgaatca caagcccagc     840

aacaccaagg tggacaagaa agttgagccc aaatcttgtg acaaaactca cacatgccca     900

ccgtgcccag cacctgaact cctgggggga ccgtcagtct tcctcttccc cccaaaaccc     960

aaggacaccc tcatgatctc ccggacccct gaggtcacat gcgtggtggt ggacgtgagc    1020

cacgaagacc ctgaggtcaa gttcaactgg tacgtggacg gcgtggaggt gcataatgcc    1080

aagacaaagc cgcgggagga gcagtacaac agcacgtacc gtgtggtcag cgtcctcacc    1140

gtcctgcacc aggactggct gaatggcaag gagtacaagt gcaaggtctc caacaaagcc    1200

ctcccagccc ccatcgagaa aaccatctcc aaagccaaag ggcagccccg agaaccacag    1260

gtgtacaccc tgcccccatc ccgggatgag ctgaccaaga accaggtcag cctgacctgc    1320

ctggtcaaag gcttctatcc cagcgacatc gccgtggagt gggagagcaa tgggcagccg    1380

gagaacaact acaagaccac gcctcccgtg ctggactccg acggctcctt cttcctctac    1440

agcaagctca ccgtggacaa gagcaggtgg cagcagggga acgtcttctc atgctccgtg    1500

atgcatgagg ctctgcacaa ccactacaca cagaagagcc tctccctgtc tccgggtaaa    1560
```

tga 1563

<210> SEQ ID NO 96
<211> LENGTH: 501
<212> TYPE: PRT
<213> ORGANISM: Artificial Sequence
<220> FEATURE:
<223> OTHER INFORMATION: Synthetic

<400> SEQUENCE: 96

Leu Glu Val Thr Cys Glu Pro Gly Thr Thr Phe Lys Asp Lys Cys Asn
1 5 10 15

Thr Cys Arg Cys Gly Ser Asp Gly Lys Ser Ala Val Cys Thr Lys Leu
20 25 30

Trp Cys Asn Gln Gly Thr Gly Gly Gly Ser Gly Ser Ser Ser Ala Val
35 40 45

Thr Leu Asp Glu Ser Gly Gly Gly Leu Gln Thr Pro Gly Gly Ala Leu
50 55 60

Ser Leu Val Cys Lys Ala Ser Gly Phe Thr Phe Ser Ser Asn Ala Met
65 70 75 80

Gly Trp Val Arg Gln Ala Pro Gly Lys Gly Leu Glu Trp Val Ala Gly
85 90 95

Ile Asp Asp Asp Gly Ser Gly Thr Arg Tyr Ala Pro Ala Val Lys Gly
100 105 110

Arg Ala Thr Ile Ser Arg Asp Asn Gly Gln Ser Thr Leu Arg Leu Gln
115 120 125

Leu Asn Asn Leu Arg Ala Glu Asp Thr Gly Ile Tyr Tyr Cys Thr Lys
130 135 140

Cys Ala Tyr Ser Ser Gly Cys Asp Tyr Glu Gly Gly Tyr Ile Asp Ala
145 150 155 160

Trp Gly His Gly Thr Glu Val Ile Val Ser Ser Ala Ser Thr Lys Gly
165 170 175

Pro Ser Val Phe Pro Leu Ala Pro Ser Ser Lys Ser Thr Ser Gly Gly
180 185 190

Thr Ala Ala Leu Gly Cys Leu Val Lys Asp Tyr Phe Pro Glu Pro Val
195 200 205

Thr Val Ser Trp Asn Ser Gly Ala Leu Thr Ser Gly Val His Thr Phe
210 215 220

Pro Ala Val Leu Gln Ser Ser Gly Leu Tyr Ser Leu Ser Ser Val Val
225 230 235 240

Thr Val Pro Ser Ser Ser Leu Gly Thr Gln Thr Tyr Ile Cys Asn Val
245 250 255

Asn His Lys Pro Ser Asn Thr Lys Val Asp Lys Lys Val Glu Pro Lys
260 265 270

Ser Cys Asp Lys Thr His Thr Cys Pro Pro Cys Pro Ala Pro Glu Leu
275 280 285

Leu Gly Gly Pro Ser Val Phe Leu Phe Pro Pro Lys Pro Lys Asp Thr
290 295 300

Leu Met Ile Ser Arg Thr Pro Glu Val Thr Cys Val Val Val Asp Val
305 310 315 320

Ser His Glu Asp Pro Glu Val Lys Phe Asn Trp Tyr Val Asp Gly Val
325 330 335

Glu Val His Asn Ala Lys Thr Lys Pro Arg Glu Glu Gln Tyr Asn Ser
340 345 350

-continued

```
Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
    370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Lys Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Lys Leu
    450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys
            500


<210> SEQ ID NO 97
<211> LENGTH: 1563
<212> TYPE: DNA
<213> ORGANISM: Artificial Sequence
<220> FEATURE:
<223> OTHER INFORMATION: Synthetic

<400> SEQUENCE: 97

atggagttcg gcctgagctg gctgttcctg gtggccatcc ttaagggcgt gcagtgcgcc      60

gtgacgttgg acgagtccgg gggcggcctc cagacgcccg gggagcgct cagcctcgtc      120

tgcaaggcct ccgggttcac cttcagcagt aacgccatgg gttgggtgcg acaggcgccc    180

ggcaaggggc tggagtgggt cgctggtatt gatgatgatg gtagtggcac aagatacgcg    240

ccggcggtga agggccgtgc caccatctcg agggacaacg ggcagagcac actgaggctg    300

cagctgaaca acctcagggc tgaggacacc ggcatctact actgcacgaa atgtgcttac    360

agtagtggtt gtgattatga aggtggttat atcgacgcat ggggccacgg gaccgaagtc    420

atcgtctcct ccgctagcac caagggccca tcggtcttcc ccctggcacc ctcctccaag    480

agcacctctg ggggcacagc ggccctgggc tgcctggtca aggactactt ccccgaaccg    540

gtgacggtgt cgtggaactc aggcgccctg accagcggcg tgcacacctt cccggctgtc    600

ctacagtcct caggactcta ctccctcagc agcgtggtga ccgtgccctc cagcagcttg    660

ggcacccaga cctacatctg caacgtgaat cacaagccca gcaacaccaa ggtggacaag    720

aaagttgagc ccaaatcttg tgacaaaact cacacatgcc caccgtgccc agcacctgaa    780

ctcctggggg gaccgtcagt cttcctcttc cccccaaaac ccaaggacac cctcatgatc    840

tcccggaccc ctgaggtcac atgcgtggtg gtggacgtga gccacgaaga ccctgaggtc    900

aagttcaact ggtacgtgga cggcgtggag gtgcataatg ccaagacaaa gccgcgggag    960

gagcagtaca acagcacgta ccgtgtggtc agcgtcctca ccgtcctgca ccaggactgg   1020

ctgaatggca aggagtacaa gtgcaaggtc tccaacaaag ccctcccagc ccccatcgag   1080

aaaaccatct ccaaagccaa agggcagccc cgagaaccac aggtgtacac cctgccccca   1140

tcccgggatg agctgaccaa gaaccaggtc agcctgacct gcctggtcaa aggcttctat   1200
```

```
cccagcgaca tcgccgtgga gtgggagagc aatgggcagc cggagaacaa ctacaagacc   1260

acgcctcccg tgctggactc cgacggctcc ttcttcctct acagcaagct caccgtggac   1320

aagagcaggt ggcagcaggg gaacgtcttc tcatgctccg tgatgcatga ggctctgcac   1380

aaccactaca cacagaagag cctctccctg tctccgggta aagccgctgg tggtagtggt   1440

ctcgaggtga catgtgaacc cggtacgacg tttaaggata agtgcaacac atgtaggtgc   1500

ggtagcgacg gcaaatcagc gttctgtacc cggaaattgt gctaccaggg tagtggtgct   1560

tga                                                                 1563


<210> SEQ ID NO 98
<211> LENGTH: 501
<212> TYPE: PRT
<213> ORGANISM: Artificial Sequence
<220> FEATURE:
<223> OTHER INFORMATION: Synthetic

<400> SEQUENCE: 98

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Ile Tyr Tyr Cys
                85                  90                  95

Thr Lys Cys Ala Tyr Ser Ser Gly Cys Asp Tyr Glu Gly Gly Tyr Ile
            100                 105                 110

Asp Ala Trp Gly His Gly Thr Glu Val Ile Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285
```

```
Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Ala Ala Gly Gly Ser Gly Leu Glu Val
    450                 455                 460

Thr Cys Glu Pro Gly Thr Thr Phe Lys Asp Lys Cys Asn Thr Cys Arg
465                 470                 475                 480

Cys Gly Ser Asp Gly Lys Ser Ala Phe Cys Thr Arg Lys Leu Cys Tyr
                485                 490                 495

Gln Gly Ser Gly Ala
            500
```

<210> SEQ ID NO 99
<211> LENGTH: 1563
<212> TYPE: DNA
<213> ORGANISM: Artificial Sequence
<220> FEATURE:
<223> OTHER INFORMATION: Synthetic

<400> SEQUENCE: 99

```
atggagttcg gcctgagctg gctgttcctg gtggccatcc ttaagggcgt gcagtgcgcc      60

gtgacgttgg acgagtccgg gggcggcctc cagacgcccg ggggagcgct cagcctcgtc     120

tgcaaggcct ccgggttcac cttcagcagt aacgccatgg gttgggtgcg acaggcgccc     180

ggcaaggggc tggagtgggt cgctggtatt gatgatgatg gtagtggcac aagatacgcg     240

ccggcggtga agggccgtgc caccatctcg agggacaacg ggcagagcac actgaggctg     300

cagctgaaca acctcagggc tgaggacacc ggcatctact actgcacgaa atgtgcttac     360

agtagtggtt gtgattatga aggtggttat atcgacgcat ggggccacgg gaccgaagtc     420

atcgtctcct ccgctagcac caagggccca tcggtcttcc ccctggcacc ctcctccaag     480

agcacctctg ggggcacagc ggccctgggc tgcctggtca aggactactt ccccgaaccg     540

gtgacggtgt cgtggaactc aggcgccctg accagcggcg tgcacacctt cccggctgtc     600

ctacagtcct caggactcta ctccctcagc agcgtggtga ccgtgccctc cagcagcttg     660

ggcacccaga cctacatctg caacgtgaat cacaagccca gcaacaccaa ggtggacaag     720

aaagttgagc ccaaatcttg tgacaaaact cacacatgcc caccgtgccc agcacctgaa     780

ctcctggggg gaccgtcagt cttcctcttc cccccaaaac ccaaggacac cctcatgatc     840
```

```
tcccggaccc ctgaggtcac atgcgtggtg gtggacgtga gccacgaaga ccctgaggtc    900

aagttcaact ggtacgtgga cggcgtggag gtgcataatg ccaagacaaa gccgcgggag    960

gagcagtaca acagcacgta ccgtgtggtc agcgtcctca ccgtcctgca ccaggactgg   1020

ctgaatggca aggagtacaa gtgcaaggtc tccaacaaag ccctcccagc ccccatcgag   1080

aaaaccatct ccaaagccaa agggcagccc cgagaaccac aggtgtacac cctgccccca   1140

tcccgggatg agctgaccaa gaaccaggtc agcctgacct gcctggtcaa aggcttctat   1200

cccagcgaca tcgccgtgga gtgggagagc aatgggcagc cggagaacaa ctacaagacc   1260

acgcctcccg tgctggactc cgacggctcc ttcttcctct acagcaagct caccgtggac   1320

aagagcaggt ggcagcaggg gaacgtcttc tcatgctccg tgatgcatga ggctctgcac   1380

aaccactaca cacagaagag cctctccctg tctccgggta aagccgctgg tggtagtggt   1440

ttggaagtga cgtgtgagcc cggaacgaca ttcaaagaca agtgcaatac ttgtcggtgc   1500

ggttcagatg ggaaatcggc ggtctgcaca aagctctggt gtaaccaggg tagtggtgct   1560

tga                                                                 1563
```

<210> SEQ ID NO 100
<211> LENGTH: 501
<212> TYPE: PRT
<213> ORGANISM: Artificial Sequence
<220> FEATURE:
<223> OTHER INFORMATION: Synthetic

<400> SEQUENCE: 100

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Ile Tyr Tyr Cys
                85                  90                  95

Thr Lys Cys Ala Tyr Ser Ser Gly Cys Asp Tyr Glu Gly Gly Tyr Ile
            100                 105                 110

Asp Ala Trp Gly His Gly Thr Glu Val Ile Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220
```

Pro Lys Ser Cys Asp Lys Thr His Thr Cys Pro Pro Cys Pro Ala Pro
225 230 235 240

Glu Leu Leu Gly Gly Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ala Pro Ile Glu Lys Thr Ile Ser Lys Ala Lys Gly Gln Pro Arg
340 345 350

Glu Pro Gln Val Tyr Thr Leu Pro Pro Ser Arg Asp Glu Leu Thr Lys
355 360 365

Asn Gln Val Ser Leu Thr Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro Gly Lys Ala Ala Gly Gly Ser Gly Leu Glu Val
450 455 460

Thr Cys Glu Pro Gly Thr Thr Phe Lys Asp Lys Cys Asn Thr Cys Arg
465 470 475 480

Cys Gly Ser Asp Gly Lys Ser Ala Val Cys Thr Lys Leu Trp Cys Asn
485 490 495

Gln Gly Ser Gly Ala
500

<210> SEQ ID NO 101
<211> LENGTH: 837
<212> TYPE: DNA
<213> ORGANISM: Artificial Sequence
<220> FEATURE:
<223> OTHER INFORMATION: Synthetic

<400> SEQUENCE: 101
atggcctgga ttcctctact tctccccctc ctcactctct gcacaggatc cgaagccctc 60
gaggtgacat gtgaacccgg tacgacgttt aaggataagt gcaacacatg taggtgcggt 120
agcgacggca aatcagcgtt ctgtacccgg aaattgtgct accagggaac tggaggaggg 180
tcggggtcct cgtcagcgct gactcagcct gcctcggtgt cagcaaaccc aggagaaacc 240
gtcaagatca cctgctccgg gggtggcagc tatgctggaa gttactatta tggctggtac 300
cagcagaagg cacctggcag tgcccctgtc actctgatct attacaacaa caagagaccc 360
tcggacatcc cttcacgatt ctccggttcc ctatccggct ccacaaacac attaaccatc 420
actggggtcc gagccgatga cgaggctgtc tatttctgtg ggagtgcaga caacagtggt 480
gctgcatttg gggccgggac aaccctgaca gtacttggtc agcccaaggc tgccccttcg 540
gtcaccctgt tcccgccctc ctctgaggag cttcaagcca acaaggccac actggtgtgt 600
ctcataagtg acttctaccc gggagccgtg acagtggcct ggaaggcaga tagcagcccc 660
gtcaaggcgg gagtggagac caccacaccc tccaaacaaa gcaacaacaa gtacgcggcc 720
agcagctatc tgagcctgac gcctgagcag tggaagtccc acagaagcta cagctgccag 780
gtcacgcatg aagggagcac cgtggagaag acagtggccc ctacagaatg ttcatag 837

<210> SEQ ID NO 102
<211> LENGTH: 258
<212> TYPE: PRT
<213> ORGANISM: Artificial Sequence
<220> FEATURE:
<223> OTHER INFORMATION: Synthetic

<400> SEQUENCE: 102

Leu Glu Val Thr Cys Glu Pro Gly Thr Thr Phe Lys Asp Lys Cys Asn
1 5 10 15

Thr Cys Arg Cys Gly Ser Asp Gly Lys Ser Ala Phe Cys Thr Arg Lys
20 25 30

Leu Cys Tyr Gln Gly Thr Gly Gly Gly Ser Gly Ser Ser Ser Ala Leu
35 40 45

Thr Gln Pro Ala Ser Val Ser Ala Asn Pro Gly Glu Thr Val Lys Ile
50 55 60

Thr Cys Ser Gly Gly Gly Ser Tyr Ala Gly Ser Tyr Tyr Tyr Gly Trp
65 70 75 80

Tyr Gln Gln Lys Ala Pro Gly Ser Ala Pro Val Thr Leu Ile Tyr Tyr
85 90 95

Asn Asn Lys Arg Pro Ser Asp Ile Pro Ser Arg Phe Ser Gly Ser Leu
100 105 110

Ser Gly Ser Thr Asn Thr Leu Thr Ile Thr Gly Val Arg Ala Asp Asp
115 120 125

Glu Ala Val Tyr Phe Cys Gly Ser Ala Asp Asn Ser Gly Ala Ala Phe
130 135 140

Gly Ala Gly Thr Thr Leu Thr Val Leu Gly Gln Pro Lys Ala Ala Pro
145 150 155 160

Ser Val Thr Leu Phe Pro Pro Ser Ser Glu Glu Leu Gln Ala Asn Lys
165 170 175

Ala Thr Leu Val Cys Leu Ile Ser Asp Phe Tyr Pro Gly Ala Val Thr
180 185 190

Val Ala Trp Lys Ala Asp Ser Ser Pro Val Lys Ala Gly Val Glu Thr
195 200 205

Thr Thr Pro Ser Lys Gln Ser Asn Asn Lys Tyr Ala Ala Ser Ser Tyr
210 215 220

Leu Ser Leu Thr Pro Glu Gln Trp Lys Ser His Arg Ser Tyr Ser Cys
225 230 235 240

Gln Val Thr His Glu Gly Ser Thr Val Glu Lys Thr Val Ala Pro Thr
245 250 255

Glu Cys

<210> SEQ ID NO 103
<211> LENGTH: 837
<212> TYPE: DNA
<213> ORGANISM: Artificial Sequence
<220> FEATURE:

<223> OTHER INFORMATION: Synthetic

<400> SEQUENCE: 103
atggcctgga ttcctctact tctccccctc ctcactctct gcacaggatc cgaagccttg 60
gaagtgacgt gtgagcccgg aacgacattc aaagacaagt gcaatacttg tcggtgcggt 120
tcagatggga aatcggcggt ctgcacaaag ctctggtgta accagggcac cggtggaggg 180
tcgggatcca gctcagcgct gactcagcct gcctcggtgt cagcaaaccc aggagaaacc 240
gtcaagatca cctgctccgg gggtggcagc tatgctggaa gttactatta tggctggtac 300
cagcagaagg cacctggcag tgcccctgtc actctgatct attacaacaa caagagaccc 360
tcggacatcc cttcacgatt ctccggttcc ctatccggct ccacaaacac attaaccatc 420
actggggtcc gagccgatga cgaggctgtc tatttctgtg ggagtgcaga caacagtggt 480
gctgcatttg ggccgggac aaccctgaca gtacttggtc agcccaaggc tgccccttcg 540
gtcaccctgt tcccgccctc ctctgaggag cttcaagcca acaaggccac actggtgtgt 600
ctcataagtg acttctaccc gggagccgtg acagtggcct ggaaggcaga tagcagcccc 660
gtcaaggcgg gagtggagac caccacaccc tccaaacaaa gcaacaacaa gtacgcggcc 720
agcagctatc tgagcctgac gcctgagcag tggaagtccc acagaagcta cagctgccag 780
gtcacgcatg aagggagcac cgtggagaag acagtggccc ctacagaatg ttcatag 837

<210> SEQ ID NO 104
<211> LENGTH: 259
<212> TYPE: PRT
<213> ORGANISM: Artificial Sequence
<220> FEATURE:
<223> OTHER INFORMATION: Synthetic

<400> SEQUENCE: 104

Leu Glu Val Thr Cys Glu Pro Gly Thr Thr Phe Lys Asp Lys Cys Asn
1               5                   10                  15

Thr Cys Arg Cys Gly Ser Asp Gly Lys Ser Ala Val Cys Thr Lys Leu
            20                  25                  30

Trp Cys Asn Gln Gly Thr Gly Gly Gly Ser Gly Ser Ser Ser Ala Leu
        35                  40                  45

Thr Gln Pro Ala Ser Val Ser Ala Asn Pro Gly Glu Thr Val Lys Ile
    50                  55                  60

Thr Cys Ser Gly Gly Gly Ser Tyr Ala Gly Ser Tyr Tyr Tyr Gly Trp
65                  70                  75                  80

Tyr Gln Gln Lys Ala Pro Gly Ser Ala Pro Val Thr Leu Ile Tyr Tyr
                85                  90                  95

Asn Asn Lys Arg Pro Ser Asp Ile Pro Ser Arg Phe Ser Gly Ser Leu
            100                 105                 110

Ser Gly Ser Thr Asn Thr Leu Thr Ile Thr Gly Val Arg Ala Asp Asp
        115                 120                 125

Glu Ala Val Tyr Phe Cys Gly Ser Ala Asp Asn Ser Gly Ala Ala Phe
    130                 135                 140

Gly Ala Gly Thr Thr Leu Thr Val Leu Gly Gln Pro Lys Ala Ala Pro
145                 150                 155                 160

Ser Val Thr Leu Phe Pro Pro Ser Ser Glu Glu Leu Gln Ala Asn Lys
                165                 170                 175

Ala Thr Leu Val Cys Leu Ile Ser Asp Phe Tyr Pro Gly Ala Val Thr
            180                 185                 190

Val Ala Trp Lys Ala Asp Ser Ser Pro Val Lys Ala Gly Val Glu Thr 195 200 205

Thr Thr Pro Ser Lys Gln Ser Asn Asn Lys Tyr Ala Ala Ser Ser Tyr
210 215 220

Leu Ser Leu Thr Pro Glu Gln Trp Lys Ser His Arg Ser Tyr Ser Cys
225 230 235 240

Gln Val Thr His Glu Gly Ser Thr Val Glu Lys Thr Val Ala Pro Thr
245 250 255

Glu Cys Ser

<210> SEQ ID NO 105
<211> LENGTH: 837
<212> TYPE: DNA
<213> ORGANISM: Artificial Sequence
<220> FEATURE:
<223> OTHER INFORMATION: Synthetic

<400> SEQUENCE: 105
atggcctgga ttcctctact tctcccctc ctcactctct gcacaggatc cgaagccgcg 60
ctgactcagc ctgcctcggt gtcagcaaac ccaggagaaa ccgtcaagat cacctgctcc 120
gggggtggca gctatgctgg aagttactat tatggctggt accagcagaa ggcacctggc 180
agtgcccctg tcactctgat ctattacaac aacaagagac cctcggacat cccttcacga 240
ttctccggtt ccctatccgg ctccacaaac acattaacca tcactggggt ccgagccgat 300
gacgaggctg tctatttctg tgggagtgca gacaacagtg gtgctgcatt tggggccggg 360
acaaccctga cagtacttgg tcagcccaag gctgcccctt cggtcaccct gttcccgccc 420
tcctctgagg agcttcaagc caacaaggcc acactggtgt gtctcataag tgacttctac 480
ccgggagccg tgacagtggc ctggaaggca gatagcagcc ccgtcaaggc gggagtggag 540
accaccacac cctccaaaca aagcaacaac aagtacgcgg ccagcagcta tctgagcctg 600
acgcctgagc agtggaagtc ccacagaagc tacagctgcc aggtcacgca tgaagggagc 660
accgtggaga agacagtggc ccctacagaa tgttcagccg ctggtggtag tggtctcgag 720
gtgacatgtg aacccggtac gacgtttaag gataagtgca acacatgtag gtgcggtagc 780
gacggcaaat cagcgttctg tacccggaaa ttgtgctacc agggtagtgg tgcttag 837

<210> SEQ ID NO 106
<211> LENGTH: 259
<212> TYPE: PRT
<213> ORGANISM: Artificial Sequence
<220> FEATURE:
<223> OTHER INFORMATION: Synthetic

<400> SEQUENCE: 106

Ala Leu Thr Gln Pro Ala Ser Val Ser Ala Asn Pro Gly Glu Thr Val
1 5 10 15

Lys Ile Thr Cys Ser Gly Gly Gly Ser Tyr Ala Gly Ser Tyr Tyr Tyr
20 25 30

Gly Trp Tyr Gln Gln Lys Ala Pro Gly Ser Ala Pro Val Thr Leu Ile
35 40 45

Tyr Tyr Asn Asn Lys Arg Pro Ser Asp Ile Pro Ser Arg Phe Ser Gly
50 55 60

Ser Leu Ser Gly Ser Thr Asn Thr Leu Thr Ile Thr Gly Val Arg Ala
65 70 75 80

Asp Asp Glu Ala Val Tyr Phe Cys Gly Ser Ala Asp Asn Ser Gly Ala
85 90 95

Ala Phe Gly Ala Gly Thr Thr Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser Ala Ala Gly Gly Ser Gly Leu Glu Val Thr Cys
    210                 215                 220

Glu Pro Gly Thr Thr Phe Lys Asp Lys Cys Asn Thr Cys Arg Cys Gly
225                 230                 235                 240

Ser Asp Gly Lys Ser Ala Phe Cys Thr Arg Lys Leu Cys Tyr Gln Gly
                245                 250                 255

Ser Gly Ala

<210> SEQ ID NO 107
<211> LENGTH: 837
<212> TYPE: DNA
<213> ORGANISM: Artificial Sequence
<220> FEATURE:
<223> OTHER INFORMATION: Synthetic

<400> SEQUENCE: 107
atggcctgga ttcctctact tctccccctc ctcactctct gcacaggatc cgaagccgcg 60
ctgactcagc ctgcctcggt gtcagcaaac ccaggagaaa ccgtcaagat cacctgctcc 120
gggggtggca gctatgctgg aagttactat tatggctggt accagcagaa ggcacctggc 180
agtgcccctg tcactctgat ctattacaac aacaagagac cctcggacat cccttcacga 240
ttctccggtt ccctatccgg ctccacaaac acattaacca tcactggggt ccgagccgat 300
gacgaggctg tctatttctg tgggagtgca gacaacagtg gtgctgcatt tggggccggg 360
acaaccctga cagtacttgg tcagcccaag gctgcccctt cggtcaccct gttcccgccc 420
tcctctgagg agcttcaagc caacaaggcc acactggtgt gtctcataag tgacttctac 480
ccgggagccg tgacagtggc ctggaaggca gatagcagcc ccgtcaaggc gggagtggag 540
accaccacac cctccaaaca aagcaacaac aagtacgcgg ccagcagcta tctgagcctg 600
acgcctgagc agtggaagtc ccacagaagc tacagctgcc aggtcacgca tgaagggagc 660
accgtggaga agacagtggc ccctacagaa tgttcagccg ctggtggtag tggtttggaa 720
gtgacgtgtg agcccggaac gacattcaaa gacaagtgca atacttgtcg gtgcggttca 780
gatgggaaat cggcggtctg cacaaagctc tggtgtaacc agggtagtgg tgcttag 837

<210> SEQ ID NO 108
<211> LENGTH: 259
<212> TYPE: PRT
<213> ORGANISM: Artificial Sequence
<220> FEATURE:
<223> OTHER INFORMATION: Synthetic

<400> SEQUENCE: 108

-continued

```
Ala Leu Thr Gln Pro Ala Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
        35                  40                  45

Tyr Tyr Asn Asn Lys Arg Pro Ser Asp Ile Pro Ser Arg Phe Ser Gly
    50                  55                  60

Ser Leu Ser Gly Ser Thr Asn Thr Leu Thr Ile Thr Gly Val Arg Ala
65                  70                  75                  80

Asp Asp Glu Ala Val Tyr Phe Cys Gly Ser Ala Asp Asn Ser Gly Ala
                85                  90                  95

Ala Phe Gly Ala Gly Thr Thr Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser Ala Ala Gly Gly Ser Gly Leu Glu Val Thr Cys
    210                 215                 220

Glu Pro Gly Thr Thr Phe Lys Asp Lys Cys Asn Thr Cys Arg Cys Gly
225                 230                 235                 240

Ser Asp Gly Lys Ser Ala Val Cys Thr Lys Leu Trp Cys Asn Gln Gly
                245                 250                 255

Ser Gly Ala
```